United States Patent
Reed et al.

(10) Patent No.: US 8,431,363 B2
(45) Date of Patent: Apr. 30, 2013

(54) POLYNUCLEOTIDES ENCODING THERAPEUTIC INHIBITORS OF PAI-1

(75) Inventors: Thomas D. Reed, Arlington, VA (US); Richard E. Peterson, Blacksburg, VA (US); Charles C. Reed, Souderton, PA (US); Joan Mazzarelli Sopczynski, Oreland, PA (US); Bethany L. Merenick, Frederick, MD (US); Jonathan Carson, Germantown, MD (US); Catherine L. Bair, Alexandria, VA (US); Elena Tasheva, Germantown, MD (US)

(73) Assignee: Intrexon Corporation, Blacksburg, VA (US)

( * ) Notice: Subject to any disclaimer, the term of this patent is extended or adjusted under 35 U.S.C. 154(b) by 30 days.

(21) Appl. No.: 12/812,127

(22) PCT Filed: Jan. 9, 2009

(86) PCT No.: PCT/US2009/000155
§ 371 (c)(1),
(2), (4) Date: Sep. 1, 2010

(87) PCT Pub. No.: WO2009/089059
PCT Pub. Date: Jul. 16, 2009

(65) Prior Publication Data
US 2011/0055940 A1 Mar. 3, 2011

Related U.S. Application Data

(60) Provisional application No. 61/020,137, filed on Jan. 9, 2008, provisional application No. 61/080,640, filed on Jul. 14, 2008.

(51) Int. Cl.
*C12P 21/04* (2006.01)
*C07H 21/04* (2006.01)

(52) U.S. Cl.
USPC .......................................... 435/69.7; 536/23.4

(58) Field of Classification Search ........................ None
See application file for complete search history.

(56) References Cited

U.S. PATENT DOCUMENTS

| | | | |
|---|---|---|---|
| 5,639,726 A | 6/1997 | Lawrence et al. | |
| 7,071,295 B2 | 7/2006 | Reed | |
| 7,241,613 B1 | 7/2007 | Willins et al. | |
| 2003/0180934 A1 | 9/2003 | Ni et al. | |
| 2004/0185556 A1 | 9/2004 | Reed | |
| 2008/0032947 A1 | 2/2008 | Reed | |
| 2008/0050808 A1 | 2/2008 | Reed et al. | |
| 2008/0051360 A1 | 2/2008 | Reed et al. | |
| 2008/0213834 A1 | 9/2008 | Reed et al. | |
| 2008/0220475 A1 | 9/2008 | Reed et al. | |
| 2009/0186379 A1 | 7/2009 | Reed | |
| 2009/0215173 A1 | 8/2009 | Reed | |
| 2009/0215866 A1 | 8/2009 | Reed | |
| 2010/0279378 A1 | 11/2010 | Bachinsky et al. | |

FOREIGN PATENT DOCUMENTS

| | | |
|---|---|---|
| DE | 100 53 251 A1 | 5/2002 |
| WO | WO 03/095476 A2 | 11/2003 |
| WO | WO 2005/040336 A2 | 5/2005 |
| WO | WO 2005/116231 A1 | 12/2005 |
| WO | WO 2007/048103 A2 | 4/2007 |
| WO | WO 2007/076166 A2 | 7/2007 |
| WO | WO 2008/119058 A2 | 10/2008 |
| WO | WO 2009/014564 A2 | 1/2009 |

OTHER PUBLICATIONS

USPTO in house alignment of GenBank Acc#1LMW_B May 9, 1996 from Spraggon et al, Structure 3 (7), 681-691 (1995). Alignment with Seq ID No. 51.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Deng et al, Structural and Functional Analysis of the Plasminogen Activator Inhibitor-1 Binding Motif in the Somatomedin B Domain of Vitronectin. J Biol Chem vol. 271, No. 22, Issue of May 31, pp. 12716-12723, 1996.*
Mikolajczyk et al, Prostatic Human Kallikrein 2 Inactivates and Complexes With Plasminogen Activator Inhibitor-1. Int. J. Cancer: 81, 438-442 (1999).*
Guo et al, Protein tolerance to random amino acid change. Proc Natl Acad Sci U S A. Jun. 22, 2004;101(25):9205-9210. Epub Jun. 14, 2004.*
Cale, J. and Lawrence, D.A., "Structure-Function Relationships of Plasminogen Activator Inhibitor-1 and Its Potential as a Therapeutic Agent," *Curr. Drug Targets* 8: 971-981, Bentham Science Publishers Ltd., AE (2007).
Davis, S., et al., "The Receptor for Ciliary Neurotrophic Factor," *Science* 253(5015): 59-63, American Association for the Advancement of Science, US (1991).
Levine, S.J., "Mechanisms of Soluble Cytokine Receptor Generation," *J. Immunol.* 173: 5343-5348, The American Association of Immunologists, Inc., US (2004).
Sobel, B.E., et al., "Intramural Plasminogen Activator Inhibitor Type-1 and Coronary Atherosclerosis," *Arterioscler. Thromb. Vasc. Biol.* 23: 1979-1989, American Heart Association, Inc., US (2003).

(Continued)

*Primary Examiner* — Sheridan Swope
(74) *Attorney, Agent, or Firm* — Sterne, Kessler, Goldstein & Fox P.L.L.C.

(57) ABSTRACT

The invention relates to mammalian PAI-I ligands and modulators. In particular, the invention relates to polypeptides, polypeptide compositions and polynucleotides that encode polypeptides that are ligands and/or modulators of PAI-I. The invention also relates to polyligands that are homopolyligands or heteropolyligands that modulate PAI-I activity. The invention also relates to ligands and polyligands localized to a region of a cell. The invention also relates to localization tethers and promoter sequences that can be used to provide spatial control of the PAI-I ligands and polyligands. The invention also relates to inducible gene switches that can be used to provide temporal control of the PAI-I ligands and polyligands. The invention also relates to methods of treating or preventing atherosclerosis. The invention also relates to methods of treating or preventing fibrosis.

6 Claims, 32 Drawing Sheets

OTHER PUBLICATIONS

Takeshita, K., et al., "Increased Expression of Plasminogen Activator Inhibitor-1 in Cardiomyocytes Contributes to Cardiac Fibrosis after Myocardial Infarction," *Am. J. Pathol. 164*: 449-456, American Society for Investigative Pathology, US (2004).

Weisberg, A.D., et al., "Pharmacological Inhibition and Genetic Deficiency of Plasminogen Activator Inhibitor-1 Attenuates Angiotensin II/Salt-Induced Aortic Remodeling," *Arterioscler. Thromb. Vasc. Biol. 25*: 365-371, American Heart Association, Inc., US (2005).

International Search Report for International Application No. PCT/US09/00155, ISA-US, United States, mailed on Jul. 1, 2009.

Eitzman, D.T., et al.,"Peptide-mediated Inactivation of Recombinant and Platelet Plasminogen Activator Inhibitor-1 In Vitro," *J. Clin. Invest. 95*:2416-2420, The American Society for Clinical Investigation, Inc., United States (1995).

Muehlenweg, B., et al., "Epitope Mapping of Monoclonal Antibodies Directed to PAI-1 Using PAI-1/PAI-2 Chimera and PAI-1-Derived Synthetic Peptides," *Thromb. Res. 98*:73-81, Elsevier Science Ltd., United States (2000).

Stassen, J.M. et al., English language Abstract of German Patent Publication No. DE 100 532 51 A1, European Patent Office, espacenet database—Worldwide (2000) (Listed as document FP6 on the accompanying PTO/SB/08 A equivalent form).

Cui, S.J. and Han, W., "Plasminogen activator inhibitor type 1," UniPro Database Accession No. Q6R745_CANFA, 4 pages (2004).

\* cited by examiner

| LIGAND Z | EPITOPE OR REPORTER |
|---|---|

FIGURE 4G

| LIGAND A | LIGAND B | LIGAND C | LIGAND D | EPITOPE OR REPORTER | LOCALIZATION SIGNAL |

FIGURE 5A

| LOCALIZATION SIGNAL | LIGAND X | LIGAND Y | EPITOPE OR REPORTER |

FIGURE 5B

| LIGAND X | SPACER | LIGAND X | EPITOPE OR REPORTER | LOCALIZATION SIGNAL |

FIGURE 5C

| LOCALIZATION SIGNAL | LIGAND X | SPACER | LIGAND Y | EPITOPE OR REPORTER |

FIGURE 5D

| EPITOPE OR REPORTER | LIGAND X | LIGAND Y | LIGAND B | LOCALIZATION SIGNAL |

FIGURE 5E

| LOCALIZATION SIGNAL | EPITOPE OR REPORTER | LIGAND A | SPACER | LIGAND B |

FIGURE 5F

| EPITOPE OR REPORTER | LIGAND B | LOCALIZATION SIGNAL |

FIGURE 5G

| LOCALIZATION SIGNAL | EPITOPE OR REPORTER | SPACER | LIGAND A | SPACER | LIGAND B |

FIGURE 5H

| LIGAND X | SPACER | LIGAND Z | SPACER | EPITOPE OR REPORTER | LOCALIZATION SIGNAL |

FIGURE 5I

| PROMOTER | LIGAND or POLYLIGAND | EPITOPE | LOCALIZATION SIGNAL | STOP | POLY-A |

FIGURE 6A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 6B

| PROMOTER | LIGAND or POLYLIGAND | REPORTER | LOCALIZATION SIGNAL | STOP | POLY-A |

FIGURE 6C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 6D

| PROMOTER | OPTIONAL EPITOPE | OPTIONAL REPORTER | OPTIONAL LOCALIZATION SIGNAL | LIGAND or POLYLIGAND | STOP | POLY-A |

FIGURE 6E

| Categories of Inhibition Strategies for PAI-1 Decoys ||
|---|---|
| Category | Inhibition Strategy |
| Latent State | The decoy favors shifting PAI1 into a latent state |
| Turn PAI1 into a substrate | The decoy either maintains PAI1 in a conformation that allows tPA to cleave it, or the decoy actively cleaves PAI1. |
| Steric hindrance to tPA binding | Provides some sort of steric barrier to the normal tPA/uPA interactions, through binding multiple PAI1 molecules or potentially interfering with the PAI1-tPA binding site. This could manifest as noncompetitive inhibition. |
| Steric hindrance to endogenous vitronectin | The use of the vitronectin PAI1-binding domain, separated from the rest of the molecule, will inhibit the native vitronectin action. Note that vitronectin binds PAI1, stabilizes it through the binding, and by its other domains assists in targeting it to its sites of action. The decoy vitronectin domain, lacking its other functional parts, will not assist in that natural targeting. Mutations in the decoy designs will also attempt to minimize the stabilizing effect of the binding. |
| Direct competition for binding site | Decoys that compete directly for PAI1 binding in a manner identical to that of tPA. |

FIGURE 16

| PROMOTER | PAI-1 cDNA (UV enabled) | STOP | POLY-A |

FIGURE 18A

| PROMOTER | PAI-1 cDNA (UV enabled) | DEGRON | STOP | POLY-A |

FIGURE 18B

| PROMOTER | DEGRON | PAI cDNA (UV enabled) | STOP | POLY-A |

FIGURE 18C

| PROMOTER | PAI-1 cDNA (UV enabled) | LOCALIZATION SIGNAL | STOP | POLY-A |

FIGURE 18D

| PROMOTER | LOCALIZATION SIGNAL | PAI-1 cDNA (UV enabled) | STOP | POLY-A |

FIGURE 18E

| PROMOTER | LOCALIZATION SIGNAL | PAI-1 cDNA (UV enabled) | DEGRON | STOP | POLY-A |

FIGURE 18F

| PROMOTER | PAI-1 cDNA (UV enabled) | LOCALIZATION SIGNAL | DEGRON | STOP | POLY-A |

FIGURE 18G

| PROMOTER | DEGRON | PAI-1 cDNA (UV enabled) | LOCALIZATION SIGNAL | STOP | POLY-A |

FIGURE 18H

| PROMOTER | DEGRON | LOCALIZATION SIGNAL | PAI-1 cDNA (UV enabled) | STOP | POLY-A |

FIGURE 18I

| PROMOTER | LIGAND or POLYLIGAND | STOP | POLY-A |

FIGURE 23A

| PROMOTER | LOCALIZATION SIGNAL | LIGAND OR POLYLIGAND | OPTIONAL DEGRON | STOP | POLY-A |

FIGURE 23B

| PROMOTER | LIGAND or POLYLIGAND | LOCALIZATION SIGNAL | OPTIONAL DEGRON | STOP | POLY-A |

FIGURE 23C

| PROMOTER | OPTIONAL DEGRON | LIGAND OR POLYLIGAND | LOCALIZATION SIGNAL | STOP | POLY-A |

FIGURE 23D

| PROMOTER | OPTIONAL DEGRON | LOCALIZATION SIGNAL | LIGAND OR POLYLIGAND | STOP | POLY-A |

FIGURE 23E

| PROMOTER | LOCALIZATION SIGNAL | LIGAND or POLYLIGAND | STOP | POLY-A |

FIGURE 23F

| PROMOTER | LIGAND or POLYLIGAND | LOCALIZATION SIGNAL | STOP | POLY-A |

FIGURE 23G

POLYNUCLEOTIDES ENCODING THERAPEUTIC INHIBITORS OF PAI-1

BACKGROUND OF THE INVENTION

1. Field of the Invention

The invention relates to modified PAI-1 proteins and nucleic acids. The invention also relates to mammalian PAI-1 ligands and modulators. In particular, the invention relates to polypeptides, polypeptide compositions and polynucleotides that encode polypeptides that are ligands and/or modulators of PAI-1. The invention also relates to polyligands that are homopolyligands or heteropolyligands that modulate PAI-1 activity. The invention also relates to ligands and polyligands localized to a region of a cell. The invention also relates to localization tethers and promoter sequences that can be used to provide spatial control of the PAI-1 ligands and polyligands. The invention also relates to inducible gene switches that can be used to provide temporal control of the PAI-1 ligands and polyligands. The invention also relates to methods of treating or preventing atherosclerosis. The invention also relates to methods of treating or preventing fibrosis.

2. Background of the Invention

Plasminogen activator inhibitor-1 (PAI-1) is a serine protease inhibitor of tissue plasminogen activator (tPA) and urokinase plasminogen activator (uPA), agents that convert the proenzyme plasminogen to the fibrinolytic enzyme plasmin. Regulation of fibrinolysis by PAI-1 is an important control point for normal vascular function, as the accumulation of fibrin can lead to blood clots, while an excessive decrease in fibrin can lead to hemorrhage. PAI-1 also plays an important role in tissue fibrosis by inactivating matrix metalloproteinases as well as plasmin generation (Takeshita, K, et al., American Journal of Physiology, 2004(2):449-456), and studies that modulated PAI-1 expression in animal models have implicated PAI-1 in the pathogenesis of fibrosis after chemical or immune-mediated injury (Weisberg. A D et al., Arterioscler. Thromb. Vasc. Biol., 2005, 25:365-371).

PAI-1 has also been implicated in the pathophysiology of renal, pulmonary, cardiovascular, and metabolic diseases (Cale, J M and Lawrence, D A. Curr Drug Targets, 2007, 8 (9):971-81), as well as cancer. A number of investigations have supported a role for PAI-1 in the development of heart disease. For example, pharmacologic inhibition of PAI-1 was demonstrated to protect against antiotensin-II-induced aortic remodeling (Weisberg. A D et al., Arterioscler. Thromb. Vasc. Biol., 2005, 25:365-371). Further, attenuated development of cardiac fibrosis was observed in PAI-deficient mice after myocardial infarction compared to wild-type (Takesita, K, et al., American Journal of Pathology, 2004, 164(2):449-455. Several studies (reviewed in Sobel, B E et al., Arterioscler. Thromb. Vasc. Biol., 2003, 23:1979-1989) suggest altered expression of PAI-1 in vessel walls might contribute to coronary atherogenesis.

New reagents and methods for manipulating PAI-1 expression in heart would advance research into its role in heart disease. Further, there is a need in this area for novel reagents, treatments, and methods for inhibiting PAI-1 activity.

SUMMARY OF THE INVENTION

One object of the invention is to provide mammalian PAI-1 ligands, polyligands, and/or modulators.

Another object of the invention is to provide mammalian PAI-1 ligands, polyligands, and/or modulators linked to a localization tether.

Another object of the invention is to provide mammalian PAI-1 ligands, polyligands, and/or modulators linked to a tissue-specific promoter.

Another object of the invention is to provide mammalian PAI-1 ligands, polyligands, and/or modulators linked to an inducible gene switch.

Another object of the invention is to provide a method for achieving spatial control of a mammalian PAI-1 ligand, polyligand, and/or modulator by linking the ligand, polyligand, and/or modulator to a localization tether or a tissue-specific promoter.

Another object of the invention is to provide a method for achieving temporal control of a mammalian PAI-1 ligand, polyligand, and/or modulator by linking the ligand, polyligand, and/or modulator to an inducible gene switch.

Another object of the invention is to provide localization tethers that can be used with a PAI-1 ligand, polyligand, and/or modulator to provide spatial control.

Another object of the invention is to provide tissue-specific promoters that can be used with a PAI-1 ligand, polyligand, and/or modulator to provide spatial control.

Another object of the invention is to provide inducible gene switches that can be used with a PAI-1 ligand, polyligand, and/or modulator to provide temporal control.

Another object of the invention is to provide polynucleotides encoding mammalian PAI-1 ligands, polyligands, and/or modulators.

Another object of the invention is to provide gene constructs comprising a polynucleotide encoding a mammalian PAI-1 ligand, polyligand, and/or modulator and a localization tether or tissue-specific promoter.

Another objection of the invention is to provide vectors comprising polynucleotides encoding mammalian PAI-1 ligands, polyligands, and/or modulators.

Another object of the invention is to provide host cells comprising polynucleotides encoding mammalian PAI-1 ligands, polyligands, and/or modulators.

Another object of the invention is to provide transgenic organisms comprising polynucleotides encoding mammalian PAI-1 ligands, polyligands, and/or modulators.

Another object of the invention is to provide methods of treating or preventing a cardiovascular disease using mammalian PAI-1 ligands, polyligands, and/or modulators.

Another object of the invention is to provide methods of treating or preventing a fibrotic condition using mammalian PAI-1 ligands, polyligands, and/or modulators.

Another object of the invention is a method for transferring a polynucleotide encoding a PAI-1 ligand, polyligand, and/or modulator to cardiovascular tissue.

Another embodiment of the invention is to provide a method for assessing the function of PAI-1 in the formation of unstable plaques.

Another object of the invention is to provide methods of treating or preventing atherosclerosis using monocytes modified to express an inhibitor of the fibrinolytic pathway.

Another object of the invention is to provide methods of treating or preventing a fibrotic condition using monocytes modified to express an inhibitor of the fibrinolytic pathway.

Another object of the invention is to provide a fusion protein comprising PAI-1 protein linked to a degron.

Another object of the invention is to provide a fusion protein comprising PAI-1 linked to a localization signal.

It is another object of the invention to provide a PAI-1 polynucleotide sequence that has been optimized for vector insertion.

Another object of the invention is to provide a PAI-1 polynucleotide sequence that has been optimized for vector insertion, that is optionally linked to a polynucleotide sequence encoding a degron.

Another object of the invention is to provide a PAI-1 polynucleotide sequence that has been optimized for vector insertion, that is optionally linked to a polynucleotide sequence encoding a localization signal.

Another object of the invention is to provide gene constructs containing a PAI-1 polynucleotide sequence that has been optimized for vector insertion, optionally linked to a polynucleotide sequence encoding a degron and/or a localization signal.

Another object of the invention is to provide vectors containing gene constructs containing a PAI-1 polynucleotide sequence that has been optimized for vector insertion, optionally linked to a polynucleotide sequence encoding a degron and/or a localization signal.

Another object of the invention is to provide host cells containing vectors containing gene constructs containing a PAI-1 polynucleotide sequence that has been optimized for vector insertion, optionally linked to a polynucleotide sequence encoding a degron and/or a localization signal.

Another object of the invention is to provide transgenic organisms containing a PAI-1 polynucleotide sequence that has been optimized for vector insertion, optionally linked to a polynucleotide sequence encoding a degron and/or a localization signal.

Another object of the invention is to provide gene constructs containing a PAI-1 polynucleotide sequence that has been optimized for vector insertion, optionally linked to a polynucleotide sequence encoding a degron and/or a localization signal, that include a ubiquitous, tissue-specific, cell-specific, or inducible promoter.

Another object of the invention is to provide vectors containing gene constructs containing a PAI-1 polynucleotide sequence that has been optimized for vector insertion, optionally linked to a polynucleotide sequence encoding a degron and/or a localization signal, that include a ubiquitous, tissue-specific, cell-specific, or inducible promoter.

Another object of the invention is to provide host cells containing vectors containing gene constructs containing a PAI-1 polynucleotide sequence that has been optimized for vector insertion, optionally linked to a polynucleotide sequence encoding a degron and/or a localization signal, that include a ubiquitous, tissue-specific, cell-specific, or inducible promoter.

Another object of the invention is to provide transgenic organisms containing gene constructs containing a PAI-1 polynucleotide sequence that has been optimized for vector insertion, optionally linked to a polynucleotide sequence encoding a degron and/or a localization signal, that include a ubiquitous, tissue-specific, cell-specific, or inducible promoter.

Another object of the invention is to provide a method of altering the expression of PAI-1 in a host cell.

Another object of the invention is to provide a method of altering expression of PAI-1 in heart tissue.

Another object of the invention is to provide a method of creating a transgenic subject with altered PAI-1 expression.

Another object of the invention is to provide mammalian PAI-1 ligands, polyligands, and/or modulators.

Another object of the invention is to provide mammalian PAI-1 ligands, polyligands, and/or modulators linked to a degron.

Another object of the invention is to provide mammalian PAI-1 ligands, polyligands, and/or modulators linked to a localization signal.

Another object of the invention is to provide polynucleotides encoding mammalian PAI-1 ligands, polyligands, and/or modulators, optionally linked to an epitope, reporter, degron and/or a localization signal.

Another object of the invention is to provide gene constructs containing polynucleotides encoding mammalian PAI-1 ligands, polyligands, and/or modulators, optionally linked to an epitope, reporter, degron and/or a localization signal.

Another object of the invention is to provide vectors containing gene constructs containing polynucleotides encoding mammalian PAI-1 ligands, polyligands, and/or modulators, optionally linked to an epitope, reporter, degron and/or a localization signal.

Another object of the invention is to provide host cells containing vectors containing gene constructs containing polynucleotides encoding mammalian PAI-1 ligands, polyligands, and/or modulators, optionally linked to an epitope, reporter, degron and/or a localization signal.

Another object of the invention is to provide transgenic organisms containing polynucleotides encoding mammalian PAI-1 ligands, polyligands, and/or modulators, optionally linked to an epitope, reporter, degron and/or a localization signal.

Another object of the invention is to provide gene constructs containing polynucleotides encoding mammalian PAI-1 ligands, polyligands, and/or modulators, optionally linked to an epitope, reporter, degron and/or a localization signal, that include a ubiquitous, tissue-specific, cell-specific, or inducible promoter.

Another object of the invention is to provide vectors containing gene constructs containing polynucleotides encoding mammalian PAI-1 ligands, polyligands, and/or modulators, optionally linked to an epitope, reporter, degron and/or a localization signal, that include a ubiquitous, tissue-specific, cell-specific, or inducible promoter.

Another object of the invention is to provide host cells containing vectors containing gene constructs containing polynucleotides encoding mammalian PAI-1 ligands, polyligands, and/or modulators, optionally linked to an epitope, reporter, degron and/or a localization signal, that include a ubiquitous, tissue-specific, cell-specific, or inducible promoter.

Another object of the invention is to provide transgenic organisms containing gene constructs containing polynucleotides encoding mammalian PAI-1 ligands, polyligands, and/or modulators, optionally linked to an epitope, reporter, degron and/or a localization signal, that include a ubiquitous, tissue-specific, cell-specific, or inducible promoter.

Another object of the invention is to provide methods of inhibiting PAI-1 in a host cell.

Another object of the invention is to provide methods of inhibiting PAI-1 in heart tissue.

Another object of the invention is to provide methods of creating a transgenic subject with reduced PAI-1 activity.

Description of Polypeptide and Polynucleotide Sequences

SEQ ID NOS:1-30 represent examples of PAI-1 ligands and polyligands and polynucleotides encoding them. A diagram of each of the following ligands and polyligands that shows the architecture of their individual peptide components is shown in FIG. 9.

Specifically, the PAI-1 polyligand of SEQ ID NO:1 is encoded by SEQ ID NO:2, wherein codons are optimized for mammalian expression and vector insertion. The PAI-1 polyligand of SEQ ID NO:1 is an embodiment of a homopolyligand and is known herein as PAI1-DCY-94-1.

The PAI-1 polyligand of SEQ ID NO:3 is encoded by SEQ ID NO:4, wherein codons are optimized for mammalian expression and vector insertion. The PAI-1 polyligand of SEQ ID NO:3 is an embodiment of a monomeric ligand and is also known herein as PAI1-DCY-94-2.

The PAI-1 polyligand of SEQ ID NO:5 is encoded by SEQ ID NO:6, wherein codons are optimized for mammalian expression and vector insertion. The PAI-1 polyligand of SEQ ID NO:5 is an embodiment of a homopolyligand and is also known herein as PAI1-DCY-94-3.

The PAI-1 polyligand of SEQ ID NO:7 is encoded by SEQ ID NO:8, wherein codons are optimized for mammalian expression and vector insertion. The PAI-1 polyligand of SEQ ID NO:7 is an embodiment of a heteropolyligand and is also known herein as PAI1-DCY-94-4.

The PAI-1 polyligand of SEQ ID NO:9 is encoded by SEQ ID NO:10, wherein codons are optimized for mammalian expression and vector insertion. The PAI-1 polyligand of SEQ ID NO:9 is an embodiment of a monomeric ligand and is also known herein as PAI1-DCY-94-5.

The PAI-1 polyligand of SEQ ID NO:11 is encoded by SEQ ID NO:12, wherein codons are optimized for mammalian expression and vector insertion. The PAI-1 polyligand of SEQ ID NO:11 is an embodiment of a monomeric ligand and is also known herein as PAI1-DCY-94-6.

The PAI-1 polyligand of SEQ ID NO:13 is encoded by SEQ ID NO:14, wherein codons are optimized for mammalian expression and vector insertion. The PAI-1 polyligand of SEQ ID NO:13 is an embodiment of a heteropolyligand and is also known herein as PAI1-DCY-94-7.

The PAI-1 polyligand of SEQ ID NO:15 is encoded by SEQ ID NO:16, wherein codons are optimized for mammalian expression and vector insertion. The PAI-1 polyligand of SEQ ID NO:15 is an embodiment of a heteropolyligand and is also known herein as PAI1-DCY-94-8.

The PAI-1 polyligand of SEQ ID NO:17 is encoded by SEQ ID NO:18, wherein codons are optimized for mammalian expression and vector insertion. The PAI-1 polyligand of SEQ ID NO:17 is an embodiment of a heteropolyligand and is also known herein as PAI1-DCY-94-9.

The PAI-1 polyligand of SEQ ID NO:19 is encoded by SEQ ID NO:20, wherein codons are optimized for mammalian expression and vector insertion. The PAI-1 polyligand of SEQ ID NO:19 is an embodiment of a heteropolyligand and is also known herein as PAI1-DCY-94-10.

The PAI-1 polyligand of SEQ ID NO:21 is encoded by SEQ ID NO:22, wherein codons are optimized for mammalian expression and vector insertion. The PAI-1 polyligand of SEQ ID NO:21 is an embodiment of a heteropolyligand and is also known herein as PAI1-DCY-94-11.

The PAI-1 polyligand of SEQ ID NO:23 is encoded by SEQ ID NO:24, wherein codons are optimized for mammalian expression and vector insertion. The PAI-1 polyligand of SEQ ID NO:23 is an embodiment of a heteropolyligand and is also known herein as PAI1-DCY-94-12.

The PAI-1 polyligand of SEQ ID NO:25 is encoded by SEQ ID NO:26, wherein codons are optimized for mammalian expression and vector insertion. The PAI-1 polyligand of SEQ ID NO:25 is an embodiment of a heteropolyligand and is also known herein as PAI1-DCY-94-13.

The PAI-1 polyligand of SEQ ID NO:27 is encoded by SEQ ID NO:28, wherein codons are optimized for mammalian expression and vector insertion. The PAI-1 polyligand of SEQ ID NO:27 is an embodiment of a heteropolyligand and is also known herein as PAI1-DCY-94-14.

The PAI-1 polyligand of SEQ ID NO:29 is encoded by SEQ ID NO:30, wherein codons are optimized for mammalian expression and vector insertion. The PAI-1 polyligand of SEQ ID NO:29 is an embodiment of a heteropolyligand and is also known herein as PAI1-DCY-94-15.

SEQ ID NOS:31-36 represent examples of full length proteins used to construct ligands and polyligands. SEQ ID NO:31 is known as *Homo sapiens* plasminogen activator inhibitor 1 and has the public accession number AAA60009. SEQ ID NO:32 is known as *Homo sapiens* vitronectin and has the public accession number EAW51082. SEQ ID NO:33 is known as *Homo sapiens* kallikrein 2, prostatic isoform 1 and has the public accession number NP_005542. SEQ ID NO:34 is known as *Homo sapiens* tissue plasminogen activator and has the public accession number BAA00881. SEQ ID NO:35 is known as *Homo sapiens* toll-like receptor 3 and has the public accession number NP_003256. SEQ ID NO:36 is known as *Homo sapiens* urokinase plasminogen activator (uPA) and has the public accession number CAA01390.

SEQ ID NOS:37-51 represent examples of monomeric ligand peptides. Each of SEQ ID NOS:37-51 is represented in FIG. 9 with the name or abbreviated name of the parent protein, followed by the amino acid range of the parent protein that it represents, followed by any amino acid substitution mutation indicated by the convention: X#Z, where X is the one letter amino acid code of the amino acid to be replaced, # is the amino acid residue position or number within the parent protein, and Z is the one letter amino acid code of the new substituting amino acid.

SEQ ID NO:37 is a partial sequence of SEQ ID NO:31 and is represented in FIG. 9 as 'PAI1 354-368'.

SEQ ID NO:38 is a partial sequence of SEQ ID NO:31 and is represented in FIG. 9 as 'PAI1 300-309'.

SEQ ID NO:39 is a partial sequence of SEQ ID NO:31 and is represented in FIG. 9 as 'PAI1 343-353'.

SEQ ID NO:40 is a partial sequence of SEQ ID NO:32 and is represented in FIG. 9 as 'vitronectin 20-63'.

SEQ ID NO:41 is a partial sequence of SEQ ID NO:32 that comprises a F32L substitution mutation and is represented in FIG. 9 as 'vitronectin 20-63 F32L'.

SEQ ID NO:42 is a partial sequence of SEQ ID NO:32 that comprises a T29A substitution mutation and is represented in FIG. 9 as 'vitronectin 20-63 T29A'.

SEQ ID NO:43 is a partial sequence of SEQ ID NO:32 that comprises a E42A substitution mutation and is represented in FIG. 9 as 'vitronectin 20-63 E42a'.

SEQ ID NO:44 is a partial sequence of SEQ ID NO:32 that comprises a L43A substitution mutation and is represented in FIG. 9 as 'vitronectin 20-63 L43A'.

SEQ ID NO:45 is a partial sequence of SEQ ID NO:45 that comprises S23F, T52E, D53L, A56Y, and E57Y substitution mutations and is represented in FIG. 9 as 'vitronectin 20-63 mutant'.

SEQ ID NO:46 is a partial sequence of SEQ ID NO:33 and is represented in FIG. 9 as 'Kallikrein 2 (25-256)'.

SEQ ID NO:47 is a partial sequence of SEQ ID NO:33 and is represented in FIG. 9 as hK2 (25-44).

SEQ ID NO:48 is a partial sequence of SEQ ID NO:33 and is represented in FIG. 9 as 'Kallikrein 2 (47-256)'.

SEQ ID NO:49 is a partial sequence of SEQ ID NO:34 and is represented in FIG. 9 as 'tPA (301-308)'.

SEQ ID NO:50 is a partial sequence of SEQ ID NO:35 that comprises V55A, N57Y, T59N, S79K, D81K, and G83E substitution mutations and is represented in FIG. 9 as 'Toll like receptor 3 29-121 (V55A, N57Y, T59N, S79K, D81K, G83E)'.

SEQ ID NO:51 is a partial sequence of SEQ ID NO:36 that comprises H224A, D275A, and S376A substitution mutations and is represented in FIG. 9 as 'Urokinase Plasminogen Activator (179-415) H224A, D275A, S376A'.

SEQ ID NO:52 represents an example of a full-length protein used to create a natural spacer fragment. SEQ ID NO:52 is known as *Humicola insolens* exoglucanase-6A precursor (Exocellobiohydrolase 6A) (1,4-beta-cellobiohydrolase 6A) (Beta-glucancellobiohydrolase 6A) (Avicelase 2) and has the public accession number Q9C1S9.

SEQ ID NO:53 represents an example of a natural spacer fragment. SEQ ID NO:53 is a partial sequence of SEQ ID NO:52, and is represented in FIG. 9 as '16aa linker'.

SEQ ID NOS:54-56 represent examples of artificial spacers.

SEQ ID NOS:57-76 represent examples of class 1 localization tether polypeptides useful in the present invention. A diagram of each of the following class 1 localization tether polypeptides that shows the architecture of their individual peptide components is shown in FIGS. 14A-14B.

The class 1 localization tether of SEQ ID NO:57 is also known herein as 91-1.
The class 1 localization tether of SEQ ID NO:58 is also known herein as 91-2.
The class 1 localization tether of SEQ ID NO:59 is also known herein as 91-3.
The class 1 localization tether of SEQ ID NO:60 is also known herein as 91-4.
The class 1 localization tether of SEQ ID NO:61 is also known herein as 91-5.
The class 1 localization tether of SEQ ID NO:62 is also known herein as 91-6.
The class 1 localization tether of SEQ ID NO:63 is also known herein as 91-7.
The class 1 localization tether of SEQ ID NO:64 is also known herein as 91-8.
The class 1 localization tether of SEQ ID NO:65 is also known herein as 91-9.
The class 1 localization tether of SEQ ID NO:66 is also known herein as 91-10.
The class 1 localization tether of SEQ ID NO:67 is also known herein as 91-11.
The class 1 localization tether of SEQ ID NO:68 is also known herein as 91-12.
The class 1 localization tether of SEQ ID NO:69 is also known herein as 91-13.
The class 1 localization tether of SEQ ID NO:70 is also known herein as 91-14.
The class 1 localization tether of SEQ ID NO:71 is also known herein as 91-15.
The class 1 localization tether of SEQ ID NO:72 is also known herein as 91-16.
The class 1 localization tether of SEQ ID NO:73 is also known herein as 91-17.
The class 1 localization tether of SEQ ID NO:74 is also known herein as 91-18.
The class 1 localization tether of SEQ ID NO:75 is also known herein as 91-19.
The class 1 localization tether of SEQ ID NO:76 is also known herein as 91-20.

SEQ ID NOS:77-95 represent examples of polypeptide fragments used to construct class 1 localization tethers.

SEQ ID NO:96 represents an example of an epitope tag used as internal cargo to construct class 1 localization tethers, and is represented in FIGS. 14A-14B as 'TAG'.

SEQ ID NOS:97-99 represent examples of spacers used to construct class 1 localization tethers.

SEQ ID NOS:100-111 represent examples of class 3 localization tether polypeptides useful in the present invention. A diagram of each of the following class 3 localization tether polypeptides that shows the architecture of their individual peptide components is shown in FIG. 15.

The class 3 localization tether of SEQ ID NO:100 is also known herein as 93-1.
The class 3 localization tether of SEQ ID NO:101 is also known herein as 93-2.
The class 3 localization tether of SEQ ID NO:102 is also known herein as 93-3.
The class 3 localization tether of SEQ ID NO:103 is also known herein as 93-4.
The class 3 localization tether of SEQ ID NO:104 is also known herein as 93-5.
The class 3 localization tether of SEQ ID NO:105 is also known herein as 93-6.
The class 3 localization tether of SEQ ID NO:106 is also known herein as 93-7.
The class 3 localization tether of SEQ ID NO:107 is also known herein as 93-8.
The class 3 localization tether of SEQ ID NO:108 is also known herein as 93-9.
The class 3 localization tether of SEQ ID NO:109 is also known herein as 93-10.
The class 3 localization tether of SEQ ID NO:110 is also known herein as 93-11.
The class 3 localization tether of SEQ ID NO:111 is also known herein as 93-12.

SEQ ID NOS:112-129 represent examples of polypeptide fragments used to construct class 3 localization tethers.

SEQ ID NO:130 represents an example of an epitope tag used as internal cargo to construct class 3 localization tethers, and is represented in FIG. 15 as 'TAG' or 'TAG/IC'.

SEQ ID NO:131 represents an example of a synthetic TACE/ADAM17 cut site used to construct class 3 localization tethers.

SEQ ID NOS:132-139 represent examples of tissue specific promoter sequences useful in the present invention.

SEQ ID NO:132 is an example of an arterial smooth muscle-specific promoter and is also known herein as MOD 5306, the structure of which is depicted schematically in FIG. 10.

SEQ ID NO:133 is an example of a synthetic vascular smooth muscle cell-specific promoter and is also known herein as MOD 5309, the structure of which is depicted schematically in FIG. 11A.

SEQ ID NO:134 is an example of a synthetic vascular smooth muscle cell-specific promoter and is also known herein as MOD 5312, the structure of which is depicted schematically in FIG. 11B.

SEQ ID NO:135 is an example of a synthetic vascular smooth muscle cell-specific promoter and is also known herein as MOD 5315, the structure of which is depicted schematically in FIG. 11C.

SEQ ID NO:136 is an example of a endothelial cell-specific promoter and is also known herein as MOD 4012-ESM1, the structure of which is depicted schematically in FIG. 12A.

SEQ ID NO:137 is an example of a endothelial cell-specific promoter and is also known herein as MOD 4399-FLT1, the structure of which is depicted schematically in FIG. 12B.

SEQ ID NO:138 is an example of a synthetic endothelial cell-specific promoter and is also known herein as MOD 4790, the structure of which is depicted schematically in FIG. 13A.

SEQ ID NO:139 is an example of a synthetic endothelial cell-specific promoter and is also known herein as MOD 4791, the structure of which is depicted schematically in FIG. 13B.

Three letter amino acid codes and one letter amino acid codes are used herein as is commonly known in the art.

DESCRIPTION OF THE DRAWINGS

Figure 4G:
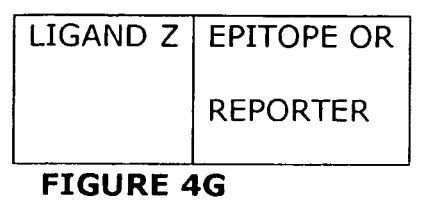

FIGS. 4A-4G show examples of polyligands linked to epitopes or reporters.

FIGS. 5A-5I show examples of polyligands linked to localization signals and epitopes or reporters.

FIGS. 6A-6E show examples of gene constructs that include a ligand or polyligand optionally linked to an epitope, reporter, and/or a localization signal.

FIG. 16 shows exemplary inhibition mechanisms of PAI-1 ligands and polyligands.

FIGS. 18A-18I show examples of gene constructs that include an ULTRAVECTOR (UV)-enabled PAI-1 cDNA, optionally linked to a degron and/or a localization signal.

FIGS. 23A-23G show examples of gene constructs that include a ligand or polyligand optionally linked to a degron and/or a localization signal.

DETAILED DESCRIPTION OF THE INVENTION

Figure 1A:
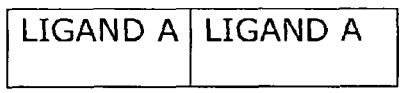
FIGS. 1A-1F show examples of homopolyligands with or without spacers.
Figure 1B:
Figure 1C:
Figure 1D:
Figure 1E:
Figure 1F:
Figure 2A:
FIGS. 2A-2J show examples of heteropolyligands with or without spacers.
Figure 2B:
Figure 2C:
Figure 2D:
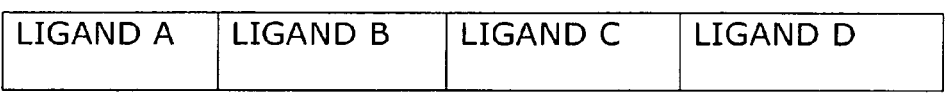
Figure 2E:
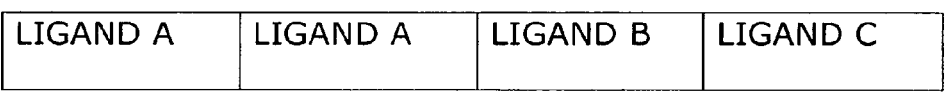
Figure 2F:
Figure 2G:
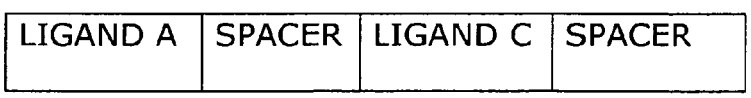
Figure 2H:
Figure 2I:
Figure 2J:
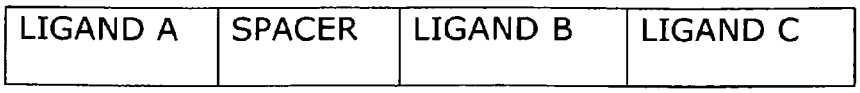
Figure 3A:
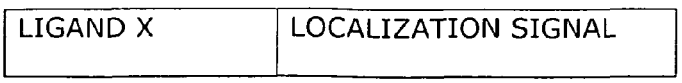
FIGS. 3A-3H show examples of ligands and polyligands linked to localization signals.
Figure 3B:
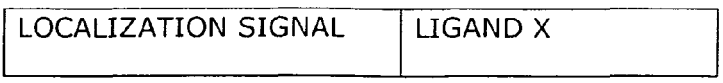
Figure 3C:
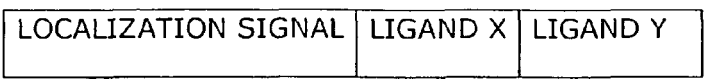
Figure 3D:
Figure 3E:
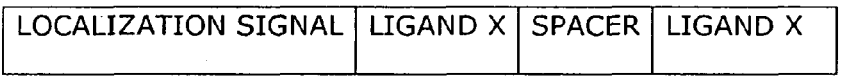
Figure 3F:
Figure 3G:
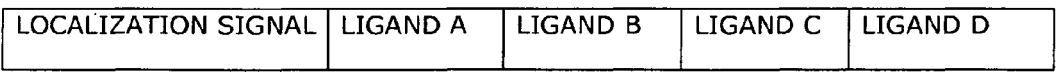
Figure 3H:
Figure 4A:
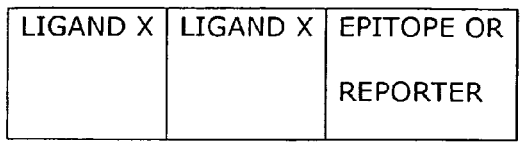
Figure 4B:
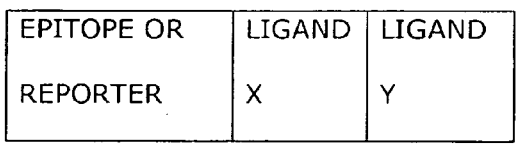
Figure 4C:
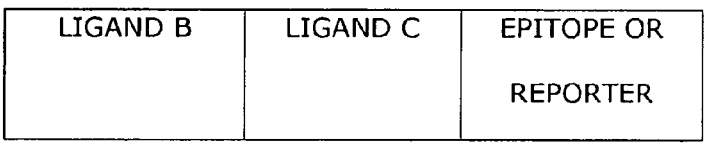
Figure 4D:
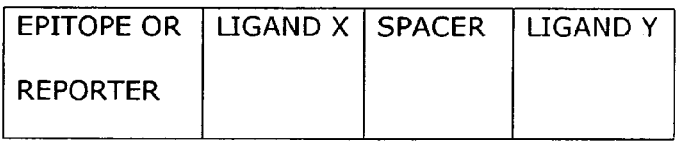
Figure 4E:
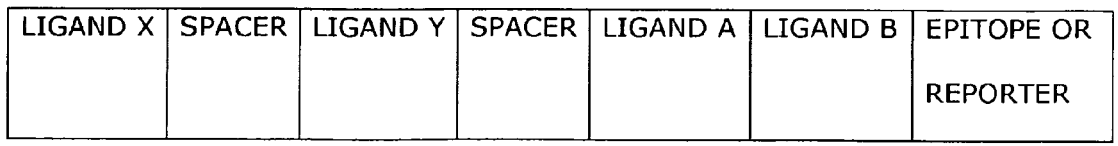
Figure 4F:
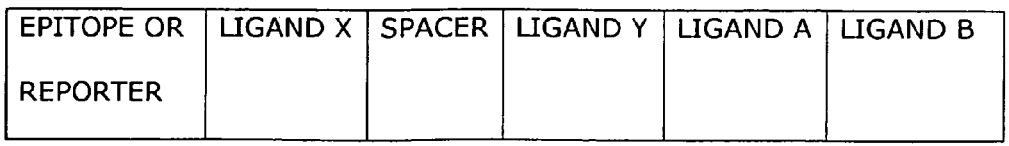

Terms used in the specification and claims have ordinary meanings understood in the art. For example, polynucleotide is used interchangeably with nucleic acid and includes single or double stranded DNA, RNA and polymeric analogs thereof.

The term chimeric means comprised of fragments that are not contiguous in their natural state. For example, a chimeric polynucleotide means a polynucleotide comprising fragments that are not contiguous in their natural state.

The terms polypeptide, peptide, and protein are used interchangeably and represent polymers of amino acids.

A synthetic gene (or portion of a gene) is a non-natural gene (or portion of a gene) that differs from a wildtype polynucleotide sequence. A synthetic gene (or portion of a gene) may contain one or more nucleic acid sequences not contiguous in nature (chimeric sequences), and/or may encompass substitutions, insertions, and deletions and combinations thereof.

A non-human organism encompasses, non-human primates, mammals, vertebrates, invertebrates, plants, and lower eukaryotic organisms including yeast and slime molds.

Restriction endonucleases are enzymes that cleave nucleic acids at recognition sequences within a nucleic acid molecule.

Host cells include but are not limited to commercial and non-commercial cell lines, such as those available from the ATCC (Manassas, Va.), primary cell cultures, stem cells, immune cells, blood cells, cells from any organism or tissue.

A vector refers to any vehicle for the cloning of and/or transfer of a nucleic acid into a host cell. A vector may be a replicon to which another DNA segment may be attached so as to bring about the replication of the attached segment. A replicon refers to any genetic element (e.g., plasmid, phage, cosmid, chromosome, virus) that functions as an autonomous unit of DNA replication in vivo, i.e., capable of replication under its own control. The term vector includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the present invention is the UltraVector™ Production System (Intrexon Corp., Blacksburg, Va.) as described in WO 2007/038276, incorporated herein by reference. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term plasmid refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A cloning vector refers to a replicon which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another (shuttle vector). Cloning vectors may comprise one or more sequences that can be used for selection of cells comprising the vector and/or one or more multiple cloning sites for insertion of sequences of interest.

The term expression vector refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); Beta-lactamase, lac, ara, tet, trp, 1PL, 1PR, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, beta-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell beta-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., J. Biol. Chem. 267:963 (1992); Wu et al., J. Biol. Chem. 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al., Proc. Natl. Acad. Sci. USA. 84:7413 (1987); Mackey et al., Proc. Natl. Acad. Sci. USA 85:8027 (1988); and Ulmer et al., Science 259:1745 (1993)). The use of cationic lipids may promote encapsulation of negatively charged nucleic acids, and also promote fusion with negatively charged cell membranes (Feigner et al., Science 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., Hum. Gene Ther. 3:147 (1992); and Wu et al., J. Biol. Chem. 262:4429 (1987)).

The term transfection refers to the uptake of exogenous or heterologous RNA or DNA by a cell. A cell has been transfected by exogenous or heterologous RNA or DNA when such RNA or DNA has been introduced inside the cell. A cell has been transformed by exogenous or heterologous RNA or DNA when the transfected RNA or DNA effects a phenotypic change. The transforming RNA or DNA can be integrated (covalently linked) into chromosomal DNA making up the genome of the cell.

Transformation refers to the transfer of a nucleic acid fragment into the genome of a host organism, resulting in genetically stable inheritance. Host organisms containing the transformed nucleic acid fragments are referred to as transgenic or recombinant or transformed organisms.

In addition, the recombinant vector comprising a polynucleotide according to the invention may include one or more origins for replication in the cellular hosts in which their amplification or their expression is sought, markers or selectable markers.

The term selectable marker refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term reporter gene refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), fluorescent proteins such as green fluorescent protein (GFP), chloramphenicol acetyltransferase (CAT), beta-galactosidase (LacZ), beta-glucuronidase (Gus), and the like. Selectable marker genes may also be considered reporter genes.

Promoter and promoter sequence are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as constitutive promoters. Promoters that cause a gene to be expressed in a specific cell type are commonly referred to as cell-specific promoters or tissue-specific promoters. Promoters that cause a gene to be expressed at a specific stage of development or cell differentiation are commonly referred to as developmentally-specific promoters or cell differentiation-specific promoters. Promoters that are induced and cause a gene to be expressed following exposure or treatment of the cell with an agent, biological molecule, chemical, ligand, light, or the like that induces the promoter are commonly referred to as inducible promoters or regulatable promoters. It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The term homology refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term homologous in all its grammatical forms and spelling variations refers to the relationship between proteins that possess a common evolutionary origin, including proteins from superfamilies (e.g., the immunoglobulin superfamily) and homologous proteins from different species (e.g., myosin light chain, etc.) (Reeck et al., Cell 50:667 (1987)). Such proteins (and their encoding genes) have sequence homology, as reflected by their high degree of sequence similarity. However, in common usage and in the present application, the term homologous, when modified with an adverb such as highly, may refer to sequence similarity and not a common evolutionary origin.

Accordingly, the term sequence similarity in all its grammatical forms refers to the degree of identity or correspondence between nucleic acid or amino acid sequences of proteins that may or may not share a common evolutionary origin (see Reeck et al., Cell 50:667 (1987)). In one embodiment, two DNA sequences are substantially homologous or substantially similar when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, substantially similar refers to nucleic acid fragments wherein changes in one or more nucleotide bases results in substitution of one or more amino acids, but do not affect the functional properties of the protein encoded by the DNA sequence. Substantially similar also refers to nucleic acid fragments wherein changes in one or more nucleotide bases do not affect the ability of the nucleic acid fragment to mediate alteration of gene expression by antisense or co-suppression technology. Substantially similar also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the present invention are those nucleic acid fragments whose DNA sequences are at least about 70%, 80%, 90% or 95% identical to the DNA sequence of the nucleic acid fragments reported herein.

The term corresponding to is used herein to refer to similar or homologous sequences, whether the exact position is identical or different from the molecule to which the similarity or homology is measured. A nucleic acid or amino acid sequence alignment may include spaces. Thus, the term corresponding to refers to the sequence similarity, and not the numbering of the amino acid residues or nucleotide bases.

A substantial portion of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., J. Mol. Biol. 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20 to 30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 to 15 bases may be used as amplification primers in PCR in order to obtain a particular nucleic acid fragment comprising the primers. Accordingly, a substantial portion of a nucleotide sequence comprises enough of the sequence to specifically identify and/or isolate a nucleic acid fragment comprising the sequence.

One aspect of the invention is to provide a PAI-1 protein that is linked to a degron. A degron may be linked at the amino terminus of the PAI-1 protein or its carboxy terminus. Degrons, or degradation-determining signals are known in the art as short, often portable elements that induce polypeptide degradation, several examples of which are recited in Garcin, D, et al., Journal of Virology, 2004, 78(16):8799-8811 and Gardner, R G and Hampton, R Y, The EMBO Journal, 1999, 18(21):5994-6004. Examples of PAI-1 linked to a degron are shown in FIGS. 17A, 17B, 17E, 17F, 17G, and 17H.

Another aspect of the invention is to provide a PAI-1 protein that is linked to a localization signal. Non-limiting examples of cellular localization signals are signals that localize to the sarcoplasmic reticulum, endoplasmic reticulum, extracellular matrix, mitochondria, golgi apparatus, peroxisomes, lysosomes, nucleus, nucleolus, endosomes, exosomes, other intracellular vesicles, plasma membrane, apical membrane, and basolateral membrane. In one embodiment, PAI-1 is delivered to the extracellular face through non-cell-specific plasma membrane localization signals such as those described in U.S. Provisional Application 60/957,328. In other embodiments, PAI-1 is delivered to the extracellular face to cell-specific localization signals such as localization signals specific for fibroblasts, endothelial cells, smooth muscle cells, adipocytes, and the sarcolemma of cardiomyocytes. In other embodiments, PAI-1 is delivered to the extracellular matrix through extracellular association domains such as collagen binding proteins, or to other extracellular components enriched in myocardial infarct regions. FIGS. 17C-17H show additional embodiments of PAI-1 linked to localization signals. The localization signals are given by way of example and without limitation.

One aspect of the invention is to provide a PAI-1 polynucleotide sequence that has been optimized for vector insertion. In one embodiment, the polynucleotides are optimized for insertion into an ULTRAVECTOR (Intrexon Corp. Blacksburg, Va., US2004/0185556) plasmid vector. In another embodiment, the polynucleotides are optimized for vector insertion through removal of the following internal restriction sites: NgoM IV, Xma I, Cla I, BamH I, BstB I, EcoR I, RcoR V, Pci I, Sac I, Stu I, ApaL I, Bgl II, Kpn I, Mfe I, Nde I, Nhe I, Nsi I, Asc I, AsiS I, BsiW I, Fse I, Mlu I, Not I, Pac I, Sal I, Sbf I, SnaB I, Swa I, Rsr III, RsrII2, BstX I, Sap I, BsmB I, Xba I, Xho I, Hpa I, Pml I, Sph I, Aar I, Bgl I, BsmB I, BspM I, BstAP I, BstX I, Dra III, Ear I, Sap I, Bip I, and BspE I.

One aspect of the invention is to provide a PAI-1 polynucleotide sequence that has been optimized for vector insertion, that is linked to a degron polynucleotide sequence. In one embodiment, the degron sequence is linked at the 5' end of a PAI-1 polynucleotide sequence (see FIGS. 18C and 18H for examples). In another embodiment of the invention, the degron sequence is linked at the 3' end of a degron polynucleotide sequence (see FIGS. 18B and 18F for examples).

Another aspect of the invention is to provide a PAI-1 polynucleotide sequence that has been optimized for vector insertion, that is linked to a localization signal (see FIGS. 18D-18I for examples).

Another embodiment of the invention relates to gene constructs for selective control of expression of a vector insertion-optimized PAI-1 polynucleotide sequence in a desired cell, tissue, or physiological state. The gene constructs may include a PAI-1 gene construct optionally linked to a degron and/or a localization signal. Exemplary gene constructs are shown in FIGS. 13A-13E, 23A-23G, and 18A-18I. The promoter portion of the gene construct can be a constitutive promoter, a non-constitutive promoter, a tissue-specific promoter (constitutive or non-constitutive) or an inducible promoter. Non-limiting examples of tissue-specific promoters useful for the present invention are endothelial cell-specific promoters (White, S J, et al., Gene Ther. 2007 Nov. 8 [Epub ahead of print]), vascular smooth muscle cell-specific promoters (Ribault, S, Circ Res., 2001, 88(5):468-75; Appleby, C E, et al., Gene Ther. 2003, 10(18):1616-22), cardiomyocyte-specific promoters (Xu, L, et al., J Biol. Chem., 2006, 281(45):34430-40), coronary adipocytes-specific promoters, and cardiac fibroblast-specific promoters. Combined tissue and state specific promoters such as a cardiac and hypoxia-specific promoter (Su, H, et al., Proc Natl. Acad. Sci. U.S.A., 2004, 101(46):16280-5) are also useful for the present invention. Inducible promoters are activated by drugs or other factors. RHEOSWITCH is an inducible promoter system available from New England BioLabs (Ipswich, Mass.) that is useful for the present invention. An embodiment of the invention comprises a PAI-1 gene construct whose expression is controlled by an inducible promoter system.

Another aspect of the invention is to provide vectors containing gene constructs for expression of a mammalian cell expression and vector insertion-optimized PAI-1 polynucleotide sequence as described herein. Vectors may be viral vectors or non-viral vectors as described herein. Non-limiting examples of such vectors are shown in FIGS. 19A-19D.

Figure 19A:
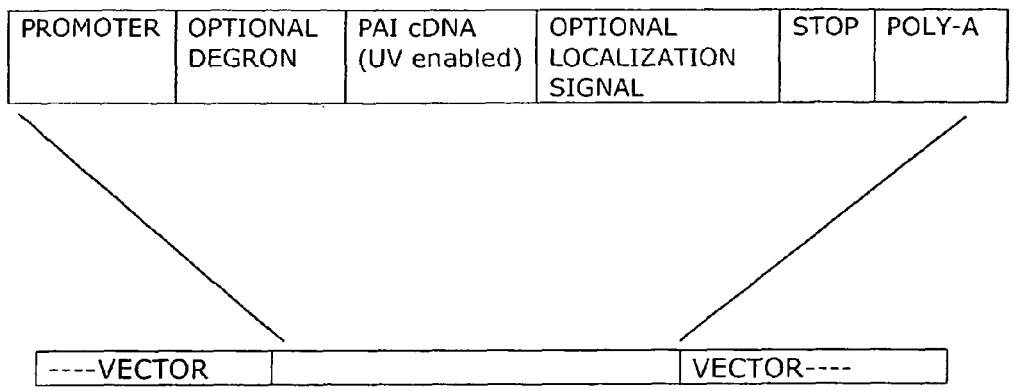
FIGS. 19A-19D show examples of vectors that contain ULTRAVECTOR (UV)-enabled PAI-1 gene constructs.

FIG. 19A shows in generic form a vector containing a vector insertion-optimized PAI-1 polynucleotide sequence and optional localization signal and/or degron, wherein the gene construct is releasable from the vector as a unit useful for generating transgenic animals. For example, the gene construct, or transgene, is released from the vector backbone by restriction endonuclease digestion. The released transgene is then injected into pronuclei of fertilized mouse eggs; or the transgene is used to transform embryonic stem cells. The vector of FIG. 19A is also useful for transient transfection of the transgene, wherein the promoter and codons of the transgene are optimized for mammalian expression.

Figure 19B:
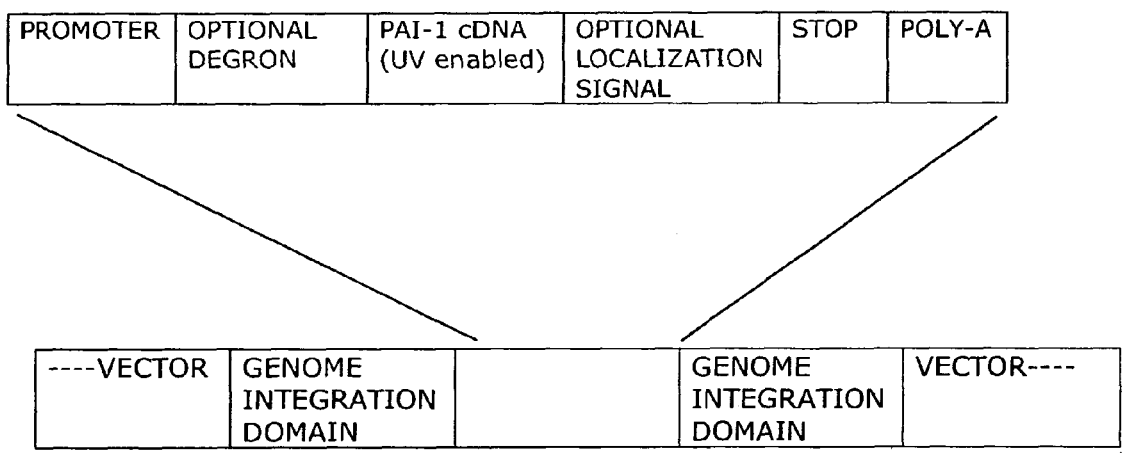
Figure 19C:
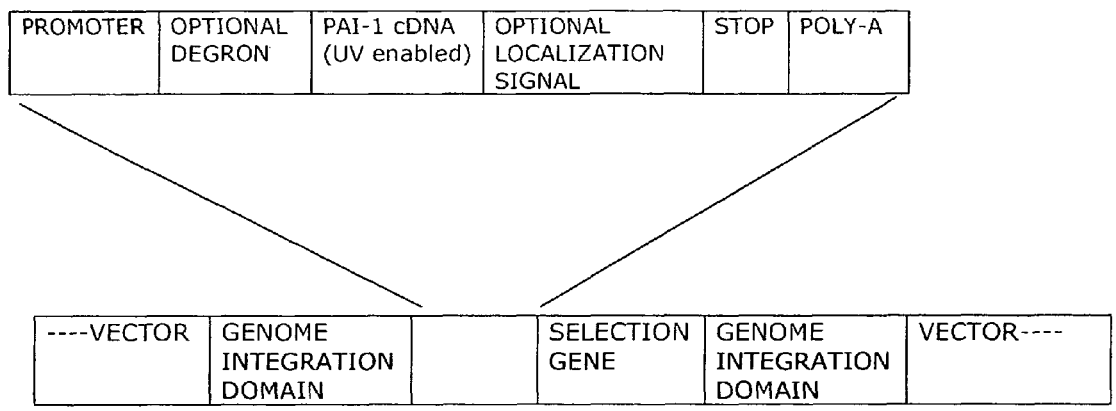

FIGS. 19B and 19C depict embodiments of gene therapy vectors for delivering and controlling PAI-1 polypeptide expression in vivo. Polynucleotide sequences linked to the gene construct in FIGS. 19B and 19C include genome integration domains to facilitate integration of the transgene into a viral genome and/or host genome.

Figure 19D:
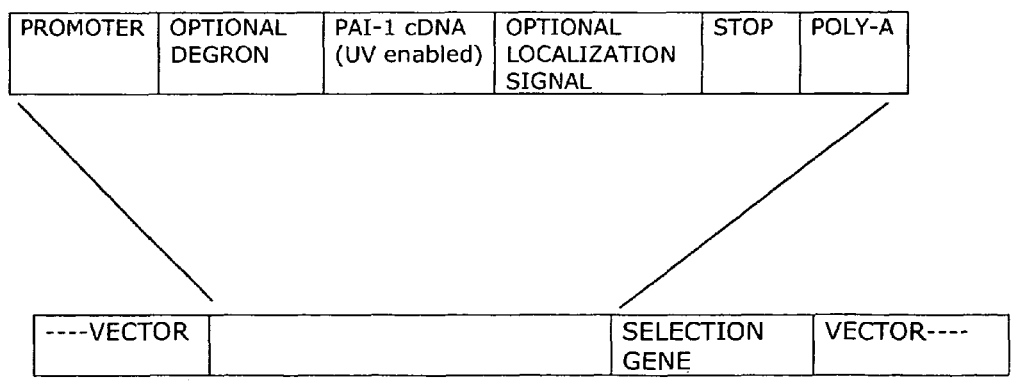
Figure 20A:
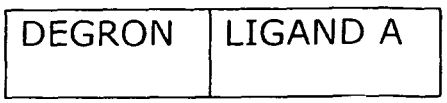
FIGS. 20A-20J show examples of ligands and homopolyligands with or without spacers linked to degrons.
Figure 20B:
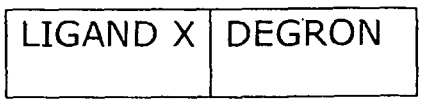
Figure 20C:
Figure 20D:
Figure 20E:
Figure 20F:
Figure 20G:
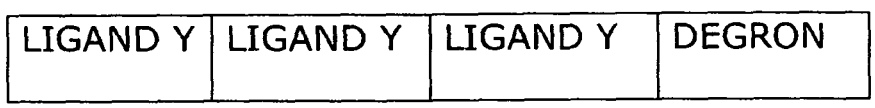
Figure 20H:
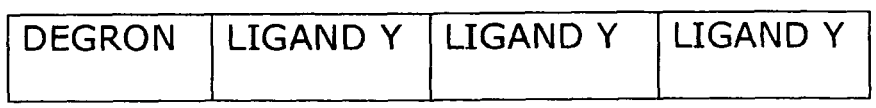
Figure 20I:
Figure 20J:
Figure 21A:
FIGS. 21A-21H show examples of heteropolyligands with or without spacers linked to degrons.
Figure 21B:
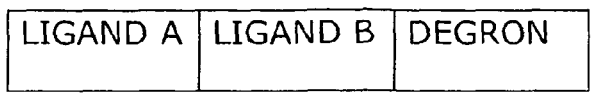
Figure 21C:
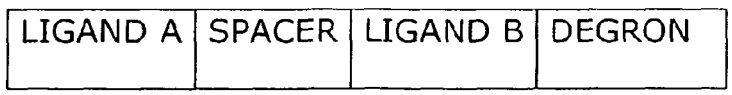
Figure 21D:
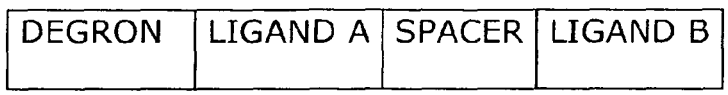
Figure 21E:
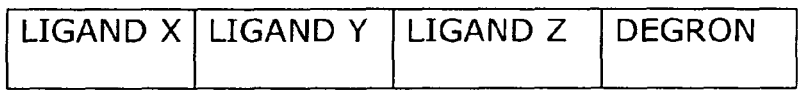
Figure 21F:
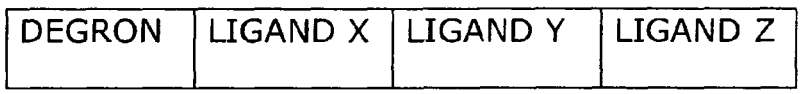
Figure 21G:
Figure 21H:
Figure 22A:
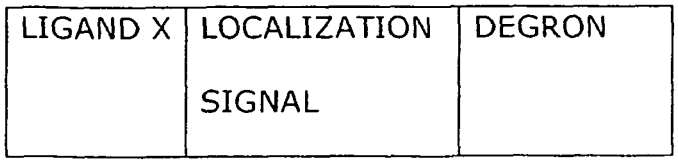
FIGS. 22A-22F show examples of ligands and polyligands linked to degrons and localization signals.
Figure 22B:
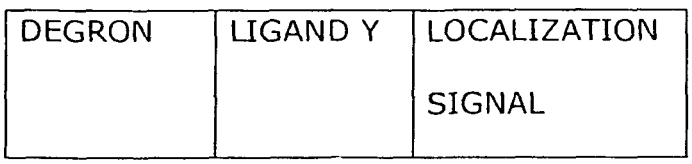
Figure 22C:
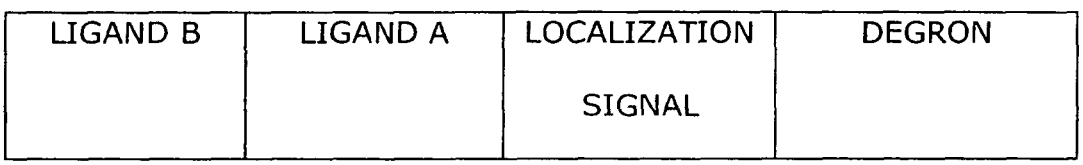
Figure 22D:
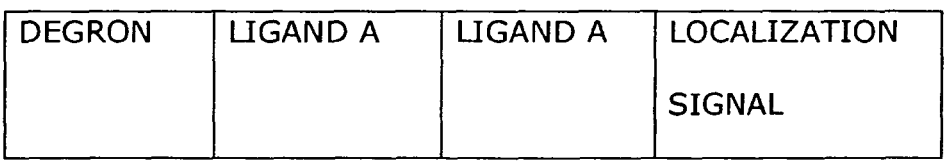
Figure 22E:
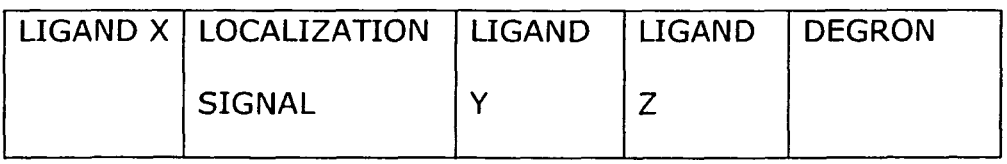
Figure 22F:
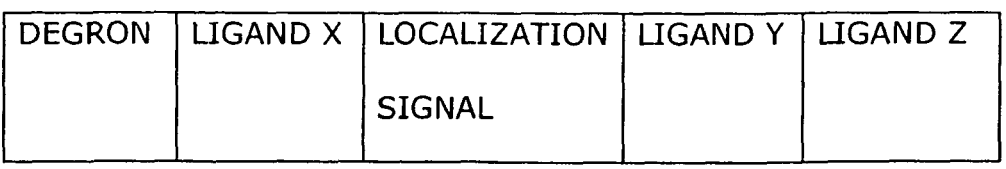

FIG. 19D shows a vector containing a localization signal gene construct useful for generating stable cell lines.

Another aspect of the invention is to provide host cells containing vectors containing gene constructs for expression of a mammalian cell expression and vector insertion-optimized PAI-1 polynucleotide sequence as described herein. In one embodiment, the host cells are mammalian cells. Host cells include human, non-human primate, mouse, bovine, porcine, ovine, equine, rat, rabbit, dog, cat, and guinea pig. Specific types of host cells include cardiomyocytes, fibroblasts, endothelial cells, smooth muscle cells, and adipocytes.

Another aspect of the invention is to provide transgenic organisms containing a mammalian cell expression and vector insertion-optimized PAI-1 polynucleotide sequence. In one embodiment, the transgenic host is mammalian. Mammalian transgenic hosts include non-human primate, mouse, cow, pig, sheep, horse, rat, rabbit, dog, cat, and guinea pig. Transgenic organisms are generated by injecting a completed transgene into the pronuclei of fertilized oocytes or into embryonic stem cells. The completed transgene includes the mammalian cell expression and vector insertion-optimized PAI-1 polynucleotide sequence, optionally linked to degrons, localization signals, or a constitutive promoter, a non-constitutive promoter, a tissue-specific promoter (constitutive or non-constitutive) or an inducible promoter as described herein. The transgenic organisms may be used as animal models to define the role of PAI-1 in the heart.

Another aspect of the invention is a method of altering expression of PAI-1 in a host cell comprising transfecting a vector comprising a vector insertion optimized-nucleic acid molecule encoding at least one copy of PAI-1 into a host cell and culturing the transfected host cell under conditions suitable to produce at least one copy of PAI-1.

Another aspect of the invention is a method of altering expression of PAI-1 in heart tissue of a subject comprising injecting a vector comprising a vector insertion optimized-nucleic acid molecule encoding at least one copy of PAI-1 into heart tissue of a subject.

Another aspect of the invention is a method of creating a transgenic subject with altered PAI-1 expression comprising injecting a vector comprising a vector insertion optimized-nucleic acid molecule encoding at least one copy of PAI-1 into a fertilized egg or an embryonic stem cell.

An aspect of the invention is to provide novel ligand inhibitors of PAI-1 activity by modifying a natural substrate and/or regulator by truncation and/or by amino acid substitution.

Another aspect of the invention is to provide modular polyligand inhibitors of PAI-1 activity by linking together novel inhibitors and variations thereof. A further aspect of the invention is to limit the activity of a PAI-1 inhibitor, ligand, or polyligand by linkage to a degron. A further aspect of the invention is the cellular localization of a PAI-1 inhibitor, ligand, or polyligand by linkage to a localization signal.

An aspect of the invention encompasses inhibition of PAI-1 as a way to prevent fibrosis in cardiac tissue. By inhibiting PAI-1, inhibition of plasminogen activators will be relieved, resulting in activation of plasminogen to plasmin and the breakdown of fibrin. Enhancement of fibrin breakdown of a diseased heart represents a potential approach for treating or preventing cardiomyopathies due to type II diabetes, hyperglycemia, hypertension, obesity, tobacco exposure, or other causes.

Additional aspects of the invention encompass PAI-1 inhibitors useful in any tissue.

Additional embodiments of the invention encompass PAI-1 inhibitors localized to different cellular locations by linking to a localization signal targeted to a region of a cell.

The invention relates to polypeptide ligands and polyligands for PAI-1. Various embodiments of PAI-1 ligands and polyligands are represented in SEQ ID NOS:1-30 and SEQ ID NOS:37-51. More specifically, the invention relates to ligands, homopolyligands, and heteropolyligands that comprise any one or more of SEQ ID NOS:37-51. Additionally, the invention relates to ligands and polyligands comprising one or more partial sequences (truncation fragments) of SEQ ID NOS:31-36 or any portion thereof. Furthermore, the invention relates to polyligands with at least about 80%, 85%, 90%, 95%, 96%, 97%, 98% and 99% sequence identity to a polyligand comprising one or more of SEQ ID NOS:37-51 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NOS:31-36.

Polyligands, which can be homopolyligands or heteropolyligands, are chimeric ligands composed of two or more monomeric polypeptide ligands. Examples of homopolyligands are shown in FIGS. 4A-4F. Examples of heteropolyligands are shown in FIGS. 6A-6J. An example of a monomeric ligand is the polypeptide represented by SEQ ID NO:40. SEQ ID NO:40 is a selected partial sequence of parental full length SEQ ID NO:32. An example of a homopolyligand is a polypeptide comprising a dimer or multimer of SEQ ID NO:37. An example of a heteropolyligand is a polypeptide comprising SEQ ID NO:37 and one or more of SEQ ID NOS:38-51. Each of SEQ ID NOS:37-51 represents an individual polypeptide ligand in monomeric form. SEQ ID NOS:37-51 are selected examples of partial sequences of SEQ ID NOS:31-36, however, other partial sequences of SEQ ID NOS:31-36 may also be utilized as monomeric ligands. Monomeric partial sequences of SEQ ID NOS:31-36 may be identical to a portion of a parent polypeptide, such as SEQ ID NO:40. Additionally, monomeric partial sequences of SEQ ID NOS:31-36 may have amino acid substitutions, such as SEQ ID NOS:41-45. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:37-51. Furthermore, monomeric ligands and polyligands may have at least about 80%, 85%, 90%, 95%, 96%, 97%, 98% and 99% sequence identity to a partial sequence of SEQ ID NOS:31-36.

There are numerous ways to combine SEQ ID NOS:37-51 into homopolymeric or heteropolymeric ligands. Furthermore, there are numerous ways to combine additional partial sequences of SEQ ID NOS:31-36 with each other and with SEQ ID NOS:37-51 to make polymeric ligands. Non-limiting examples of homopolyligand architectures are shown in FIGS. 1A-1F. Non-limiting examples of heteropolyligand architectures are shown in FIGS. 2A-2J. The instant invention is directed to all possible combinations of homopolyligands and heteropolyligands without limitation. The ligands and polyligands of the invention are designed to modulate the endogenous effects of PAI-1.

In one embodiment of the invention, the ligand or polyligand is a PAI-1 ligand or polyligand described herein.

In another embodiment of the invention, the ligand or polyligand is at least 60%, 65%, 70%, 75%, 80%, 85%, 90% 95%, 96%, 97%, 98% or 99% identical to a PAI-1 ligand or polyligand described herein.

In another embodiment of the invention, the ligand or polyligand is a PAI-1 ligand or polyligand described herein that has been modified to comprise one or more amino acid deletions, substitutions, insertions, truncations, or combinations thereof.

Another embodiment of the invention is a polypeptide at least 60%, 65%, 70%, 75%, 80%, 85%, 90% 95%, 96%, 97%, 98% or 99% identical to a polypeptide shown in the odd SEQ ID NOS of SEQ ID NOS:1-30.

Another embodiment of the invention is a polynucleotide at least 60%, 65%, 70%, 75%, 80%, 85%, 90% 95%, 96%, 97%, 98% or 99% identical to a polynucleotide shown in the even SEQ ID NOS of SEQ ID NOS:1-30.

In another embodiment of the invention, the PAI-1 ligand or polyligand comprises at least one peptide at least 60%, 65%, 70%, 75%, 80%, 85%, 90% 95%, 96%, 97%, 98% or 99% identical to one of SEQ ID NOS:37-51.

In another embodiment of the invention, the PAI-1 ligand or polyligand possesses at least one of the following inhibition mechanisms: latent state, turn PA1 into a substrate, steric hindrance to tPA binding, steric hindrance to endogenous vitronectin, or direct competition for binding site.

Another embodiment of the invention is a polynucleotide encoding a PAI-1 ligand or polyligand described herein.

The polyligands of the invention optionally comprise spacer amino acids before, after, or between monomers (see FIGS. 1D-1F and FIGS. 2F-2J for exemplary architectures).

This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands. The term ligand also encompasses the terms decoy, inhibitor, and modulator.

A monomeric ligand is a polypeptide where at least a portion of the polypeptide is capable of being recognized by PAI-1. The portion of the polypeptide capable of recognition is termed the recognition motif In the present invention, recognition motifs can be natural or synthetic. Examples of recognition motifs are well known in the art and include, but are not limited to, naturally occurring PAI-1 substrates, pseudosubstrate motifs, and interaction domains present in PAI-1 regulatory binding proteins and modifications thereof.

In general, ligand monomers based on natural PAI-1 interaction partners are built by identifying and isolating a putative PAI-1 interaction domain recognition motif. Exemplary natural PAI-1 interaction partners are known in the art and include fibrin, tissue plasminogen activator (the protein represented by SEQ ID NO:34), urokinase plasminogen activator (the protein represented by SEQ ID NO:36), and vitronectin (the protein represented by SEQ ID NO:32). Additional monomers include the PAI-1 recognition motif as well as amino acids adjacent and contiguous on either side of the PAI-1 interaction domain recognition motif. Monomeric ligands may therefore be any length provided the monomer includes the PAI-1 recognition motif For example, the monomer may comprise a PAI-1 recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 100 or more amino acids adjacent to the recognition motif. Further design considerations are taken from three-dimensional modeling of the ligands and modeling of binding interactions with PAI-1. Modifications of the primary sequence of a ligand or polyligand may be desirable based upon such modeling.

For example, in one embodiment, the invention comprises an inhibitor of PAI-1 comprising at least one copy of a peptide selected from the group consisting of:

a) a peptide at least 60%, 65%, 70%, 75%, 80%, 85%, 90%, 95%, 96%, 97%, 98% or 99% identical to a peptide comprising amino acid residues corresponding to amino acid residues 354-368 of SEQ ID NO:31;

b) a peptide at least 60%, 65%, 70%, 75%, 80%, 85%, 90%, 95%, 96%, 97%, 98% or 99% identical to a peptide comprising amino acid residues corresponding to amino acid residues 300-309 of SEQ ID NO:31;

c) a peptide at least 60%, 65%, 70%, 75%, 80%, 85%, 90%, 95%, 96%, 97%, 98% or 99% identical to a peptide comprising amino acid residues corresponding to amino acid residues 343-353 of SEQ ID NO:31;

d) a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32;

e) a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32, wherein the amino acid residue corresponding to amino acid residue 32 of SEQ ID NO:32 has been mutated from phenylalanine to leucine;

a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32, wherein the amino acid residue corresponding to amino acid residue 29 of SEQ ID NO:32 has been mutated from threonine to alanine;

g) a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32, wherein the amino acid residue corresponding to amino acid residue 42 of SEQ ID NO:32 has been mutated from glutamic acid to alanine;

h) a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32, wherein the amino acid residue corresponding to amino acid residue 43 of SEQ ID NO:32 has been mutated from leucine to alanine;

i) a peptide at least 60%, 65%, 70%, 75%, 80%, 85%, 90%, 95%, 96%, 97%, 98% or 99% identical to a peptide comprising amino acid residues corresponding to amino acid residues 20-63 of SEQ ID NO:32, wherein the amino acid residue corresponding to amino acid residue 23 of SEQ ID NO:32 has been mutated from serine to phenylalanine, the amino acid residue corresponding to amino acid residue 52 of SEQ ID NO:32 has been mutated from threonine to glutamic acid, the amino acid residue corresponding to amino acid residue 53 of SEQ ID NO:32 has been mutated from aspartic acid to leucine, the amino acid residue corresponding to amino acid residue 56 of SEQ ID NO:32 has been mutated from alanine to tyrosine, and the amino acid residue corresponding to amino acid residue 57 of SEQ ID NO:32 has been mutated from glutamic acid to tyrosine j) a peptide at least 60%, 65%, 70%, 75%, 80%, 85%, 90%, 95%, 96%, 97%, 98% or 99% identical to a peptide comprising amino acid residues corresponding to amino acid residues 25-256 of SEQ ID NO:33;

k) a peptide at least 60%, 65%, 70%, 75%, 80%, 85%, 90%, 95%, 96%, 97%, 98% or 99% identical to a peptide comprising amino acid residues corresponding to amino acid residues 25-44 of SEQ ID NO:33;

l) a peptide at least 60%, 65%, 70%, 75%, 80%, 85%, 90%, 95%, 96%, 97%, 98% or 99% identical to a peptide comprising amino acid residues corresponding to amino acid residues 47-256 of SEQ ID NO:33;

m) a peptide at least 60%, 65%, 70%, 75%, 80%, 85%, 90%, 95%, 96%, 97%, 98% or 99% identical to a peptide comprising amino acid residues corresponding to amino acid residues 301-308 of SEQ ID NO:34;

n) a peptide at least 60%, 65%, 70%, 75%, 80%, 85%, 90%, 95%, 96%, 97%, 98% or 99% identical to a peptide comprising amino acid residues corresponding to amino acid residues 29-121 of SEQ ID NO:35; wherein the amino acid residue corresponding to amino acid residue 55 of SEQ ID NO:35 has been mutated from valine to alanine, the amino acid residue corresponding to amino acid residue 57 of SEQ ID NO:35 has been mutated from asparagine to tyrosine, the amino acid residue corresponding to amino acid residue 59 of SEQ ID NO:35 has been mutated from threonine to asparagine, the amino acid residue corresponding to amino acid residue 79 of SEQ ID NO:35 has been mutated from serine to lysine, the amino acid residue corresponding to amino acid residue 81 of SEQ ID NO:35 has been mutated from aspartic acid to lysine, and the amino acid residue corresponding to amino acid residue 83 of SEQ ID NO:35 has been mutated from glycine to glutamic acid; and o) a peptide at least 60%, 65%, 70%, 75%, 80%, 85%, 90%, 95%, 96%, 97%, 98% or 99% identical to a peptide comprising amino acid residues corresponding to amino acid residues 179-415 of SEQ ID NO:36; wherein the amino acid residue corresponding to amino acid residue 224 of SEQ ID NO:36 has been mutated from histidine to alanine, the amino acid residue corresponding to amino acid residue 275 of SEQ ID NO:36 has been mutated from aspartic acid to alanine, and the amino acid residue corresponding to amino acid residue 376 of SEQ ID NO:36 has been mutated from serine to alanine.

As used herein, the terms "correspond(s) to" and "corresponding to," as they relate to sequence alignment, are intended to mean enumerated positions within a reference protein, e.g., (plasminogen activator inhibitor 1, AAA60009, SEQ ID NO:31), and those positions that align with the positions on the reference protein. Thus, when the amino acid sequence of a subject peptide is aligned with the amino acid sequence of a reference peptide, e.g., SEQ ID NO:31, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

In other embodiments, a ligand may be a monoclonal antibody fragment, a phage-display product, a PAI-1 synthesis inhibitor, or a transcription factor decoy.

A monomeric ligand is a polypeptide where at least a portion of the polypeptide is capable of being recognized by PAI-1. The portion of the polypeptide capable of recognition is termed the recognition motif. In the present invention, recognition motifs can be natural or synthetic. Examples of recognition motifs are well known in the art and include, but are not limited to, naturally occurring PAI-1 substrates, pseudosubstrate motifs, and interaction domains present in PAI-1 regulatory binding proteins and modifications thereof.

A polymeric ligand (polyligand) comprises two or more monomeric ligands.

A homopolymeric ligand is a polymeric ligand where each of the monomeric ligands is identical in amino acid sequence, except that a dephosphorylatable residue, such as serine, threonine, or tyrosine, may be substituted or modified in one or more of the monomeric ligands. Modifications include, but are not limited to, substitution to a pseudophosphorylated residue (acidic amino acid) or substitution to a neutral residue.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

Additional embodiments of the invention include monomers (as described above) based on any putative or real interaction partner for PAI-1. Furthermore, if the substrate or binding protein has more than one recognition motif, then more than one monomer may be identified therein.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting PAI-1 in a host cell comprising transfecting a vector comprising a nucleic acid molecule encoding at least one copy of a ligand or polyligand into a host cell and culturing the transfected host cell under conditions suitable to produce at least one copy of the ligand or polyligand.

Another aspect of the invention is a method of inhibiting PAI-1 in heart tissue of a subject comprising injecting a vector comprising a nucleic acid molecule encoding at least one copy of a PAI-1 ligand or polyligand into heart tissue of a subject.

Another aspect of the invention is a method of creating a transgenic subject with reduced PAI-1 activity comprising injecting a vector comprising a nucleic acid molecule encoding at least one copy of a PAI-1 ligand or polyligand into a fertilized egg or an embryonic stem cell.

The invention also relates to modified inhibitors that are at least about 60%, 65%, 70%, 75%, 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring PAI-1 recognition motif that has been modified by addition, deletion, or substitution of one or more amino acids in the primary structure (amino acid sequence) of the motif The terms "protein" and "polypeptide" and "peptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Sometimes it is desirable to employ proline in a spacer for the purpose of interrupting secondary structure of a polypeptide. Spacer amino acids may be any amino acid and are not limited to alanine, glycine and proline. Exemplary spacers are provided in SEQ ID NOS:53-56. The instant invention is directed to all combinations of homopolyligands and heteropolyligands, with or without spacers, and without limitation to the examples given above or below.

The ligands and polyligands of the invention are optionally linked to signals that localize the ligand to a region of a cell. Non-limiting examples of cellular localization signals are signals that localize to the sarcoplasmic reticulum, endoplasmic reticulum, extracellular matrix, mitochondria, golgi apparatus, peroxisomes, lysosomes, nucleus, nucleolus, endosomes, exosomes, other intracellular vesicles, plasma membrane, apical membrane, and basolateral membrane. In one embodiment, the ligands and polyligands are delivered to the extracellular face through non-cell-specific plasma membrane localization signals such as those described in U.S. Provisional Application 60/957,328. In other embodiments, the ligands and polyligands are delivered to the extracellular face to cell-specific localization signals such as localization signals specific for fibroblasts, endothelial cells, smooth muscle cells, adipocytes, and the sarcolemma of cardiomyocytes. In other embodiments, the ligands and polyligands are delivered to the extracellular matrix through extracellular association domains such as collagen binding proteins, or to other extracellular components enriched in myocardial infarct regions. FIGS. 3A-3H, 5A-5I, 11A-11I and 22A-22F show exemplary architectures of ligands and polyligands linked to localization signals. The localization signals are given by way of example and without limitation.

One embodiment of the invention is a ligand or polyligand linked to a class 1 localization tether.

Another embodiment of the invention is a ligand or polyligand linked to a class 2 localization tether.

Another embodiment of the invention a ligand or polyligand linked to a class 3 localization tether.

Another embodiment of the invention is a class 1 localization tether described herein.

Another embodiment of the invention is a class 1 localization tether at least 60%, 65%, 70%, 75%, 80%, 85%, 90% 95%, 96%, 97%, 98% or 99% identical to a class 1 localization tether described herein.

Another embodiment of the invention is a class 1 localization tether described herein that has been modified to comprise one or more amino acid deletions, substitutions, insertions, truncations, or combinations thereof.

Another embodiment of the invention is a class 1 localization tether at least 60%, 65%, 70%, 75%, 80%, 85%, 90% 95%, 96%, 97%, 98% or 99% identical to SEQ ID NOS:57-76.

Another embodiment of the invention is a class 1 localization tether comprising at least one peptide at least 60%, 65%, 70%, 75%, 80%, 85%, 90% 95%, 96%, 97%, 98% or 99% identical to one of SEQ ID NOS:77-95.

Another embodiment of the invention is a polynucleotide that encodes a class 1 localization tether described herein.

Another embodiment of the invention is a class 2 localization tether described herein.

Another embodiment of the invention is a polynucleotide that encodes a class 2 localization tether described herein.

Another embodiment of the invention is a class 3 localization tether described herein.

Another embodiment of the invention is a class 3 localization tether at least 60%, 65%, 70%, 75%, 80%, 85%, 90% 95%, 96%, 97%, 98% or 99% identical to a class 3 localization tether described herein.

Another embodiment of the invention is a class 3 localization tether described herein that has been modified to comprise one or more amino acid deletions, substitutions, insertions, truncations, or combinations thereof.

Another embodiment of the invention is a class 3 localization tether at least 60%, 65%, 70%, 75%, 80%, 85%, 90% 95%, 96%, 97%, 98% or 99% identical to SEQ ID NOS:100-111.

Another embodiment of the invention is a class 3 localization tether comprising at least one peptide at least 60%, 65%, 70%, 75%, 80%, 85%, 90% 95%, 96%, 97%, 98% or 99% identical to one of SEQ ID NOS:112-128.

Another embodiment of the invention is a polynucleotide that encodes a class 3 localization tether described herein.

The ligands and polyligands of the invention may also be linked to degrons to restrict their activity. FIGS. 21A-21H and 22A-22F show several non-limiting embodiments of ligands and polyligands linked to degrons.

Further, the ligands and polyligands of the invention are optionally linked to additional molecules or amino acids that provide an epitope tag or a reporter (see FIGS. 4A-4G). Non-limiting examples of epitope tags are FLAG™, HA (hemagluttinin), c-Myc and His6. Non-limiting examples of reporters are alkaline phosphatase, galactosidase, peroxidase, luciferase and fluorescent proteins. The epitopes and reporters are given by way of example and without limitation. The epitope tag and/or reporter may be the same molecule. The epitope tag and/or reporter may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, reporter, or degron to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics.

FIGS. 6A-6E, 13A-13E and 23A-23G show examples of PAI-1 ligand-containing gene constructs. PAI-1 ligand-containing gene constructs may be delivered via viral or nonviral vectors as described herein. FIGS. 7B and 7C depict embodiments of gene therapy vectors for delivering and controlling polypeptide expression in vivo. Polynucleotide sequences linked to the gene constructs in FIGS. 7B and 7C include genome integration domains to facilitate integration of the transgene into a viral genome and/or host genome. AttP and AttB sequences are non-limiting examples of genome integration sequences.

Figure 7A:
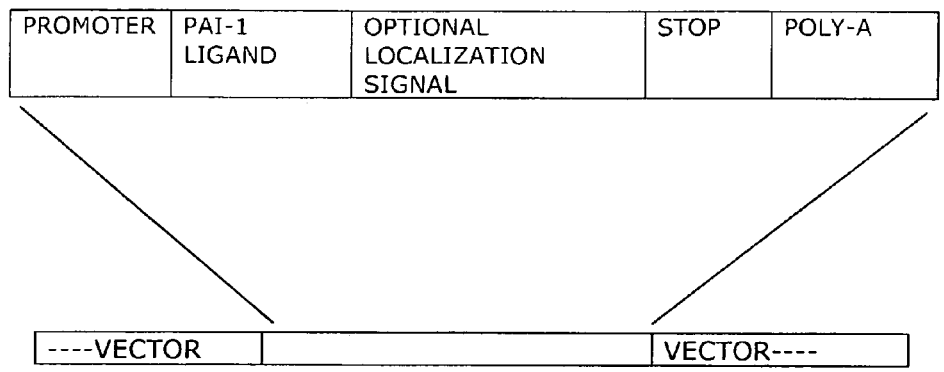
FIGS. 7A-7D show examples of vectors containing ligand gene constructs.
Figure 7B:
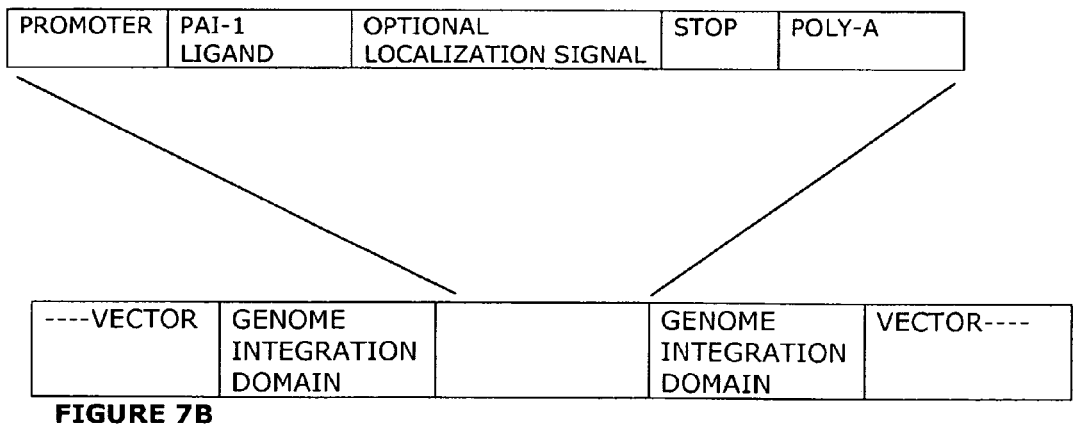
Figure 7C:
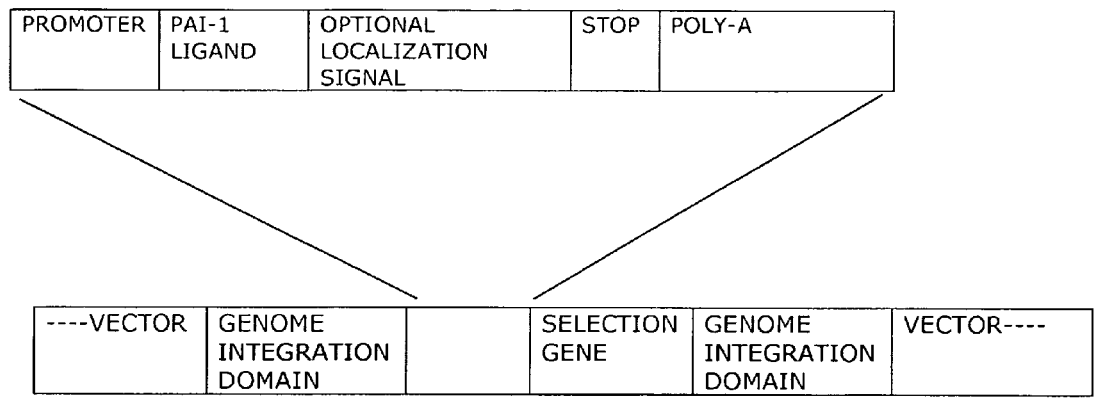

FIG. 7A shows a vector containing a PAI-1 ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 7A is also useful for transient transfection of the transgene, wherein the promoter and codons of the transgene are optimized for the host organism. The vector containing a ligand gene construct of FIG. 7A is also useful for recombinant expression of polypeptides in fermentable organisms adaptable for small or large scale production, wherein the promoter and codons of the transgene are optimized for the fermentation host organism.

Figure 7D:
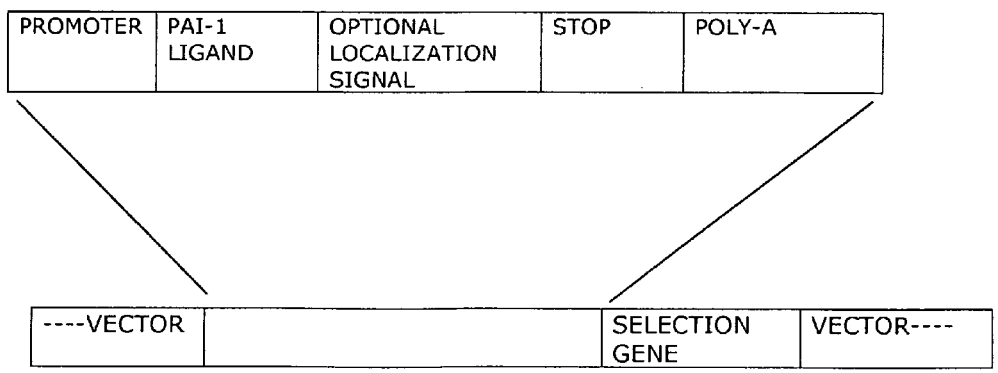

FIG. 7D shows a vector containing a PAI-1 ligand gene construct useful for generating stable cell lines.

The invention also encompasses polynucleotides comprising nucleotide sequences encoding ligands and polyligands. The polynucleotides of the invention are optionally linked to additional nucleotide sequences encoding degrons, localization signals, epitopes, or reporters. Further, the nucleic acids of the invention are optionally incorporated into vector polynucleotides. The polynucleotides are optionally flanked by nucleotide sequences comprising restriction endonuclease sites and other nucleotides needed for restriction endonuclease activity. The flanking sequences optionally provide cloning sites within a vector. The restriction sites can include, but are not limited to, any of the commonly used sites in most commercially available cloning vectors. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without degrons, localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealed. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to gene constructs for selective control of PAI-1 ligand or polyligand expression in a desired cell, tissue, or physiological state. Exemplary gene constructs architectures are shown in FIGS. 6A-6E. The promoter portion of the gene construct can be a constitutive promoter, a non-constitutive promoter, a tissue-specific promoter (constitutive or non-constitutive) or an inducible promoter. Non-limiting examples of tissue-specific promoters useful for the present invention are endothelial cell-specific promoters (White, S J, et al., Gene Ther. 2007 Nov. 8 [Epub ahead of print]), vascular smooth muscle cell-specific promoters (Ribault, S, Circ Res., 2001, 88(5):468-75; Appleby, C E, et al., Gene Ther. 2003, 10(18):1616-22), cardiomyocyte-specific promoters (Xu, L, et al., J Biol. Chem., 2006, 281(45):34430-40), coronary adipocytes-specific promoters, and cardiac fibroblast-specific promoters. Combined tissue and state specific promoters such as a cardiac and hypoxia-specific promoter (Su, H, et al., Proc Natl Acad Sci USA, 2004, 101(46):16280-5) are particularly useful for the present invention as they would allow expression of the ligand or polyligand in myocardial infarct regions. Inducible promoters are activated by drugs or other factors. RHEOSWITCH is an inducible promoter system available from New England BioLabs (Ipswich, Mass.) that is useful for the present invention. An embodiment of the invention comprises a ligand or polyligand gene construct whose expression is controlled by an inducible promoter system.

One embodiment of the invention is a polynucleotide encoding a ligand or polyligand linked to a tissue-specific promoter.

Another embodiment of the invention is a polynucleotide encoding a ligand or polyligand linked to an arterial smooth muscle specific-promoter.

Another embodiment of the invention is a polynucleotide encoding a ligand or polyligand linked to a vascular smooth muscle cell-specific promoter.

Another embodiment of the invention is a polynucleotide encoding a ligand or polyligand linked to an endothelial cell-specific promoter.

Another embodiment of the invention is a polynucleotide encoding a ligand or polyligand linked to a synthetic endothelial cell-specific promoter.

Another embodiment of the invention is a polynucleotide encoding a tissue-specific promoter described herein.

Another embodiment of the invention is a polynucleotide encoding a tissue-specific promoter described herein that has been modified to comprise one or more nucleotide deletions, substitutions, insertions, truncations, or combinations thereof.

Another embodiment of the invention is a polynucleotide encoding a tissue-specific promoter that is at least 60%, 65%, 70%, 75%, 80%, 85%, 90%, 95%, 96%, 97%, 98%, or 99% identical to a tissue-specific promoter described herein.

Another embodiment of the invention is a polynucleotide at least 60%, 65%, 70%, 75%, 80%, 85%, 90%, 95%, 96%, 97%, 98%, or 99% identical to a polynucleotide shown in SEQ ID NOS:132-139.

Polyligands are modular in nature. An aspect of the instant invention is the combinatorial modularity of the disclosed polyligands. Another aspect of the invention are methods of making these modular polyligands easily and conveniently.

In this regard, an embodiment of the invention comprises methods of modular cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 8:
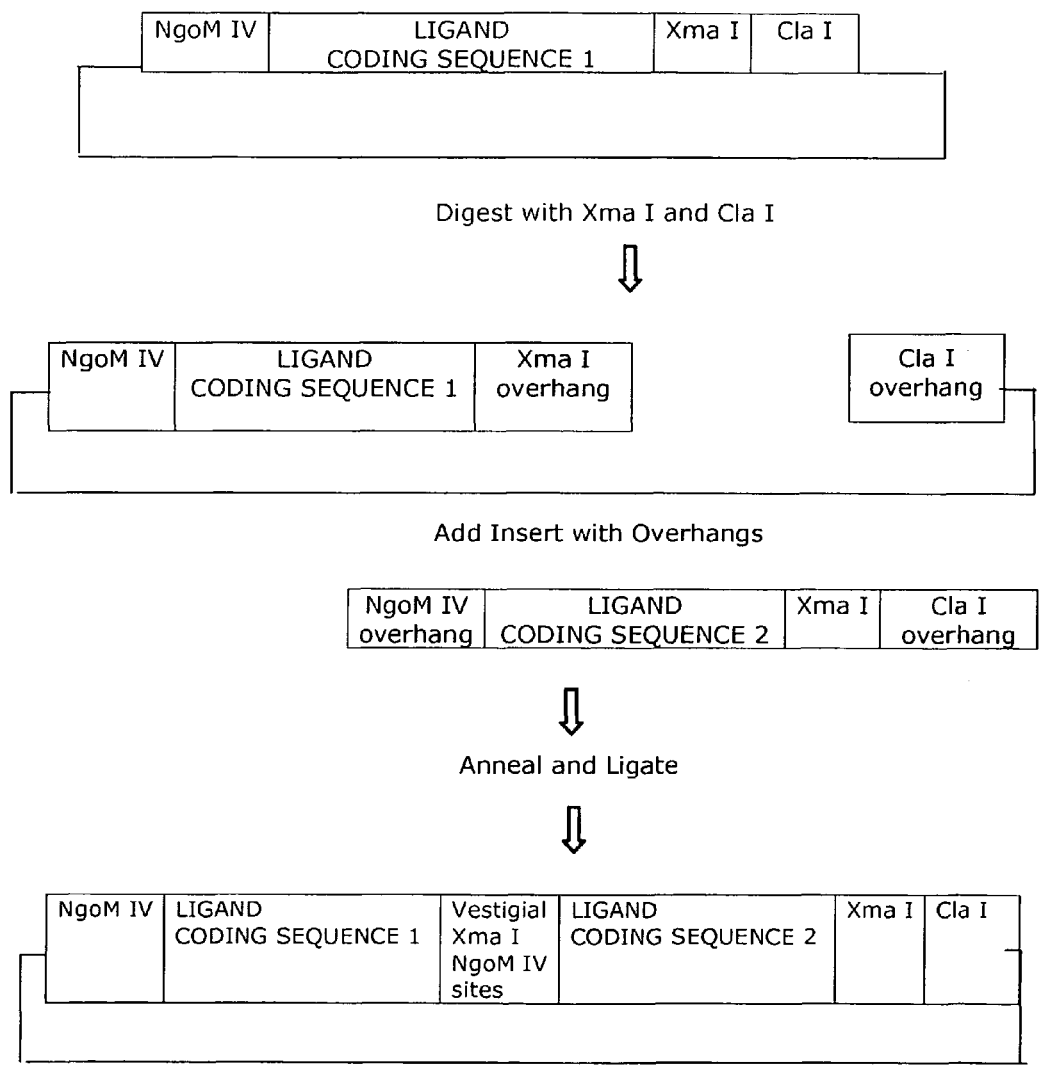
FIG. 8 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 8.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endonuclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, degron, and/or localization signals.

Polyligands and methods of making polyligands that modulate PAI-1 activity are disclosed. Therapeutics include delivery of purified ligand or polyligand with or without a localization signal to a cell. Alternatively, ligands and polyligands with or without a localization signals are delivered via viral or retroviral constructs such as those employing adenovirus, lentivirus, adeno-associated virus, or other viral or retroviral constructs that provide for expression of protein product in a cell.

The PAI-1 ligands or polyligands, nucleic acids encoding PAI-1 ligands and polyligands, and vectors containing nucleic acids encoding PAI-1 ligands and polyligands can be used to treat a subject with a fibrotic condition or a subject at risk for developing fibrosis. The subject may be an animal with a naturally-occurring fibrotic condition or surgery-induced, chemical-induced, genetically-induced, or other experimentally-induced fibrotic condition. The fibrotic condition may result from diabetes or hyperglycemia induced by chemical exposure, dietary manipulation, genetic manipulation, obesity, or natural maturation. The fibrotic condition may also result from hypertension, ischemia, necrosis, immune-mediated injury, tobacco smoke exposure, chemical exposure, fiber exposure, viral or bacterial infection, or idiopathic causes. The PAI-1 ligands or polyligands, nucleic acids encoding PAI-1 ligands and polyligands, and vectors containing nucleic acids encoding PAI-1 ligands and polyligands can be used to treat fibrosis and other PAI-1 associated conditions in heart, blood, kidney, liver, lung, and ovary. The PAI-1 ligands or polyligands, nucleic acids encoding PAI-1 ligands and polyligands, and vectors containing nucleic acids encoding PAI-1 ligands and polyligands may also be useful for treating various cancers in which PAI-1 is expressed.

Another embodiment of the invention is a method for transferring a polynucleotide encoding a ligand or polyligand to cardiovascular tissue described herein.

Another embodiment of the invention is a method for transferring a polynucleotide encoding a ligand or polyligand to cardiovascular tissue comprising one of the following: local injection of adenovirus, ex vivo transduction of monocytes, or direct injection into aorta.

Another embodiment of the invention is a method for assessing the function of PAI-1 in the formation of unstable plaques described herein.

Another embodiment of the invention is a method for assessing the function of PAI-1 in the formation of unstable plaques comprising the step of developing an insulin resistant mouse model.

Another embodiment of the invention is a method of achieving spatial or temporal control of a ligand or polyligand described herein.

Another embodiment of the invention is a method of achieving spatial control of a ligand or polyligand comprising the step of linking the ligand or polyligand to a tissue-specific promoter.

Another embodiment of the invention is a method of achieving spatial control of a ligand or polyligand comprising the step of linking the ligand or polyligand to a localization tether.

Another embodiment of the invention is a method of achieving temporal control of a ligand or polyligand comprising the step of linking the ligand or polyligand to an inducible gene switch.

Another embodiment of the invention is a method for treating, preventing, or ameliorating a cardiovascular disease, comprising the steps of:

a) Identifying a subject with a cardiovascular disease or at risk for developing a cardiovascular disease; and b) Administering a PAI-1 ligand or polyligand to the subject.

Another embodiment of the invention is a method for treating, preventing, or ameliorating a fibrotic condition, comprising the steps of:

a) Identifying a subject with a fibrotic condition or at risk for developing a fibrotic condition; and b) Administering a PAI-1 ligand or polyligand to the subject.

The purified PAI-1 ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Another aspect of the invention is a method for treating or preventing atherosclerosis comprising:

a) Identifying a subject with vascular injury or at risk for vascular injury;

b) Isolating monocytes from said subject;

c) Introducing into said monocytes at least one polynucleotide encoding a polypeptide modulator of the fibrinolytic pathway linked to a promoter, to produce modified cells; and d) Introducing said modified cells to said subject.

Another embodiment of the invention relates to a method of preparing modified cells for delivering a polypeptide modulator of the fibrinolytic pathway to a subject, comprising introducing into monocytes of said subject at least one polynucleotide encoding a polypeptide modulator of the fibrinolytic pathway linked to a promoter, to produce modified cells.

In one embodiment of the invention, the promoter is an inducible promoter. In another embodiment of the invention, the promoter is a macrophage-specific promoter. In another embodiment of the invention, the promoter is a foam cell-specific promoter.

The invention has several advantages over current local delivery methods for the treatment of atherosclerosis such as the use of catheter-based delivery of drug coated stents or balloon angioplasty mediated viral delivery to endothelial and/or vascular smooth muscle cells. In addition to the challenges associated with device mediated delivery approaches vascular cell types are difficult cells to transduce and exhibit poor transgene expression, making local delivery of a transgene to these cells incredibly difficult. Therefore these methods have varying degrees of effectiveness. The subject invention utilizes a circulating cell type, monocytes, that will home to areas of vascular injury, thereby eliminating the need for a device mediated local delivery of a protein-based therapeutic. Monocytes differentiate to macrophages at the site of vascular injury. The macrophages, once in the local environment of the atheroma, will further differentiate to foam cells.

Macrophages contribute to most phases of atherosclerotic development. Therefore they present as a useful cell type for delivery of a transgene, expression of a modulator of the fibrinolytic pathway, locally to atherosclerotic lesions. These lesions can occur throughout the vasculature. The fibrinolytic pathway has been shown to play key roles in atherosclerotic development and progression, however it also plays key roles in hemostasis. Therefore the invention contemplates spatiotemporal control of modulators of this pathway, in order to prevent adverse effects, such as uncontrolled bleeding, that systemic delivery could potentially cause. In one embodiment of the invention, temporal control is achieved through the use of an inducible gene switch.

For example, another aspect of the invention is a method for treating or preventing atherosclerosis comprising:

a) Identifying a subject with vascular injury or at risk for vascular injury;

b) Isolating monocytes from said subject;

c) Introducing into said monocytes (1) a polynucleotide encoding a gene switch, said gene switch comprising at least one transcription factor sequence, wherein said at least one transcription factor sequence encodes a chemical ligand-dependent transcription factor, and (2) at least one polynucleotide encoding a polypeptide modulator of the fibrinolytic pathway linked to a promoter which is activated by said chemical ligand-dependent transcription factor, to produce modified cells;

d) Introducing said modified cells to said subject; and e) Introducing a chemical ligand to the subject to activate the promoter.

Another embodiment of the invention relates to a method of preparing modified cells for delivering a polypeptide modulator of the fibrinolytic pathway to a subject, comprising introducing into monocytes of said subject (a) a polynucleotide encoding a gene switch, said gene switch comprising at least one transcription factor sequence, wherein said at least one transcription factor sequence encodes a chemical ligand-dependent transcription factor, and (b) at least one polynucleotide encoding a polypeptide modulator of the fibrinolytic pathway linked to a promoter which is activated by said chemical ligand-dependent transcription factor, to produce modified cells.

In one embodiment, the modulator of the fibrinolytic pathway is a PAI-1 ligand or polyligand described herein. However, the methods of treating or preventing atherosclerosis are not limited to the PAI-1 ligands or polyligands described herein, but may employ any polypeptide modulator of the fibrinolytic pathway. By way of example, modulators of the fibrinolytic pathway useful in the present method may include other polypeptide PAI-1 inhibitors; natural plasminogen activators such as those disclosed in U.S. Pat. No. 5,830,849; mutant plasminogen activators such as those described in U.S. Pat. No. 5,866,413; or plasminogen activator fragments such as those disclosed in U.S. Pat. No. 5,039,791.

The instant invention also contemplates the use of macrophage-specific regulatory elements to control an inducible gene switch to restrict transgene expression to macrophages. In this way, both spatial and temporal control of transgene expression can be achieved, so that expression is restricted to macrophages and/or macrophage derived cells within the atheroma. The macrophage-specific regulatory elements are utilized in an inducible gene switch system that can regulate expression of the modulator of the fibrinolytic pathway, within the specified cell type, with the addition of a chemical. The gene expression program is transduced into a macrophage precursor cell, such as a monocyte, ex vivo, and reintroduced into the body for treatment of atherosclerosis. An example of a macrophage-specific regulatory element useful for the present invention are regulatory elements from the macrophage-restricted CD68 gene described in Gough, P. J. and E. W. Raines, Blood 101(2): 485-91 (2003).

For example, another aspect of the invention is a method for treating or preventing atherosclerosis comprising:
 a) Identifying a subject with vascular injury or at risk for vascular injury;
 b) Isolating monocytes from said subject;
 c) Introducing into said monocytes (1) a polynucleotide encoding a gene switch, said gene switch comprising at least one transcription factor sequence linked to a macrophage-specific regulatory element, wherein said at least one transcription factor sequence encodes a chemical ligand-dependent transcription factor, and (2) at least one polynucleotide encoding a polypeptide modulator of the fibrinolytic pathway linked to a promoter which is activated by said chemical ligand-dependent transcription factor, to produce modified cells;
 d) Introducing said modified cells to said subject; and
 e) Introducing a chemical ligand to the subject to activate the promoter.

Further, another embodiment of the invention relates to a method of preparing modified cells for delivering a polypeptide ligand or polyligand to a subject, comprising introducing into monocytes of said subject (a) a polynucleotide encoding a gene switch, said gene switch comprising at least one transcription factor sequence linked to a macrophage-specific regulatory element, wherein said at least one transcription factor sequence encodes a chemical ligand-dependent transcription factor, and (b) at least one polynucleotide encoding a polypeptide modulator of the fibrinolytic pathway linked to a promoter which is activated by said chemical ligand-dependent transcription factor, to produce modified cells.

In other embodiments, additional polynucleotides encoding other therapeutic proteins such an apolipoprotein are introduced into the monocytes.

The present invention contemplates the treatment of other conditions involving fibrosis in other tissues through targeting other macrophage populations. For example, other fixed macrophages, such as alveolar macrophages, can be targeted through specific promoters or other means to direct expression of fibrinolytic modulators for a potential treatment of pulmonary fibrosis. Other fixed macrophages and their location within tissues that fall within the scope of the invention include histiocytes in connective tissue, kupffer cells in the liver, microglial cells within neural tissue, epithelioid cells within granulomas, osteoclasts within bone, sinusoidal lining cells within the spleen and mesangial cells within the kidney. The present invention contemplates treatment of any fibrotic condition involving these and other macrophage sub-types through targeted expression of a polypeptide modulator of the fibrinolytic pathway.

Another aspect of the invention is a method for treating, preventing, or ameliorating a fibrotic condition involving a fixed macrophage population comprising
 a) Identifying a subject with a fibrotic condition;
 b) Isolating monocytes from said subject;
 c) Introducing into said monocytes at least one polynucleotide encoding a polypeptide modulator of the fibrinolytic pathway linked to a regulatory element specific for a fixed macrophage population, to produce modified cells; and
 d) Introducing said modified cells to said subject.

The present invention also contemplates in vivo approaches for targeted expression of a polypeptide modulator of the fibrinolytic pathway to cells of monocytic origin through the use of a monocyte-specific vector such as that described in U.S. Pat. No. 6,875,612.

Methods

Outcome: The collective data, obtained from both in vitro and in vivo experimentation, demonstrating successful modulation of fibrinolytic activity in cardiovascular tissues will demonstrate therapeutic efficacy of localized PAI-1 inhibition in diseased cardiovascular tissues. The clinical significance for the development of PAI-1 decoys will be, in patients with type II diabetes, to decrease the formation of unstable atherosclerotic plaques.

Objective: The targeted goal is to develop an adenoviral gene therapeutic with inducible, tissue-specific expression of a PAI-1 decoy that is targeted to the extracellular face membrane and/or extracellular milieu of diseased vessels. The individual components that make up this therapeutic are described below.

Individual Components—PAI-1 Decoys: Plasminogen activator inhibitor-1 (PAI1) is a serine protease inhibitor (serpin) involved in regulating fibrinolysis. Among its targets are tissue plasminogen activator (tPA) and urokinase plasminogen activator (uPA). PAI1 binds its targets in a suicide inhibitor reaction, covalently binding in an intermediate state that only very slowly cleaves (not before normal clearance of the complex). PAI1 alone possesses a short half-life in solution-less than 2 hrs. It spontaneously undergoes a conformational shift into a latent form that is non-functional. Association of PAI1 with vitronectin can greatly increase the viable lifetime of the molecule, as well as target it to particular locations in the extracellular matrix (ECM), as vitronectin possesses binding domains for other ECM proteins. The decoys designed combine multiple strategies to inhibit PAI-1 and include sequestration of the molecule, down-regulation via peptides that cause a conformational shift, and proteolysis of the molecule.

Spatial and Temporal Control of PAI-1 Decoys: Proper spatial localization of PAI-1 decoys, both at the tissue and cellular level, is necessary in order to maximize the effectiveness and minimize the toxicity of PAI-1 decoys. At the level of the tissue, this will be achieved through the use of tissue specific promoters controlling PAI-1 decoy expression. While at the level of the cell, this will be achieved by utilization of localization tethers fused to the PAI-1 decoys.

Tissue Specific Promoters: In order to limit expression of PAI-1 decoys to a target organ(s), tissue specific promoters have been designed to direct expression of a transgene to specific vascular cell types, to include; vascular smooth muscle cells and endothelial cells. Temporal control will be engineered using RheoSwitch technology for inducible expression using the validated tissue specific promoters.

Localization Tethers: For the purpose of spatial control at the cellular level, localization tethers have been designed that, when fused to a PAI-1 decoy, will transport it to the proper locale for therapeutic benefit. Some in vivo optimization of therapeutic decoy delivery may be required in order to achieve an outcome that is most beneficial for atherosclerotic plaques. For example, cells targeted by the gene therapy might yield the best effects if the concentration gradient of therapeutic decoy were shallow and broad—perhaps diffusing far and wide to even yield some subtle endocrine effects (Class 2). On the other hand, it may also be desirable to limit the concentration gradient of decoy such that it is primarily present on the surfaces of transfected cells; this approach would limit the zone of therapy to a much smaller region (Class1). Class 3, the subject of this summary, attempts to "steer a middle course," and enable paracrine diffusion of the decoy under conditions (i.e., a proteolytic milieu) where injury healing is underway.

Scope: Development of validated decoy, loc and promoter components in addition to successful integration of these individual components for the development of a gene therapeutic for use in preclinical studies. Successful completion of these experiments will demonstrate that modulation of fibrinolysis by localized inhibition of PAI-1 will, in a metabolic disease model, reduce the formation of unstable atherosclerotic plaque formation in the vasculature.

Preclinical Model: A preclinical mouse model of insulin resistance with atherosclerotic development will be used to assess the function of PAI-1 in the formation of unstable plaques. Gene transfer techniques in mice will be evaluated for use in gene delivery to target tissues.

Insulin resistant mouse model—Overall plan for development of the mouse model): Exp. 1) induction of atherosclerosis and myocardial infarction in insulin resistant mice (IRS1+/−ApoE−/− and IRS2+/−ApoE−/−) with insulin resistance verified by assay of FFA, triglycerides, and insulin and control (C57BL6) non-insulin resistant mice, and insulin resistant PAI-1 deficient mice (IRS1+/− ApoE−/− PAI-1+/− and IRS2+/− ApoE−/− PAI-1+/−) of 10 weeks of age; performance of high resolution ultrasonic cardiac interrogation when the animals are 12 weeks and 16 weeks of age for assessment of systolic and diastolic function; and assessment of infarct size, the extent of fibrosis, and the amount and localization of PAI-1 in left ventricles of the hearts of mice of 16 weeks of age subjected to coronary occlusion at 10 weeks of age; 2) delineation of the relationship between the extent of fibrosis and concomitant impairment of left ventricular function normalized for infarct size in the diverse strains of mice; 3) elimination of the potential role of PAI-1 in the generation of cardiac fibrosis following coronary occlusion and induction of infarction by crossbreeding PAI-1 deficient animals with insulin resistant animals that otherwise overexpress PAI-1 and performing the same studies as those described in 1 and 2 above; and, 4) characterization of aortic atherosclerotic plaques with cell imaging techniques.

Gene Transfer of Cardiovascular Tissues: While multiple studies in gene transduction of vascular tissues have been attempted, both the ideal vector and route of administration have not been defined for clinical gene therapeutics. Systemic delivery will result in rapid clearance of adenovirus and attachment/infection in the liver. Local transduction of cardiovascular tissues has been reported. While cardiomyocytes are easily transduced by adenovirus, endothelial cells (ECs) and vascular smooth muscle cells (VSMCs) are not. VSMCs are largely refractory to gene transfer mediated by adenoviruses of serotypes 2 and 5. This is due to poor viral entry and inefficient transcription of the transgene itself from traditional ubiquitous promoters. Reduced viral entry is explained largely by the limited expression of the coxsackie adenovirus receptor (CAR) on the surface of SMC, which results in transduction levels that are markedly lower than those achieved in epithelial cells infected at the same dose [(Beck, Uramoto et al. 2004) see attached article].

Local Injection of Adenovirus: One recommendation is to perform intraventricular injections into the lumen of the left ventrical through the apex of the heart. This procedure has been shown to result in transgene expression in the aortic endothelium (Juan, Lee et al. 2001). Although no VSMC expression was seen using this method, this may be due to inefficient transcription of the transgene. CMV mediated transgene expression is inefficient in VSMCs, therefore inclusion of VSMC specific promoters has been shown to result in increased expression in vivo (Akyurek, Yang et al. 2000; Akyurek, Nallamshetty et al. 2001; Appleby, Kingston et al. 2003). Therefore use of a strong VSMC promoter in combination with a high titer of virus could result in VSMC expression using this technique. Additionally by clamping the outgoing vessels during the injection it would be possible to increase exposure of the virus to the target cells. This will also result in perfusion of the heart through the coronaries (Roth, Lai et al. 2004)

Summary—Local injection of adenovirus: This strategy is appropriate for in vivo gene transfer of cardiomyocytes and endothelial cells. However, based on reported findings in the literature it is unlikely that robust expression in VSMCs would be possible, due to the EC barrier and low transduction efficiency.

Ex vivo transduction of monocytes: The other recommendation is to use an ex vivo approach. Macrophages function in all phases of atherosclerotic development, within the vascular wall. Monocytes are recruited and adhere to sites of vascular injury and differentiate into macrophages. Additionally, they also have a high biosynthetic capacity (Beck, Uramoto et al. 2004). Bone marrow cells can be easily isolated, transduced and placed back into the animal for an ex vivo gene delivery approach.

This approach has been used previously to deliver a therapeutic gene to an atherosclerotic region. In most instances of this approach, expression of ApoE was used to promote reverse cholesterol transport (Hasty, Linton et al. 1999; Van Eck, Herijgers et al. 2000; Ishiguro, Yoshida et al. 2001; Juan, Lee et al. 2001; Yoshida, Hasty et al. 2001; Gough and Raines 2003). Additionally, monocyte-derived macrophages contribute to the inflammatory response to MI. Therefore this approach could also be used in the MI model to decrease PAI-1 activity in the infarct.

Summary—Ex vivo transduction of monocytes: The major drawback with this approach is that monocytes are resistant to the Ad5 serotype (Burke, Sumner et al. 2002; Burke 2003). Ad11p and Ad35 serotypes as well as lentiviral and retroviral vectors readily infect hematopoetic cell types, including myeloid cell types such as monocytes (Segerman, Lindman et al. 2006).

Direct Injection into the Aorta: Another approach is to perform direct intra-arterial injections into the ascending aorta, in the area of the plaque. This is a common approach used for gene transfer to the myocardium, however, I am unsure of the feasibility of this approach for gene transfer to the aorta.

Overall Summary—Gene Transfer of Cardiovascular Tissues: Based on assessment of the various gene transfer strategies that have been reported, either transduced monocytes or intracoronary delivery, via injection into the lumen of the left ventricle, while cross-clamping the pulmonary artery and the aorta would provide a feasible gene transfer approach for multiple cardiovascular cell types.

Experimental Framework

Decoys—Project 1

1. In vitro validation using HepG2 cells for PAI-1 elaboration
 a. Antigen
 b. Activity
2. In vitro validation using VSMC for PAI-1 elaboration
 a. Antigen
 b. Activity
3. In vitro validation using VSMC migration assay
 a. Human VSMC
 b. Mouse VSMC Localization tethers—Project 2
1. In vitro validation using VSMC
  a. Antigen in media vs. cell (membrane) lysate
  b. Localization by fluorescent microscopy
2. In vitro validation using EC
  a. Antigen in media vs. cell (membrane) lysate
  b. Localization by fluorescent microscopy
3. In vitro validation monocyte/macrophage cell
  a. Antigen in media vs. cell (membrane) lysate
  b. Localization by fluorescent microscopy
Promoters—Project 3
4. In vitro validation using VSMC
  a. Reporter activity in VSMC and non-VSMC
  b. Inducible reporter activity in VSMC and non-VSMC
5. In vitro validation using EC
  a. Reporter activity in EC and non-EC
  b. Inducible reporter activity in EC and non-EC
6. In vitro validation monocyte/macrophage cell
  a. Reporter activity in monocyte/macrophage cell and non-monocyte/macrophage cell type
  b. Inducible reporter activity in monocyte/macrophage cell and non-monocyte/macrophage cell type
Localized Decoys—Project 4
1. In vitro validation of transduced VSMC (assay expression and localization)
2. In vitro validation of transduced EC (assay expression and localization)
3. In vitro validation using transduced VSMC migration assay
  a. Human VSMC
  b. Mouse VSMC
4. In vitro validation of transduced monocyte/macrophage cell (assay expression and localization)
Virus with inducible/tissue specific expression of a reporter—Project 5
1. In vitro validation VSMC
2. In vitro validation EC
3. In vitro validation monocyte/macrophage cell
Viral Gene Therapeutic—Project 6
1. In vitro validation using VSMC (assay expression and localization)
2. In vitro validation of transduced EC (assay expression and localization)
3. In vitro validation using transduced VSMC migration assay
  a. Human VSMC
  b. Mouse VSMC
4. In vitro validation of transduced monocyte/macrophage cell (assay expression localization)
Compiled Report of In Vitro Data—Project 7
1. Compiled data from projects 1-6
Preclinical model—Project 8
1. Induction of atherosclerosis in insulin resistant (IR) mice with or without PAI-1 deficiency.
2. Characterization of aortic atherosclerotic plaques in PAI-1 null, insulin resistant (IR) mice.
3. Validation of gene transfer model
  a. Ex vivo transduced monocytes
  b. Intramyocardial injection with or without blockage of outgoing vessels
  c. Direct injection into the aorta

EXAMPLES

Examples

PAI-1 Decoys and Inhibition Strategies

Exemplary inhibition mechanisms for PAI-1 decoys are depicted in FIG. 16.

Figure 9:
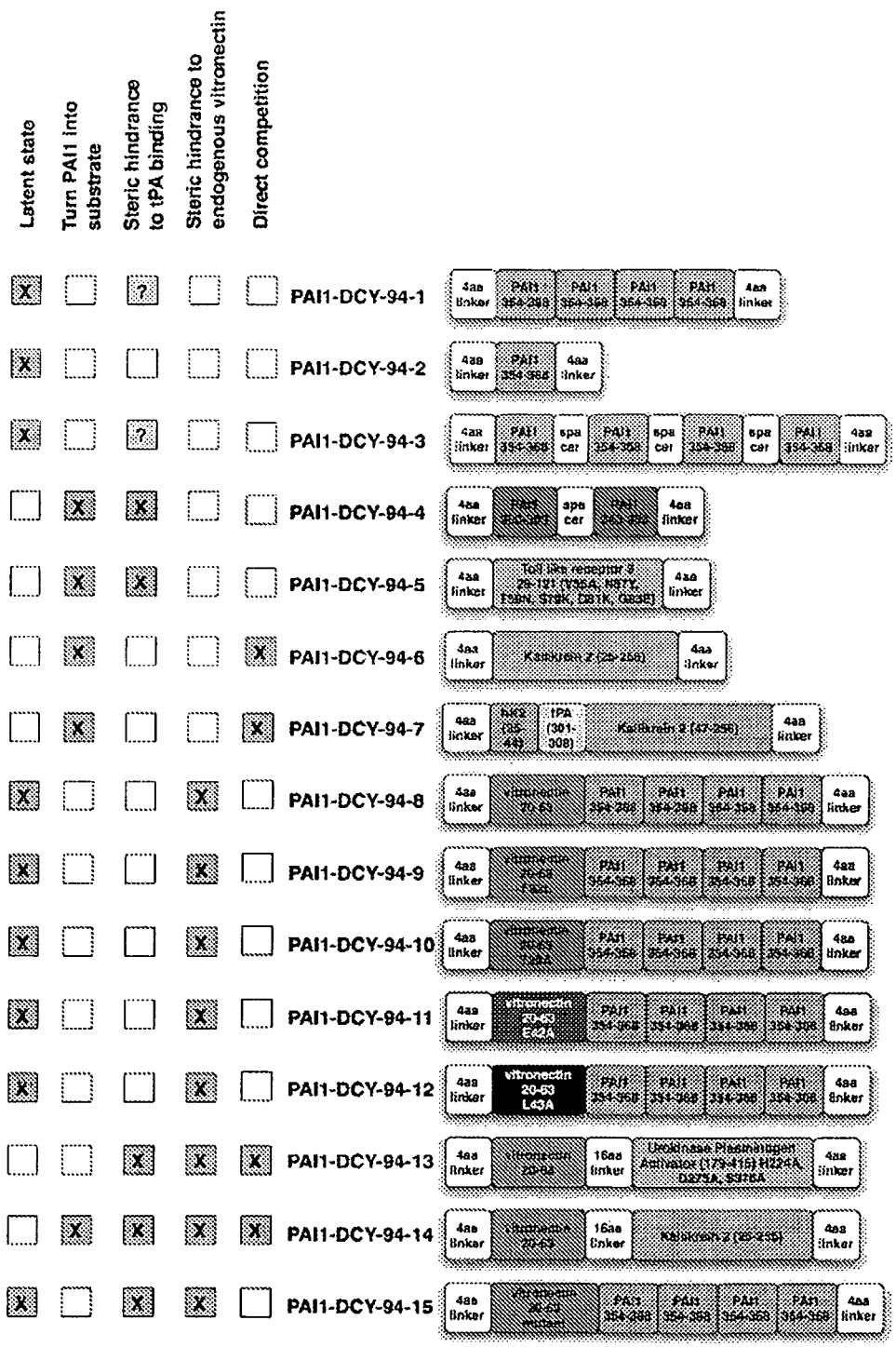
FIG. 9 shows examples of ligands and polyligands and their PAI-1 inhibition mechanisms.

In most every case, the following exemplary decoy designs cover multiple inhibition mechanisms. A schematic representation of each exemplary decoy design and its inhibition mechanisms is depicted in FIG. 9. The decoy designs depicted in FIG. 9 and described in the foregoing examples are intended to serve as illustrative embodiments of the invention. It will be understood by those of ordinary skill in the art that the invention is not limited to the particular embodiments described herein, and that a wide range of equivalent designs and inhibition strategies fall within the scope of the invention.

See 'Description of the Polypeptide and Polynucleotide Sequences' for corresponding SEQ ID NOS of the following exemplary PAI-1 decoys.

PAI-1 Decoys 1-3: Native PAI1 possesses a short half-life in solution-less than 2 hrs. It spontaneously undergoes a conformational shift into a latent form that is non-inhibitory. The reactive center loop (RCL) peptide, which is immediately adjacent to the protease cleavage site (R346-M347), undergoes insertion into an existing b-sheet on the PAI1 structure upon shift into latent form. Peptides based on this RCL sequences can block PAI1 protease inhibitory activity.

Based on this PAI-1 decoys 1-3 will exploit the RCL sequence to inhibit the molecule. Recombinant peptides based on this sequence have been shown to be inhibitory to PAI1 action, operating much the same as the native RCL but on a shorter time scale. Individual sequences, multiple sequences, and multiple sequences separated by spacers (to potentially multimerize with PAI1 molecules) will be evaluated. The sequences will mimic the natural RCL peptide action. These DCYs will almost definitely inhibit—the goal is to identify which type of construct will inhibit most effectively and potentially combine it with other designs below.

PAI1-DCY-94-1: Four tandem repeats of the RCL peptide will be used to inhibit the normal PAI1 suicide reaction. This DCY can be compared to PAI1-DCY-94-2 and to PAI1-DCY-94-3 for relative efficiency.

PAI1-DCY-94-2: A single RCL will be used to inhibit the normal PAI1 suicide reaction. This DCY can be compared to PAI1-DCY-94-1 and to PAI1-DCY-94-3 for relative efficiency.

PAI1-DCY-94-3: Four tandem repeats of the RCL peptide, separated by spacers to enhance interactions with multiple PAI1 molecules, will be used to inhibit the normal PAI1 suicide reaction. This DCY can be compared to PAI1-DCY-94-1 and to PAI1-DCY-94-2 for relative efficiency.

PAI-1 Decoys 4 and 5: Upon binding to any of several serine proteases (for example tPA, uPA, thrombin), PAI1 undergoes a dramatic conformational shift during cleavage that results in a suicide inhibitory reaction. Experimental evidence shows that this rearrangement in structure is an important part of the inhibition mechanism. Delaying this conformational shift so the cleavage reaction can proceed to completion would turn PAI1 into no more than a normal substrate. The reactive center loop (RCL) peptide, which is disordered in structures of active PAI1 inserts into a beta sheet.

PAI-1 decoys 4 and 5 attempt to interact with the RCL of active pAI1 with either of two potential goals in mind-1) to slow the insertion of RCL into the PAI1 structure and allow PAI1 to be naturally cleaved by serine protease targets, or 2) through steric interference to prevent binding to protease targets altogether. The RCL peptide interacts with a beta-sheet in PAI1. Sequences from this sheet are adopted to engage the native RCL.

PAI1-DCY-94-4: The goal of this DCY is to stabilize the RCL while it is still independent of the sheet and allow the cleavage reaction to proceed. Beta strands that make up part of the sheet into which the RCL inserts will be used to provide an alternative binding surface for the RCL peptide. Two antiparallel beta strands from PAI1 will be used to create part of the native beta sheet to which the RCL insets and binds. The two strands making up this DCY are non-contiguous in sequence, so four residues that form a beta turn will be used to attach them and allow for proper secondary structure.

PAI1-DCY-94-5: The goal of this DCY is to stabilize the RCL while it is still independent of the sheet and allow the cleavage reaction to proceed. The actual insertion of the RCL peptide occurs in between two beta strands that run parallel in the PAI1 structure. These two strands are not contiguous in sequence in the native structure, although they are sequential members of this beta sheet in PAI1.

Leucine rich repeats (LRR) are motifs found in several proteins, including the extracellular matrix proteins decorin and biglycan, and the Toll-like receptors. The motif consists of a slightly concave surface consisting of beta strands and a convex surface of helical or semi-helical structure. The repeated stacking of these motifs produces a solenoid structure with a series of parallel beta strands forming a concave sheet. Leucines occur in critical parts of the sequence and provide internal packing that allows for great variability on the outward-facing residues. The motif is stable, especially when repeated consecutively. Several LRRs from the Toll like receptor 3 ectodomain will be used as a scaffold to recreate a portion of the native sheet structure into which the RCL inserts. The LRR, because of its stacking of parallel strands, makes it ideal for mimicking a portion of the PAI1 beta sheet structure. Due to the size of the sheets in PAI1 they will be recreated in two sections on the LRR scaffold.

PAI-1 Decoys 6 and 7: Kallikrein 2 (hK2) is a serine protease normally expressed in prostate and useful as a marker for prostate cancer. It exhibits strong specificity for Arg in the P1 cleavage site. It can cleave and subsequently inactivate PAI1 with high efficiency compared to other proteases. The expression profile for this protein combined with its specificity make it good candidate for a DCY that will actually cleave and inactivate PAI1. If targeted to a region where PAI1 is present, it should be able to cleave and thereby inactivate PAI1 efficiently.

PAI-1 Decoys 6 and 7 use an active protease, kallikrein 2 (hK2), to digest PAI1. hK2 is a serine protease normally found in prostate. It is specific in its expression profile and has use as a marker for prostate cancer. It is specific in its substrates and has been shown to digest PAI1 specifically as opposed to being inhibited by it. One of these construct possesses a charged loop that mimics a native tPA sequence shown to be important in PAI1 binding.

PAI1-DCY-94-6: Potential mutations to kallikrein 2 could be made to enhance binding specificity. A loop present in tPA contains several charged residues that are important in tPA-PAI1 binding. The corresponding loop in hK2 could be mutated to match this sequence and potentially enhance binding specificity for PAI1.

PAI1-DCY-94-7: Kallikrein 2 (hK2) is a serine protease normally expressed in prostate and useful as a marker for prostate cancer. It exhibits strong specificity for Arg in the P1 cleavage site. It can cleave and subsequently inactivate PAI1 with high efficiency compared to other proteases. The expression profile for this protein combined with its sequence specificity make it good candidate for a DCY that will actually cleave and inactivate PAI1.

A positively charged loop on the surface of tissue plasminogen activator (tPA) has been shown to be important in PAI1 binding. It is believed to interact with a series of acidic residues near the RCL peptide of PAI1. This region is harvested replaces the shorter loop present in hK2. The addition of this sequence could result in higher affinity binding and more efficient cleavage.

PAI-1 Decoys 8-12: Plasminogen activator inhibitor-1 (PAI1) is a serine protease inhibitor involved in regulating fibrinolysis. Among its targets are tissue plasminogen activator (tPA) and urokinase plasminogen activator (uPA). PAI1 binds its targets in a suicide inhibitor reaction, covalently binding in an acyl enzyme intermediate state that only very slowly cleaves (and not before clearance of the complex). PAI1 possesses a short half-life in solution—less than 2 hrs. It spontaneously undergoes a conformational shift into a latent form that is non-functional. The reactive center loop (RCL) peptide, which is immediately adjacent to the cleavage site, undergoes insertion into an existing b-sheet on the PAI1 structure. Peptides based on this RCL sequences can block PAI1 protease inhibitory activity.

Vitronectin is an extracellular matrix (ECM) molecule that binds to multiple ECM partners. It binds PAI1 with high affinity and dramatically increases its half-life, allowing it to interact with and inhibit tPA, uPA, and other serine proteases. The interaction with PAI1 occurs through vitronectin's somatomedin B (SMB) domain. The binding is specific and high affinity (Kd ~1 nM).

PAI-1 Decoys 8-12 make use of the vitronectin interaction with PAI1 and combine it with the RCL inhibitory peptide. Vitronectin's somatomedin B (SMB) domain binds with high affinity to PAI1 and can greatly extend its effective half-life. Several papers have shown that mutations of tyrosines on this binding surface can abrogate binding completely. Our goal here, though, is not to abolish binding but to minimize the stabilization effect of SMB binding while retaining at least some of the binding affinity. A series of conservative mutations are made to probe the binding surface. The SMB mutations are combined with RCL peptides which will bestow considerable inhibitory properties on the DCYs. A construct that maximizes binding while minimizing stability will be found, whether it is the native SMB domain or one of the mutant structures. The high affinity binding of SMB will in effect tether the RCL peptides to PAI1 and should promote more ready interaction.

PAI1-DCY-94-8: The DCY will use the SMB domain of vitronectin to target PAI1 binding with high affinity and specificity. The SMB domain will be attached to multiple repeats of an inhibitory peptide based on the RCL of PAI1. The initial SMB binding will bring the peptide into close proximity, and insertion into the b-sheet can occur, resulting in inhibition, and possible disengagement of the SMB domain. The RCL peptide could potentially act either in cis or in trans, affecting nearby PAI1 molecules with these multiple binding and inhibiting domains.

PAI1-DCY-94-9: The decoy will use the somatomedin B domain of vitronectin to target PAI1 binding with high affinity and specificity. The SMB domain will be attached to multiple repeats of an inhibitory peptide based on the RCL of PAI1. The initial SMB binding will bring the peptide into close proximity, and insertion into the b-sheet can occur, resulting in inhibition, and possible disengagement of the SMB domain. The RCL peptide could potentially act either in cis or in trans, affecting nearby PAI1 molecules with these multiple binding and inhibiting domains. The SMB domain will be mutated. The mutation will potentially reduce the stabilizing effect of vitronectin for PAI1 but will maintain sufficient affinity to target the RCL peptide effectively.

PAI1-DCY-94-10: The decoy will use the somatomedin B domain of vitronectin to target PAI1 binding with high affinity and specificity. The SMB domain will be attached to multiple repeats of an inhibitory peptide based on the RCL of PAI1. The initial SMB binding will bring the peptide into close proximity, and insertion into the b-sheet can occur, resulting in inhibition, and possible disengagement of the SMB domain. The RCL peptide could potentially act either in cis or in trans, affecting nearby PAI1 molecules with these multiple binding and inhibiting domains. The SMB domain will be mutated. The mutation will potentially reduce the stabilizing effect of vitronectin for PAI1 but will maintain sufficient affinity to target the RCL peptide effectively. Several research articles have demonstrated mutations that abolish binding, specifically T→A mutations at the binding interface. The goal here is not to eliminate binding but to eliminate as much as possible the secondary stabilization effect of vitronectin binding to PAI1.

PAI1-DCY-94-11: The decoy will use the somatomedin B domain of vitronectin to target PAI1 binding with high affinity and specificity. The SMB domain will be attached to multiple repeats of an inhibitory peptide based on the RCL of PAI1. The initial SMB binding will bring the peptide into close proximity, and insertion into the b-sheet can occur, resulting in inhibition, and possible disengagement of the SMB domain. The RCL peptide could potentially act either in cis or in trans, affecting nearby PAI1 molecules with these multiple binding and inhibiting domains. The SMB domain will be mutated. The mutation will potentially reduce the stabilizing effect of vitronectin for PAI1 but will maintain sufficient affinity to target the RCL peptide effectively.

PAI1-DCY-94-12: The decoy will use the somatomedin B domain of vitronectin to target PAI1 binding with high affinity and specificity. The SMB domain will be attached to multiple repeats of an inhibitory peptide based on the RCL of PAI1. The initial SMB binding will bring the peptide into close proximity, and insertion into the b-sheet can occur, resulting in inhibition, and possible disengagement of the SMB domain. The RCL peptide could potentially act either in cis or in trans, affecting nearby PAI1 molecules with these multiple binding and inhibiting domains. The SMB domain will be mutated. The mutation will potentially reduce the stabilizing effect of vitronectin for PAI1 but will maintain sufficient affinity to target the RCL peptide effectively.

PAI-1 Decoys 13 and 14: Vitronectin is an extracellular matrix (ECM) molecule that binds to multiple ECM partners. It binds PAI1 with high affinity and dramatically increases its half-life, allowing it to interact with and inhibit tPA, uPA, and other serine proteases. The interaction with PAD occurs through vitronectin's somatomedin B (SMB) domain. The binding is specific and high affinity (Kd ~1 nM).

Kallikrein 2 (hK2) is a serine protease normally expressed in prostate and useful as a marker for prostate cancer. It exhibits strong specificity for Arg in the P1 cleavage site. It can cleave and subsequently inactivate PAI1 with high efficiency compared to other proteases. The expression profile for this protein combined with its sequence specificity make it good candidate for a DCY that will actually cleave and inactivate PAI1.

PAI-1 decoys 13-14 also use the SMB domain to increase binding affinity to PAI1 in this case combined with either an inactive protease that can bind and sequester PAI1, or with kallikrein 2, which can digest it.

PAI1-DCY-94-13: Urokinase-type plasminogen activator (uPA) is a serine protease involved in activation of fibrinolytic pathways as well as in signaling responses through its receptor. uPA is a target of PAI1. The enzyme will be truncated to contain only the catalytic domain, and the catalytic residues will me mutated to eliminate activity. This inactive enzyme will be attached to the SMB domain of vitronectin to provide a binding platform for PAI1. PAI1 will be sequestered from interacting with and inhibiting other serine proteases. In contrast to PAI1-DCY-94-7 and PAI1-DCY-94-14, this DCY will not introduce any new enzymatic activity into the target region.

PAI1-DCY-94-14: The decoy will use the somatomedin B domain of vitronectin to target PAI1 binding with high affinity and specificity. The SMB domain will be attached to the active kallikrein 2 molecule to target PAI1 with high affinity and specificity and cleave it, thereby inactivating it.

PAI-1 Decoy 15: Vitronectin is an extracellular matrix (ECM) molecule that binds to multiple ECM partners. It binds PAI1 with high affinity and dramatically increases its half-life, allowing it to interact with and inhibit tPA, uPA, and other serine proteases. The interaction with PAI1 occurs through vitronectin's somatomedin B (SMB) domain. The binding is specific and high affinity (Kd ~1 nM).

PAI-1 decoy 15 is a further set of mutations on the SMB domain. The structure of SMB is almost symmetrical in terms of its backbone. It has a helix and lop that are oriented almost identically on both the PAI1 binding face and on the face opposite the binding site. Five mutations can in many respects recreate a second PAI1 binding site on the SMB molecule. While the spacing between a helix and loop on the rear face is slightly smaller than on the native binding site, the helical region may provide sufficient interaction to bind with some affinity a second PAI1 molecule. RCL peptides are attached so as to potentially interact with both bound PAI1 molecules if two do indeed bind.

The face opposite the native binding site possesses a similar backbone to the binding site. Mutations in this face could partially reproduce a PAI1 binding site. Introduction of several mutations were made to recapitulate most of the PAI1 binding face of SMB. The alpha carbons of the residues to be mutated superimpose with 0.99 Angstroms RMS, and the helical domain superimposes with an RMS of 0.49 Angstroms on alpha carbons.

This could potentially lead to a dimerization of PAI1 molecules in a face-to-face manner. At least two possibilities exist—the RCL peptides from the molecules could interfere with each other, there could be substantial steric hindrance that affects PAI1 inhibitory properties. To augment inhibition of PAI1 exogenous RCL peptide, which binds to and inhibits PAI1 will be attached as a tetrameric repeat to the mutated SMB domain.

Examples

Tissue-Specific Promoters

See 'Description of the Polypeptide and Polynucleotide Sequences' for corresponding SEQ ID NOS of the following exemplary tissue-specific promoters.

Figure 10:
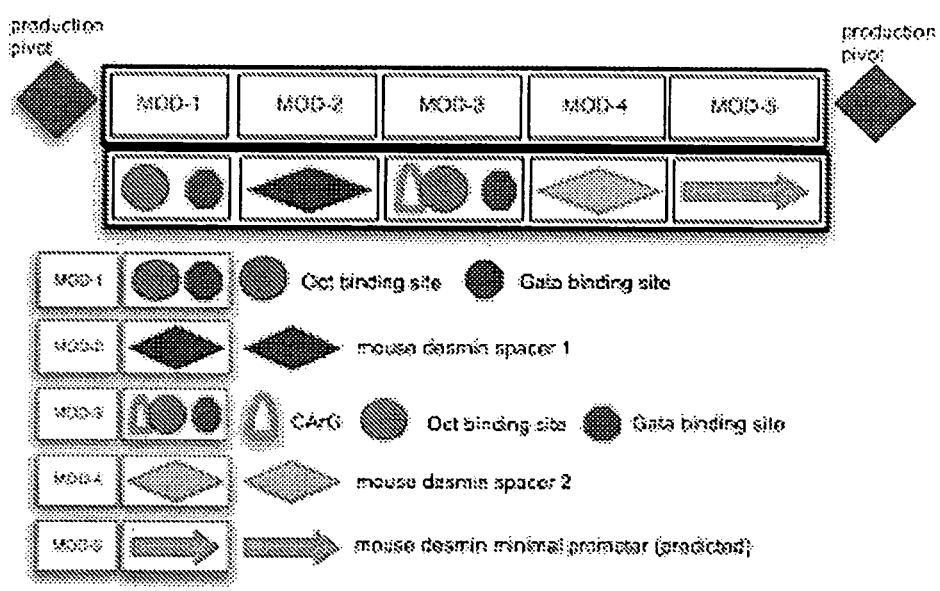
FIG. 10 shows an example of an arterial smooth muscle-specific promoter.

MOD 5306—Arterial smooth muscle-specific promoter (depicted schematically in FIG. 10)—rationale: The desmin gene encodes an intermediate filament protein that is present in skeletal, cardiac, and smooth muscle cells. The promoter region used here contains CArG/octamer overlapping element that can bind the serum response factor and an Oct-like factor; It also contains a minimal promoter (determined by promoter prediction tools); This region is active in arterial smooth muscle cells but not in venous smooth muscle cells or in the heart in vivo.

MOD Rationale for synthetic promoters: Analysis of the promoter regions of collection of genes that are expressed in vascular smooth muscle cells (VSMC) provided a list of several regulatory elements associated with VSMC-specific expression. A combination of one set of such regulatory elements was used in this synthetic promoter construct: the smooth muscle contractile protein SM22 alpha gene fragment fused to nephroblastoma overexpressed (Nov) minimal promoter region. SM22 alpha is an established VSMC differentiation marker. Its minimal promoter has been shown to direct arterial smooth muscle-specific expression of different transgenes. Recently, very high Nov expression in adult rat aorta also has been reported.

Figure 11A:
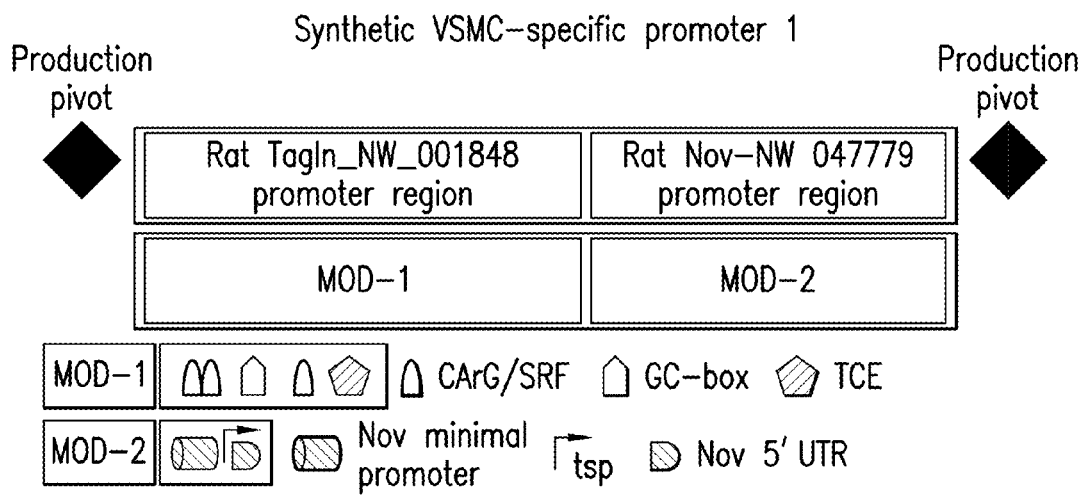
FIGS. 11A-11C show examples of synthetic vascular smooth muscle cell-specific promoters.
Figure 11B:
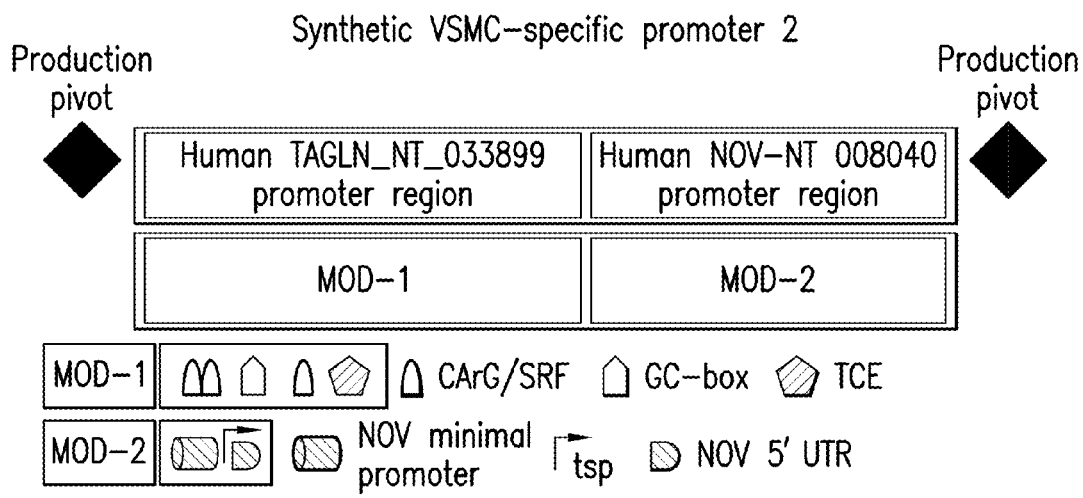
Figure 11C:
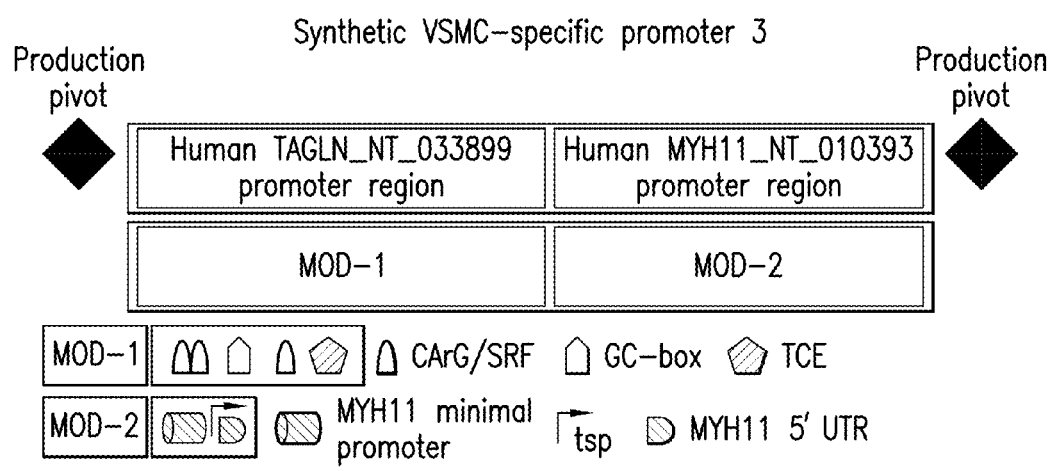

Exemplary synthetic vascular smooth muscle promoters of the invention include MOD 5309—Synthetic VSMC-specific promoter 1 (depicted schematically in FIG. 11A), MOD 5312—Synthetic VSMC-specific promoter 2 (depicted schematically in FIG. 11B), and MOD 5315—Synthetic VSMC-specific promoter 3 (depicted schematically in FIG. 11C)

MOD Rationale: Analysis of the promoter regions of collection of genes that are expressed in vascular smooth muscle cells (VSMC) provided a list of several regulatory elements associated with VSMC-specific expression. A combination of one set of such regulatory elements was used in this synthetic promoter construct: the smooth muscle contractile protein SM22 alpha gene fragment fused to HUMAN myosin, heavy chain 11, smooth muscle promoter region. SM22 alpha is an established VSMC differentiation marker. The rat minimal promoter has been shown to direct arterial smooth muscle-specific expression of different transgenes. Similarly, MYH11 also is specific to smooth muscles.

Figure 12A:
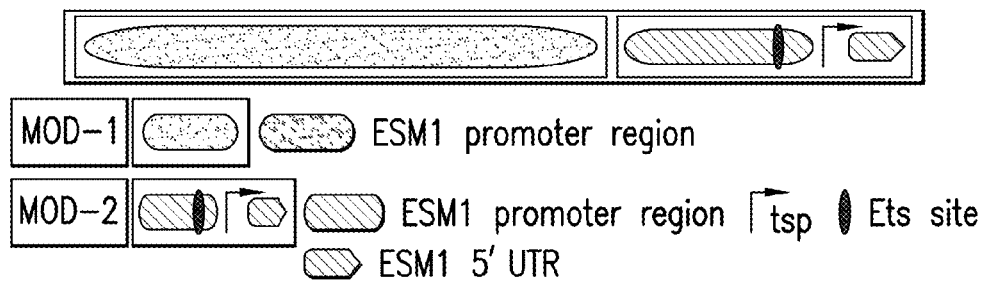
FIGS. 12A-12B show examples of endothelial cell-specific promoters.

MOD 4012—ESM1, endothelial cell-specific promoter (depicted schematically in FIG. 12A)—Mod Rationale: This gene encodes a secreted protein which is mainly expressed in the endothelial cells. The promoter of this gene could be used for gene therapy approaches where endothelial cell-specific expression of therapeutic/decoy molecule is needed.

Figure 12B:
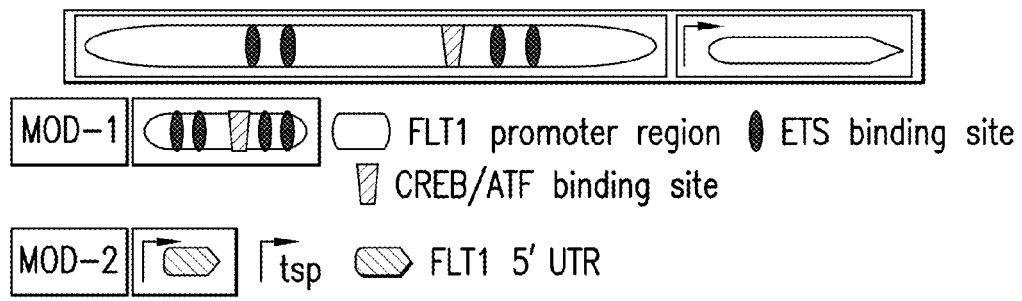
Figure 13A:
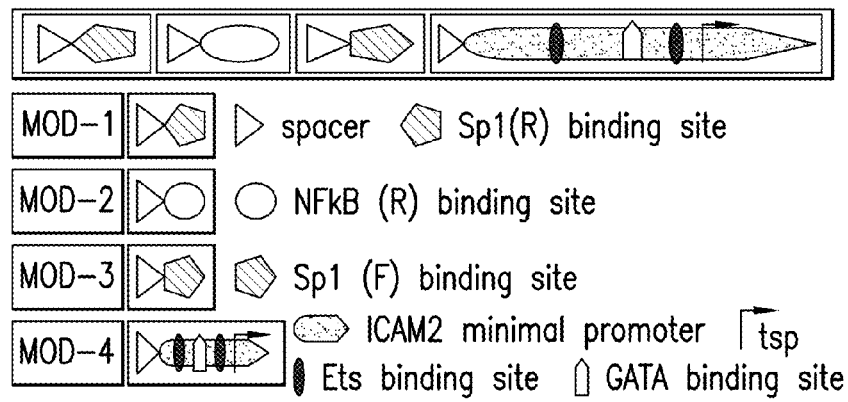
FIGS. 13A-13B show examples of synthetic endothelial cell-specific promoters.
Figure 13B:
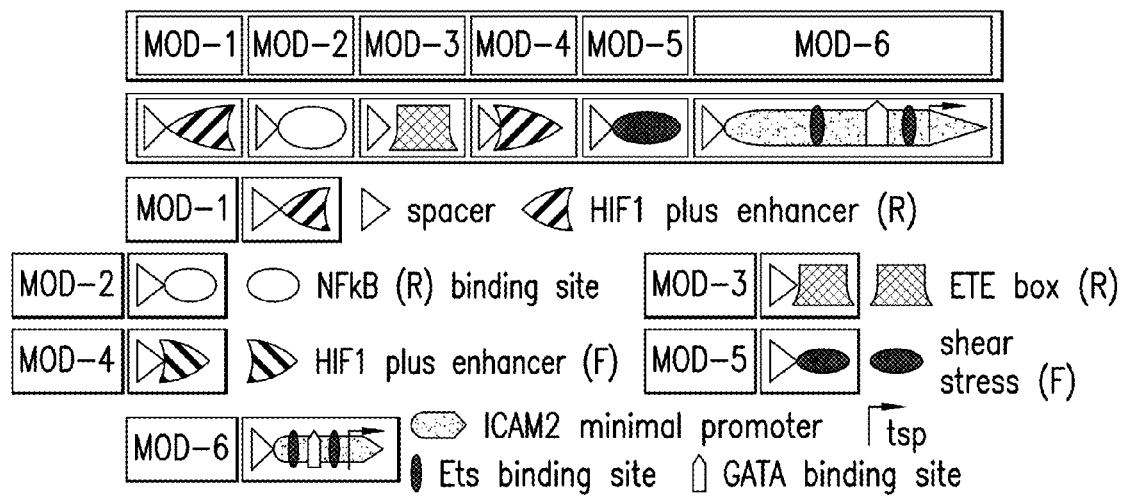

MOD 4399—FLT1, endothelial cell-specific promoter (depicted schematically in FIG. 12B)—MOD Rationale: The human transmembrane fms-like receptor tyrosine kinase Flt-1 is one of the receptors for vascular endothelial growth factor, a growth factor which induces endothelial proliferation and vascular permeability. Flt-1 is expressed specifically in endothelium. The flt-1 promoter will be useful as a tool in targeting the expression of exogenously introduced genes to the endothelium.

MOD 4790—Synthetic endothelial cell-specific promoter 1 (depicted schematically in FIG. 13A) and MOD 4791—Synthetic endothelial cell-specific promoter 2 (depicted schematically in FIG. 13B)—MOD Rationale: A major goal of gene therapy is the introduction of genes of interest into desired cell types. Endothelial cells line essentially all major blood vessels and thus have direct access to the circulatory system. Potential gene products to be delivered via endothelial cells include hormones, protein factors found in plasma such as insulin, growth hormone, factor VIII, as well as angiogenic or angiostatic molecules for the treatment of ischemic or neovascular conditions, respectively. Inspection of promoter regions of endothelial cell-specific genes reveals that most have binding sites for both specific and non-specific transcription factors. The goal of this design was to construct a small synthetic endothelial cell-specific promoter. Sequences of known transcription factor binding sites that are located 5' of many endothelial cell-specific mRNA transcripts were linked to the human ICAM2 minimal promoter to generate a synthetic, endothelial cell-specific promoters 1 and 2.

Examples

Localization Tethers

See 'Description of the Polypeptide and Polynucleotide Sequences' for corresponding SEQ ID NOS of the following exemplary localization tethers.

Figure 14A:
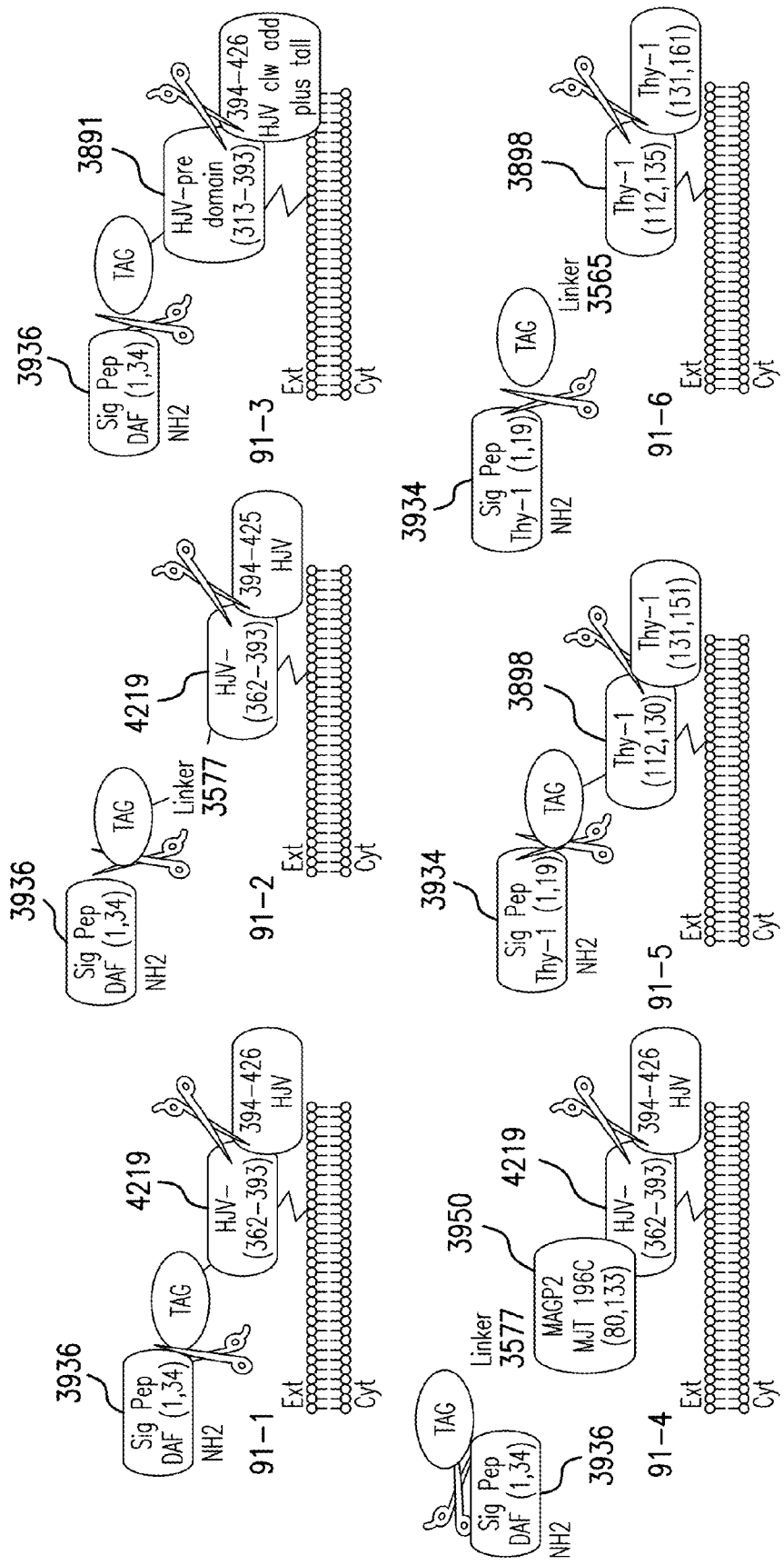
FIGS. 14A-14B show examples of class 1 localization tethers.
Figures 1, 14A:
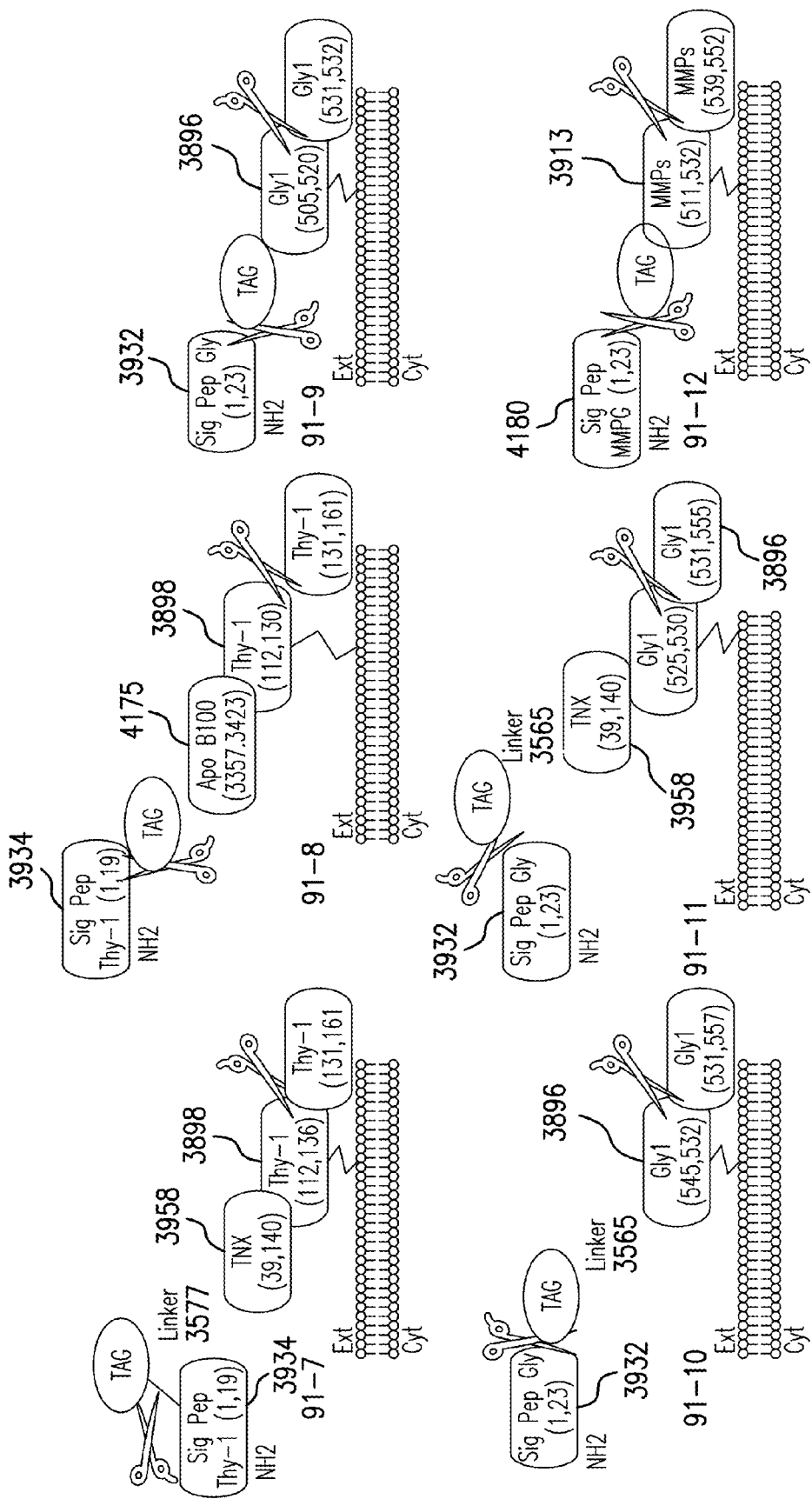
Figure 14B:
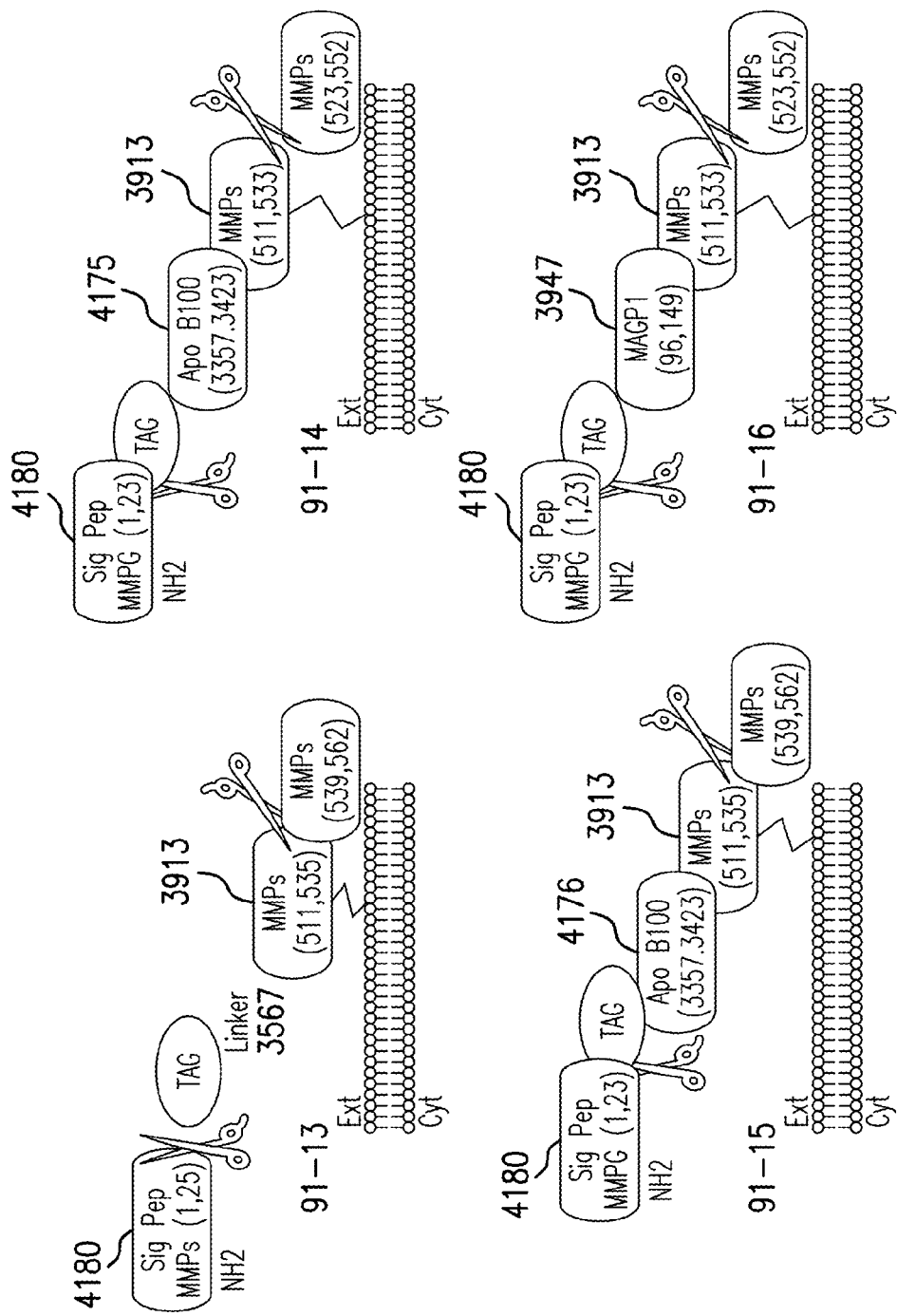
Figures 1, 14B:
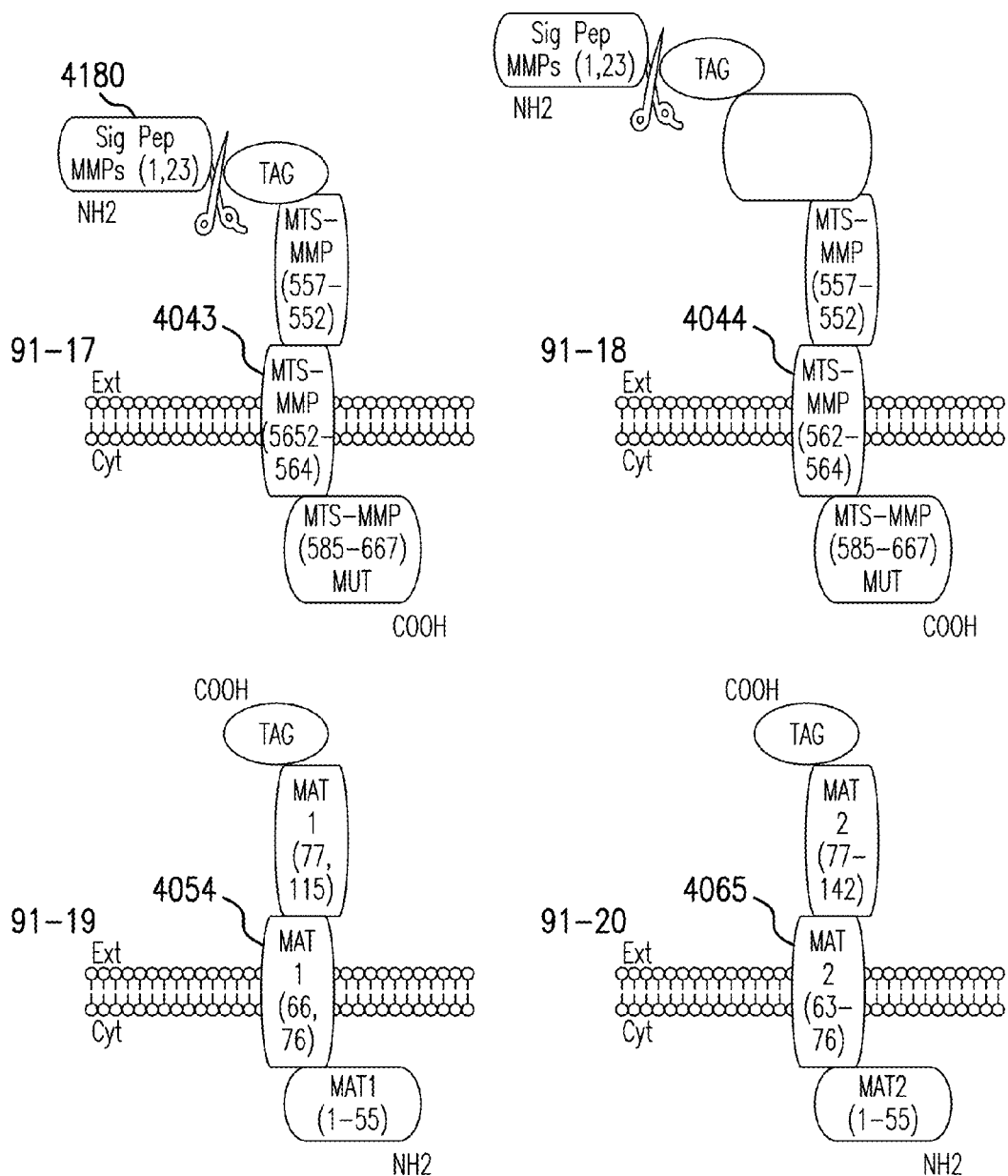

Localization Tethers, Class 1—Lipid-modified, integral to plasma membrane, extracellular (depicted schematically in FIGS. 14A-14B): Localization Tethers, Class 1 are designed to anchor the cargo at the extra-cellular surface of the plasma membrane. They were designed with cardiac, skeletal or fibroblast tissue in mind. The majority of the constructs utilize a glycosylphosphatidylinositol (GPI) lipid modification to anchor to the membrane. GPI biosynthesis occurs post translation in the ER. A hydrophobic motif is recognized in the C-terminal region of the protein and subsequently cleaved. After cleavage, the complete GPI moiety is added to the protein. GPI anchors are diverse in structure and composition and may be protein or tissue specific. Once at the cell surface, GPI anchors are subject to cleavage by phospholipases. The kinetics of GPI cleavage are determined by lipid length, membrane surface charge, and physiochemical properties of the membrane bilayer itself. As such, different GPI anchors were used in the designs to provide an array of surface retention times.

Designs 91-1 through 91-4 contain the hemojuvelin (HJV) GPI-anchor cleavage/addition domain. HJV was chosen because it is expressed in skeletal muscle and if addition of the correct GPI anchor is tissue specific, provides a domain ideal for use in muscle tissue. 91-1 is the basic signal peptide/cargo/GPI motif blueprint. 91-2 provides the addition of a linker between the cargo and the lipid anchor to increase the field of cargo movement. 91-3 contains a longer c-terminal region of HJV containing a mutation that prevents the binding of HJV to neurogenin but has been demonstrated to traffic to the membrane properly. 91-4 is the same as 91-2 but adds in the MAGP1 fibrillin-binding domain. When the GPI anchor is cleaved, this construct is designed to bind surrounding matrix microfibrils. This would keep the cargo in close proximity to matrix modifying proteins.

Designs 91-5 and 91-6 utilize the Thy-1 GPI cleavage/addition site. Thy-1 was chosen because the retention time has been studied and determined to be greater than other GPI anchored proteins. The structure of the Thy-1 anchor may cause a steric hindrance with the phospholipase and decrease the rate of cleavage. 91-7 builds on 91-6 with the addition of a tenascin-X (TNX) matrix-binding domain. This domain should target the cleaved GPI-anchored protein to collagen type I microfibrils. 91-8 also contains a matrix binding domain, but rather than targeting the matrix framework this ApoB domain binds glycosaminoglycans (9637699).

Designs 91-9 through 91-11 follow the same design rationale, but utilize the glypican-1 GPI motif. Glypican-1 is a GPI-anchored proteoglycan localizing to rafts and caveolae. It is widely expressed in different tissues and provides potentially different retention time to the other GPI's in this MDR. 91-12 through 91-16 follow similar rationale but contain the MT-MMP6 GPI cleavage/addition site and different combinations of linkers and matrix binding domains.

Designs 91-17 and 91-18 attempt to create a simple transmembrane LOC which will traffic properly and present the cargo at the extra-cellular face. MT1-MMP C-terminal tail and transmembrane region have no known function other than putative trafficking information. 91-18 adds a glycosylated ectodomain to aid in trafficking if 91-17 is not presented at the membrane. 91-19 and 91-20 achieve cargo placement at the c-terminus. Matriptase is a type II serine protease. The protease domain is in the C-terminal region, which is removed in these constructs. The remaining portion is potentially glycosylated to mediate plasma membrane delivery.

As a whole, designs 91-1 through 91-16 attempt to achieve varying membrane retention times to obtain the ideal cargo presentation tailored to the decoy added. Some designs contain matrix-binding domains to increase the activity of the cargo within the matrix at the site of delivery. Designs 91-17 through 91-20 attempt to achieve the simplest designs possible that possess no intrinsic activity. A potential pitfall for all the designs will be a defect in plasma membrane trafficking.

Localization Tethers, Class 2—Secreted and-or Extracellular, soluble: These localization modules are intended to carry a cargo through the cell by way of either the regulated secretory pathway or the constitutive pathway for release at the cell membrane into the extracellular space. Once outside the cell, binding sequences would allow for attachment of the peptide to the outer leaflet of the plasma membrane of the cell in which it was synthesized, or to proteins forming the extra cellular matrix.

For secretion, three strategies were utilized. In the first, the regulated secretory pathway of the cell is taken advantage of through the use of aggregation and/or binding to the lipids or proteins at the inner face of the granule. In the second, the constitutive secretory pathway is taken advantage of through the use of common signals for entrance into these vesicles. In the third, both pathways are taken advantage of. This was done due to the potential that one or the other pathways becomes "overloaded" under the conditions of the disease state, and the use of two functionally distinct signals should not act as a deterrent for exit of activity of the peptide as a whole. When association with the inner face of the secretory granule was utilized, binding that is sensitive to changes in pH or calcium levels to aid in release of the peptide at the cell surface was chosen.

Once released from the vesicle at the surface, the peptide is then expected to bind either proteins bound at the surface of the outer leaflet of the cell (i.e., uPAR or annexin), or to proteins that comprise the extra cellular matrix (i.e., fibrin). In some of the constructs, protease sites for those enzymes known to be over-expressed within the region of the infarct to cause "exposure" of a "hidden" ECM binding motif were used. In this way, prevention of cargo from being held and active towards proteins within regions of healthy tissue is attempted. In others, the site is placed in a way that the cargo is released from the main body of the localization peptide for release of only itself into the extra cellular matrix. Binding to the ECM is expected to confer "staying power" of the cargo, whereas maintained binding to proteins on the membrane would allow for turnover of our peptide.

Figure 15:
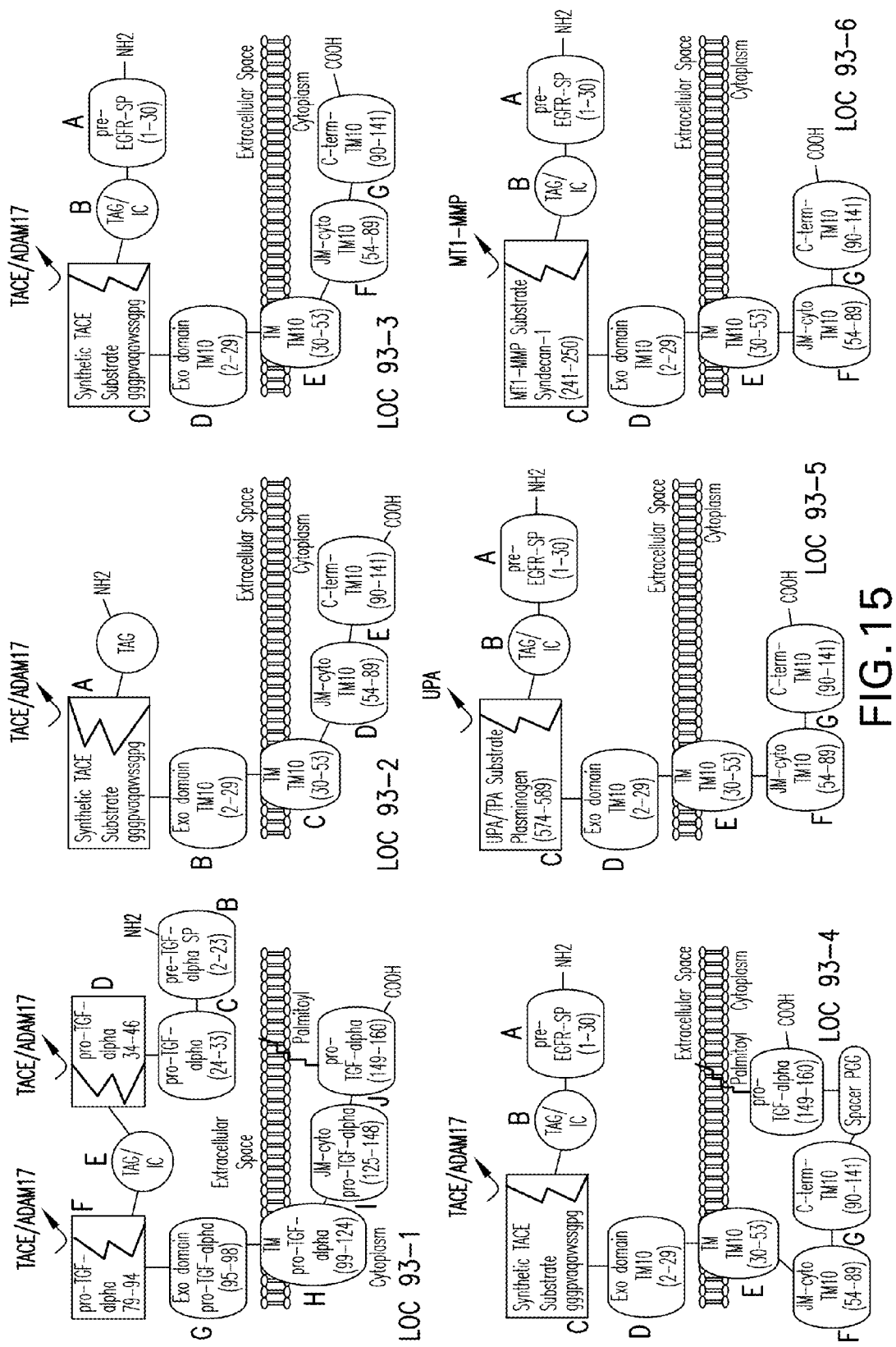
FIG. 15 shows examples of class 3 localization tethers.
Figures 1, 15:
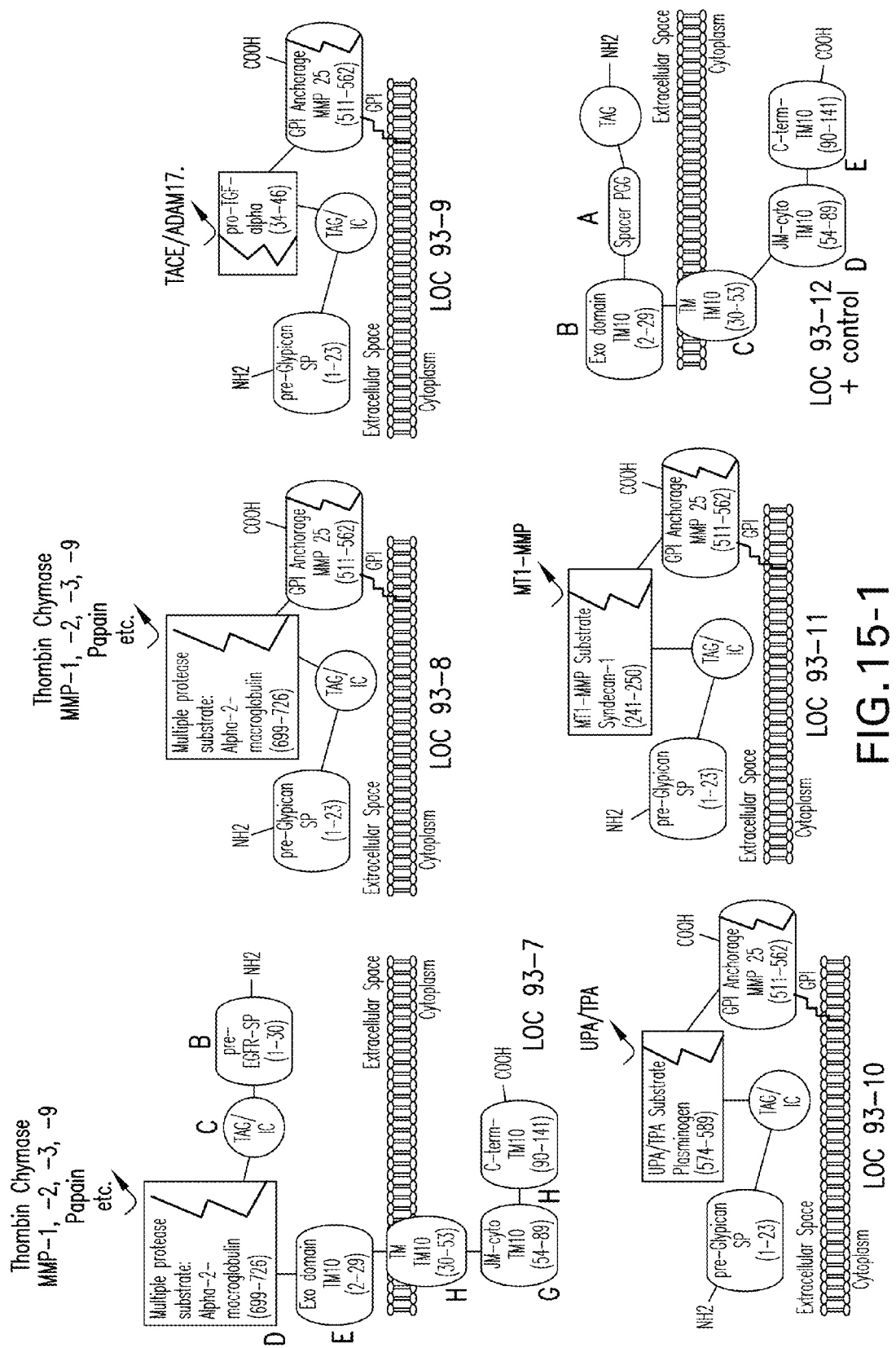
Figure 17A:
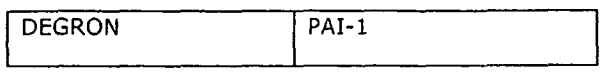
FIGS. 17A-17H show examples of PAI-1 linked to a degron and/or a localization signal.
Figure 17B:
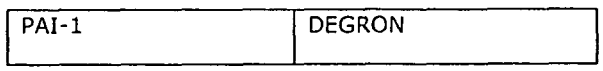
Figure 17C:
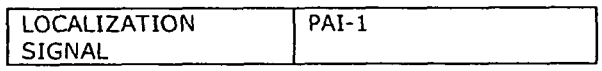
Figure 17D:
Figure 17E:
Figure 17F:
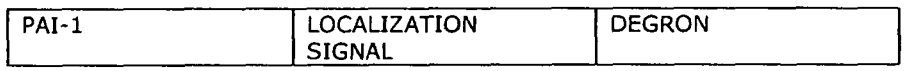
Figure 17G:
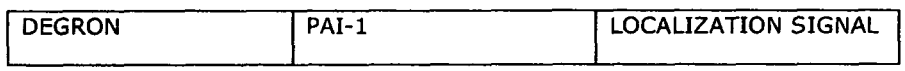
Figure 17H:

Localization Tethers, Class 3—Conditionally soluble extracellular (depicted schematically in FIG. 15): The basic modular elements of this design are as follows: a transmembrane protein (or pre-protein) that is predicted to behave relatively inertly, a well-known signal peptide, lipid membrane attachment motifs (GPI and palmitoyl), and a conditionally cleavable proteolytic site (for TACE/ADAM17, MT1-MMP, uPA/tPA, or a multiple protease cut). These components are varied through the eleven designs and one potential positive control. The design set as a whole attempts to strike a balance between different risk considerations, both experimental and practical.

LOC-93-1 is in a class by itself. It is based on pre-pro-TGF-alpha, but in this design, the secreted and processed growth factor is deleted, and in its stead lies the therapeutic decoy, tag, or fluorescent protein. For this design to "work," the decoy must be processed in much the same way as mature TGF-alpha. Pre-pro-TGF-alpha is largely cleaved and activated by Tumor necrosis factor Alpha Converting Enzyme (TACE/ADAM17), which also is involved in the "shedding" of numerous pro-inflammatory cytokines such as TNF-alpha. TACE is induced by a pro-inflammatory milieu, and can be artificially induced by phorbol ester treatment. TACE is abundant in zones of cardiac injury, tissue remodeling, and tumor microenvironment, and can be active at either the cell surface or even prior to secretion, in secretory vesicles. Other designs in this set that employ TACE (or predicted TACE consensus) cut sites are LOC-93-2, -3, -4, and -9. However, these consensus sites are expected to localize to the surface via different means.

LOC-93-2, -3, -4, -5, -6, -7 and -12 (control) employ a somewhat obscure polypeptide known as TM10, the human homologue of Opalin, a brain-specific protein of unknown function. This protein was identified via searches for small (i.e., <200 amino acids) transmembrane proteins in the EMBL-GFP (Heidelburg, Germany) localization database project. It has no obvious signal peptide, ligand receptor, or kinase domain, and BLAST searches of its 141 amino acid sequence reveal no close homologues. Although the LOCATE database reports TM10 to be a type II membrane protein, multiple analyses of the sequence reveal that it is, in fact, a Type I without exception or ambiguity (including the analysis sites that are linked to via LOCATE). Most recently, after the completion of these designs, TM10 (TMEM10) was characterized by Kippert et al (Apr. 25, 2008; 18439243), and demonstrated experimentally to be a Type I with robust plasma membrane localization and possible actin binding. The rationale for using a small, compact transmembrane-LOCsig nearly speaks for itself, since many of such examples are larger in size and may be more likely to engage in pleiotypic signaling—a potential hazard in a therapeutic. The rationale for employing an oligodendrocyte-specific polypeptide for a cardiac-based therapy is that brain-specific proteins would be less likely to interfere with cardiac-specific processes.

LOC-93-2, -3, and -4 are themed together in a group for the sake of experimental comparison. A chimeric, synthetic TACE substrate (based on TGF-alpha TACE site plus two substitutions from TNF-alpha, flanked by short spacer residues) is fused with TM10 N-terminus, forming the junction between the TAG/DCY and the LOC. LOC-93-3 converts 93-2 into an "internal cargo" via inclusion of an n-terminal signal peptide from EGFR; this tests whether delivery to the surface is enhanced by a signal peptide. LOC-93-4 adds a c-terminal palmitoyl attachment site to LOC-93-3; this addition, in turn tests whether localization and/or retention on the cell surface is enhanced via c-terminal lipidation.

LOC-93-3, -5, -6, -7 may also be themed together in another set to compare different proteolytic sites. The proteolytic cut site may be for TACE/ADAM17, uPA/tPA, MT1-MMP, or a site that is more labile and the target of numerous proteases (i.e., alpha-2 macroglobulin).

LOC-93-8, -9, -10, and -11 are designed as follows. The configuration is a signal peptide (from pre-Glypican) followed by the internal cargo, and ending at the c-terminus with a putative GPI anchorage site (from MMP 25). Like LOC-93-3, -5, -6 and -7, these test four variables of protease cut sites. However, here the context of membrane attachment is different, which is not via transmembrane, but via a single mode of lipidation.

LOC-93-12 is a potential positive control for plasma membrane localization, and has been characterized by the GFP-LOC project out of EMBL-Heidelburg—and more recently, a paper via Kippert et al (Apr. 25, 2008; 18439243).

The present invention also provides the following non-limiting embodiments.

E1. An isolated polypeptide ligand, wherein the ligand modulates PAI-1 activity.

E2. An isolated polypeptide heteropolyligand, wherein the heteropolyligand modulates PAI-1 activity.

E3. An isolated polypeptide homopolyligand, wherein the homopolyligand modulates PAI-1 activity.

E4. An isolated fusion protein, wherein the fusion protein comprises one or more fragments of a parent protein that has at least one putative PAI-1 interaction domain recognition motif.

E5. The isolated fusion protein of E4, wherein the parent protein is fibrin, tissue plasminogen activator, urokinase plasminogen activator, or vitronectin.

E6. The polypeptide of E1-E5, further comprising one or more of a degron, a localization signal, an epitope, or a reporter.

E7. An isolated polynucleotide comprising a nucleotide sequence encoding the polypeptide of each of E1-E7.

E8. A vector comprising a polynucleotide of E7.

E9. A host cell comprising a polynucleotide E7.

E10. A non-human organism comprising a polynucleotide of E7.

E11. The polynucleotide of E7 operably linked to a promoter.

E12. The polynucleotide operably linked to a promoter of E11, wherein the promoter is a constitutive promoter, a non-specific promoter, an inducible promoter, or a tissue-specific promoter.

E13. The polynucleotide operably linked to a promoter of E12, wherein the tissue-specific promoter is an endothelial cell-specific promoter, a vascular smooth muscle cell-specific promoter, a cardiomyocyte-specific promoter, a coronary adipocytes-specific promoter, or a cardiac fibroblast-specific promoter.

E14. The host cell of E9, wherein the host cell is a mammalian cell.

E15. The host cell of E14, wherein the host cell is an endothelial cell, a vascular smooth muscle cell, a cardiomyocyte, a coronary adipocyte, or a cardiac fibroblast.

E16. The non-human organism of E10, wherein the organism is a non-human primate, mouse, cow, pig, sheep, horse, rat, rabbit, dog, cat, or guinea pig.

E17. A method of inhibiting PAI-1 in a cell comprising transfecting a vector of E8 into a host cell and culturing the transfected host cell under conditions suitable to produce at least one copy of the polypeptide.

E18. A method of inhibiting PAI-1 in heart tissue of a subject comprising injecting a vector of E 8 into heart tissue of a subject.

E19. A method of creating a transgenic subject with reduced PAI-1 activity comprising injecting a vector of E8 into a fertilized egg.

E20. An isolated fusion protein, wherein the fusion protein comprises PAI-1 linked to a degron.

E21. An isolated fusion protein, wherein the fusion protein comprises PAI-1 linked to a localization signal.

E22. An isolated fusion protein, wherein the fusion protein comprises PAI-1 linked to a degron and a localization signal.

E23. An isolated polynucleotide comprising a nucleotide sequence encoding the polypeptide of each of E20-E22.

E24. An isolated polynucleotide comprising a nucleotide sequence encoding PAI-1 that has been optimized for vector insertion.

E25. The isolated polynucleotide of E24, wherein the vector is ULTRAVECTOR.

E26. A vector comprising a polynucleotide of E23-E25.

E27. A host cell comprising a polynucleotide of E23-E25

E28. A non-human organism comprising a polynucleotide of E23-E25.

E29. The polynucleotide of E23-E25 operably linked to a promoter.

E30. The polynucleotide operably linked to a promoter of E29, wherein the promoter is a constitutive promoter, a non-specific promoter, an inducible promoter, or a tissue-specific promoter.

E31. The polynucleotide operably linked to a promoter of E29, wherein the tissue-specific promoter is an endothelial cell-specific promoter, a vascular smooth muscle cell-specific promoter, a cardiomyocyte-specific promoter, a coronary adipocytes-specific promoter, or a cardiac fibroblast-specific promoter.

E32. The host cell of E27, wherein the host cell is a mammalian cell.

E33. The host cell of E32, wherein the host cell is an endothelial cell, a vascular smooth muscle cell, a cardiomyocyte, a coronary adipocyte, or a cardiac fibroblast.

E34. The non-human organism of E28, wherein the organism is a non-human primate, mouse, cow, pig, sheep, horse, rat, rabbit, dog, cat, or guinea pig.

E35. A method of altering expression of PAI-1 in a host cell comprising transfecting a vector of E26 into a host cell and culturing the transfected host cell under conditions suitable to produce at least one copy of PAI-1.

E36. A method of altering expression of PAI-1 in heart tissue of a subject comprising injecting a vector of E26 into heart tissue of a subject.

E37. A method of creating a transgenic subject with altered PAI-1 expression comprising injecting a vector of E26 into a fertilized egg.

The previous examples and embodiments are intended to serve as illustrative embodiments. It will be understood by those of ordinary skill in the art that the invention is not limited to the particular embodiments described herein, and that a wide range of equivalent designs fall within the scope of the invention.

REFERENCES

Akyurek, L. M., S, Nallamshetty, et al. (2001). "Coexpression of guanylate kinase with thymidine kinase enhances prodrug cell killing in vitro and suppresses vascular smooth muscle cell proliferation in vivo." *Mol Ther* 3 (5 Pt 1): 779-86.

Akyurek, L. M., Z. Y. Yang, et al. (2000). "SM22alpha promoter targets gene expression to vascular smooth muscle cells in vitro and in vivo." *Mol Med* 6 (11): 983-91.

Appleby, C. E., P. A. Kingston, et al. (2003). "A novel combination of promoter and enhancers increases transgene expression in vascular smooth muscle cells in vitro and coronary arteries in vivo after adenovirus-mediated gene transfer." *Gene Ther* 10 (18): 1616-22.

Beck, C., H. Uramoto, et al. (2004). "Tissue-specific targeting for cardiovascular gene transfer. Potential vectors and future challenges." *Curr Gene Ther* 4 (4): 457-67.

Burke, B. (2003). "Macrophages as novel cellular vehicles for gene therapy." *Expert Opin Biol Ther* 3 (6): 919-24.

Burke, B., S. Sumner, et al. (2002). "Macrophages in gene therapy: cellular delivery vehicles and in vivo targets." *J Leukoc Biol* 72 (3): 417-28.

Gough, P. J. and E. W. Raines (2003). "Gene therapy of apolipoprotein E-deficient mice using a novel macrophage-specific retroviral vector." *Blood* 101 (2): 485-91.

Hasty, A. H., M. F. Linton, et al. (1999). "Retroviral gene therapy in ApoE-deficient mice: ApoE expression in the artery wall reduces early foam cell lesion formation." *Circulation* 99 (19): 2571-6.

Ishiguro, H., H. Yoshida, et al. (2001). "Retrovirus-mediated expression of apolipoprotein A-I in the macrophage protects against atherosclerosis in vivo." *J Biol Chem* 276 (39): 36742-8.

Juan, S. H., T. S. Lee, et al. (2001). "Adenovirus-mediated heme oxygenase-1 gene transfer inhibits the development of atherosclerosis in apolipoprotein E-deficient mice." *Circulation* 104 (13): 1519-25.

Lu, Z. Z., F. Ni, et al. (2006). "Efficient gene transfer into hematopoietic cells by a retargeting adenoviral vector system with a chimeric fiber of adenovirus serotype 5 and 11p." *Exp Hematol* 34 (9): 1171-82.

Nilsson, M., S. Karlsson, et al. (2004). "Functionally distinct subpopulations of cord blood CD34+ cells are transduced by adenoviral vectors with serotype 5 or 35 tropism." *Mol Ther* 9 (3): 377-88.

Ophorst, O. J., S. Kostense, et al. (2004). "An adenoviral type 5 vector carrying a type 35 fiber as a vaccine vehicle: DC targeting, cross neutralization, and immunogenicity." *Vaccine* 22 (23-24): 3035-44.

Roth, D. M., N. C. Lai, et al. (2004). "Indirect intracoronary delivery of adenovirus encoding adenylyl cyclase increases left ventricular contractile function in mice." *Am J Physiol Heart Circ Physiol* 287 (1): H172-7.

Segerman, A., K. Lindman, et al. (2006). "Adenovirus types 11p and 35 attach to and infect primary lymphocytes and monocytes, but hexon expression in T-cells requires prior activation." *Virology* 349 (1): 96-111.

Shayakhmetov, D. M., T. Papayannopoulou, et al. (2000). "Efficient gene transfer into human CD34(+) cells by a retargeted adenovirus vector." *J Virol* 74 (6): 2567-83.

Van Eck, M., N. Herijgers, et al. (2000). "Effect of macrophage-derived mouse ApoE, human ApoE3-Leiden, and human ApoE2 (Arg158→Cys) on cholesterol levels and atherosclerosis in ApoE-deficient mice." *Arterioscler Thromb Vasc Biol* 20 (1): 119-27.

Yoshida, H., A. H. Hasty, et al. (2001). "Isoform-specific effects of apolipoprotein E on atherogenesis: gene transduction studies in mice." *Circulation* 104 (23): 2820-5.

---

What is claimed is:

1. An isolated polynucleotide encoding a polypeptide comprising an amino acid sequence that is at least 95% identical to SEQ ID NO: 27; wherein, said amino acid sequence, that is at least 95% identical to SEQ ID NO: 27, inhibits PAI-1 activity.

2. The isolated polynucleotide of claim 1, wherein said amino acid sequence that is at least 95% identical to SEQ ID NO: 27 is at least 96% identical to SEQ ID NO: 27.

3. The isolated polynucleotide of claim 1, wherein said amino acid sequence that is at least 95% identical to SEQ ID NO: 27 is at least 97% identical to SEQ ID NO: 27.

4. The isolated polynucleotide of claim 1, wherein said amino acid sequence that is at least 95% identical to SEQ ID NO: 27 is at least 98% identical to SEQ ID NO: 27.

5. The isolated polynucleotide of claim 1, wherein said amino acid sequence that is at least 95% identical to SEQ ID NO: 27 is at least 99% identical to SEQ ID NO: 27.

6. The isolated polynucleotide of claim 1, wherein said amino acid sequence that is at least 95% identical to SEQ ID NO: 27 is SEQ ID NO: 27.

* * * * *

SEQUENCE LISTING

```
<160> NUMBER OF SEQ ID NOS: 139

<210> SEQ ID NO 1
<211> LENGTH: 68
<212> TYPE: PRT
<213> ORGANISM: Artificial
<220> FEATURE:
<223> OTHER INFORMATION: synthetic

<400> SEQUENCE: 1

Leu Gln Ile Asp Ser Gly Thr Val Ala Ser Ser Ser Thr Ala Val Ile
1               5                   10                  15

Val Ser Ala Ser Gly Thr Val Ala Ser Ser Ser Thr Ala Val Ile Val
            20                  25                  30

Ser Ala Ser Gly Thr Val Ala Ser Ser Ser Thr Ala Val Ile Val Ser
        35                  40                  45

Ala Ser Gly Thr Val Ala Ser Ser Ser Thr Ala Val Ile Val Ser Ala
    50                  55                  60

Leu Gln Ile Asp
65

<210> SEQ ID NO 2
<211> LENGTH: 204
<212> TYPE: DNA
<213> ORGANISM: Artificial
<220> FEATURE:
<223> OTHER INFORMATION: synthetic

<400> SEQUENCE: 2
ctgcaaatcg acagcggaac cgtcgcctcc agctccaccg ctgtgattgt gtccgcctcc      60
ggcacagtgg cctcctccag cacagccgtc atcgtcagcg ccagcggcac cgtggccagc     120
agcagcaccg ccgtgatcgt gagcgccagc ggcacagtcg cttcctcctc cacagctgtc     180
attgtctccg ctctccagat tgac                                            204

<210> SEQ ID NO 3
<211> LENGTH: 52
<212> TYPE: PRT
<213> ORGANISM: Artificial
<220> FEATURE:
<223> OTHER INFORMATION: synthetic
```

<400> SEQUENCE: 3

Leu Gln Ile Asp Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Leu Gln Ile Asp
    50

<210> SEQ ID NO 4
<211> LENGTH: 156
<212> TYPE: DNA
<213> ORGANISM: Artificial
<220> FEATURE:
<223> OTHER INFORMATION: synthetic

<400> SEQUENCE: 4
ctgcaaatcg acgaccaaga gtcctgcaaa ggcagatgca cagagggatt caatgtggat      60
aagaaatgcc aatgcgatga gctgtgctcc tactatcagt cctgctgtac cgattacaca    120
gccgaatgca aaccccaagt gacactccag attgac                              156

<210> SEQ ID NO 5
<211> LENGTH: 104
<212> TYPE: PRT
<213> ORGANISM: Artificial
<220> FEATURE:
<223> OTHER INFORMATION: synthetic

<400> SEQUENCE: 5

Leu Gln Ile Asp Ser Gly Thr Val Ala Ser Ser Thr Ala Val Ile
1               5                   10                  15

Val Ser Ala Ser Asp Val Thr Gly Asn Ala Thr Tyr Thr Ile Thr Ser
            20                  25                  30

Gly Thr Val Ala Ser Ser Thr Ala Val Ile Val Ser Ala Ser Asp
        35                  40                  45

Val Thr Gly Asn Ala Thr Tyr Thr Ile Thr Ser Gly Thr Val Ala Ser
    50                  55                  60

Ser Ser Thr Ala Val Ile Val Ser Ala Ser Asp Val Thr Gly Asn Ala
65                  70                  75                  80

Thr Tyr Thr Ile Thr Ser Gly Thr Val Ala Ser Ser Thr Ala Val
                85                  90                  95

Ile Val Ser Ala Leu Gln Ile Asp
            100

<210> SEQ ID NO 6
<211> LENGTH: 312
<212> TYPE: DNA
<213> ORGANISM: Artificial
<220> FEATURE:
<223> OTHER INFORMATION: synthetic

<400> SEQUENCE: 6
ctgcaaatcg acagcggaac cgtcgcctcc agctccaccg ctgtgattgt gtccgccagc      60
gatgtgacag gcaatgccac atacacaatc acatccggca cagtggccag ctccagcaca    120
gccgtcatcg tcagcgcttc cgacgtgacc ggaaacgcta cctataccat taccagcggc    180
accgtggcca gcagcagcac cgccgtgatc gtgagcgcca gcgacgtgac cggcaacgcc    240

```
acctacacca tcaccagcgg cacagtcgct tcctcctcca cagctgtcat tgtctccgct      300
ctccagattg ac                                                         312
```

<210> SEQ ID NO 7
<211> LENGTH: 33
<212> TYPE: PRT
<213> ORGANISM: Artificial
<220> FEATURE:
<223> OTHER INFORMATION: synthetic

<400> SEQUENCE: 7

```
Leu Gln Ile Asp Lys Phe Ser Leu Glu Thr Glu Val Asp Leu Asn Pro
1               5                   10                  15

Ala Gly Ala Leu Gln Lys Val Lys Ile Glu Val Asn Glu Leu Gln Ile
            20                  25                  30

Asp
```

<210> SEQ ID NO 8
<211> LENGTH: 99
<212> TYPE: DNA
<213> ORGANISM: Artificial
<220> FEATURE:
<223> OTHER INFORMATION: synthetic

<400> SEQUENCE: 8

```
ctgcaaatcg acaagtttag cctggagaca gaggtggacc tcaaccctgc cggagccctc      60
cagaaagtga aaatcgaagt gaatgagctg caaattgac                            99
```

<210> SEQ ID NO 9
<211> LENGTH: 101
<212> TYPE: PRT
<213> ORGANISM: Artificial
<220> FEATURE:
<223> OTHER INFORMATION: synthetic

<400> SEQUENCE: 9

```
Leu Gln Ile Asp Thr Val Ser His Glu Val Ala Asp Cys Ser His Leu
1               5                   10                  15

Lys Leu Thr Gln Val Pro Asp Asp Leu Pro Thr Asn Ile Thr Ala Leu
            20                  25                  30

Tyr Leu Asn His Asn Gln Leu Arg Arg Leu Pro Ala Ala Asn Phe Thr
        35                  40                  45

Arg Tyr Ser Gln Leu Thr Lys Leu Lys Val Glu Phe Asn Thr Ile Ser
    50                  55                  60

Lys Leu Glu Pro Glu Leu Cys Gln Lys Leu Pro Met Leu Lys Val Leu
65                  70                  75                  80

Asn Leu Gln His Asn Glu Leu Ser Gln Leu Ser Asp Lys Thr Phe Ala
                85                  90                  95

Phe Leu Gln Ile Asp
            100
```

<210> SEQ ID NO 10
<211> LENGTH: 303
<212> TYPE: DNA
<213> ORGANISM: Artificial
<220> FEATURE:
<223> OTHER INFORMATION: synthetic

<400> SEQUENCE: 10

```
ctgcaaatcg acaccgtcag ccatgaggtc gccgattgct cccacctcaa gctgacccag      60
gtgcctgacg atctgcctac caatatcaca gccctctacc tcaaccataa ccaactgagg     120
```

```
agactcccg ctgccaattt cacaagatat agccaactga caaagctcaa ggtcgagttt    180
aacacaatct ccaagctgga gcctgagctg tgccaaaagc tccccatgct gaaagtgctc    240
aacctccagc ataacgaact gtcccagctg tccgataaga cattcgcttt cctccagatt    300
gac                                                                  303
```

```
<210> SEQ ID NO 11
<211> LENGTH: 240
<212> TYPE: PRT
<213> ORGANISM: Artificial
<220> FEATURE:
<223> OTHER INFORMATION: synthetic

<400> SEQUENCE: 11
```

```
Leu Gln Ile Asp Ile Val Gly Gly Trp Glu Cys Glu Lys His Ser Gln
1               5                   10                  15

Pro Trp Gln Val Ala Val Tyr Ser His Gly Trp Ala His Cys Gly Gly
            20                  25                  30

Val Leu Val His Pro Gln Trp Val Leu Thr Ala Ala His Cys Leu Lys
        35                  40                  45

Lys Asn Ser Gln Val Trp Leu Gly Arg His Asn Leu Phe Glu Pro Glu
    50                  55                  60

Asp Thr Gly Gln Arg Val Pro Val Ser His Ser Phe Pro His Pro Leu
65                  70                  75                  80

Tyr Asn Met Ser Leu Leu Lys His Gln Ser Leu Arg Pro Asp Glu Asp
                85                  90                  95

Ser Ser His Asp Leu Met Leu Leu Arg Leu Ser Glu Pro Ala Lys Ile
            100                 105                 110

Thr Asp Val Val Lys Val Leu Gly Leu Pro Thr Gln Glu Pro Ala Leu
        115                 120                 125

Gly Thr Thr Cys Tyr Ala Ser Gly Trp Gly Ser Ile Glu Pro Glu Glu
    130                 135                 140

Phe Leu Arg Pro Arg Ser Leu Gln Cys Val Ser Leu His Leu Leu Ser
145                 150                 155                 160

Asn Asp Met Cys Ala Arg Ala Tyr Ser Glu Lys Val Thr Glu Phe Met
                165                 170                 175

Leu Cys Ala Gly Leu Trp Thr Gly Gly Lys Asp Thr Cys Gly Gly Asp
            180                 185                 190

Ser Gly Gly Pro Leu Val Cys Asn Gly Val Leu Gln Gly Ile Thr Ser
        195                 200                 205

Trp Gly Pro Glu Pro Cys Ala Leu Pro Glu Lys Pro Ala Val Tyr Thr
    210                 215                 220

Lys Val Val His Tyr Arg Lys Trp Ile Lys Asp Thr Leu Gln Ile Asp
225                 230                 235                 240
```

```
<210> SEQ ID NO 12
<211> LENGTH: 720
<212> TYPE: DNA
<213> ORGANISM: Artificial
<220> FEATURE:
<223> OTHER INFORMATION: synthetic

<400> SEQUENCE: 12
```

```
ctgcaaatcg acatcgtcgg cggatgggaa tgcgaaaagc atagccaacc ctggcaagtg    60
gccgtctact cccacggatg ggctcactgt ggcggagtgc tcgtgcatcc ccaatgggtc    120
ctgacagccg ctcactgtct gaaaaagaat agccaagtgt ggctgggcag acacaacctg    180
```

```
ttcgagcccg aggacacagg ccaaagagtc cccgtcagcc atagctttcc ccatcccctc    240
tacaatatgt ccctgctcaa gcatcagtcc ctgaggcccg atgaggatag ctcccacgat    300
ctgatgctgc tcagactcag cgaacccgct aagattaccg atgtggtcaa ggtcctggga    360
ctgcctaccc aagagcctgc cctcggcaca acctgttacg ccagcggatg gggaagcatt    420
gagcctgagg agtttctcag acctagatcc ctgcaatgcg tcagcctcca cctcctgtcc    480
aacgatatgt gtgccagggc ctatagcgaa aaggtcaccg agttcatgct gtgtgccgga    540
ctgtggaccg gaggcaaaga cacatgcgga ggcgatagcg gaggccctct ggtctgcaat    600
ggcgtcctgc aaggcattac ctcctgggga cccgaaccct gtgccctccc cgaaaagcct    660
gccgtctaca caaaggtcgt gcattacagg aagtggatca agacacact ccagattgac     720
```

<210> SEQ ID NO 13
<211> LENGTH: 254
<212> TYPE: PRT
<213> ORGANISM: Artificial
<220> FEATURE:
<223> OTHER INFORMATION: synthetic

<400> SEQUENCE: 13

```
Leu Gln Ile Asp Ile Val Gly Gly Trp Glu Cys Glu Lys His Ser Gln
1               5                   10                  15

Pro Trp Gln Val Ala Val Tyr Ser Lys His Arg Arg Ser Pro Gly Glu
            20                  25                  30

Trp Ala His Cys Gly Gly Val Leu Val His Pro Gln Trp Val Leu Thr
        35                  40                  45

Ala Ala His Cys Leu Lys Lys Asn Ser Gln Val Trp Leu Gly Arg His
    50                  55                  60

Asn Leu Phe Glu Pro Glu Asp Thr Gly Gln Arg Val Pro Val Ser His
65                  70                  75                  80

Ser Phe Pro His Pro Leu Tyr Asn Met Ser Leu Leu Lys His Gln Ser
                85                  90                  95

Leu Arg Pro Asp Glu Asp Ser Ser His Asp Leu Met Leu Leu Arg Leu
            100                 105                 110

Ser Glu Pro Ala Lys Ile Thr Asp Val Val Lys Val Leu Gly Leu Pro
        115                 120                 125

Thr Gln Glu Pro Ala Leu Gly Thr Thr Cys Tyr Ala Ser Gly Trp Gly
    130                 135                 140

Ser Ile Glu Pro Glu Glu Phe Leu Arg Pro Arg Ser Leu Gln Cys Val
145                 150                 155                 160

Ser Leu His Leu Leu Ser Asn Asp Met Cys Ala Arg Ala Tyr Ser Glu
                165                 170                 175

Lys Val Thr Glu Phe Met Leu Cys Ala Gly Leu Trp Thr Gly Gly Lys
            180                 185                 190

Asp Thr Cys Gly Gly Asp Ser Gly Gly Pro Leu Val Cys Asn Gly Val
        195                 200                 205

Leu Gln Gly Ile Thr Ser Trp Gly Pro Glu Pro Cys Ala Leu Pro Glu
    210                 215                 220

Lys Pro Ala Val Tyr Thr Lys Val Val His Tyr Arg Lys Trp Ile Lys
225                 230                 235                 240

Asp Thr Ser Asp Val Thr Gly Asn Ala Thr Tyr Thr Ile Thr
                245                 250
```

<210> SEQ ID NO 14
<211> LENGTH: 762
<212> TYPE: DNA

-continued

<210> SEQ ID NO 14 (context)
<213> ORGANISM: Artificial
<220> FEATURE:
<223> OTHER INFORMATION: synthetic

<400> SEQUENCE: 14

```
ctgcaaatcg acatcgtcgg cggatgggaa tgcgaaaagc atagccaacc ctggcaagtg      60
gccgtctact ccaagcatag aaggagccct ggcgaatggg ctcactgtgg cggagtgctc     120
gtgcatcccc aatgggtcct gacagccgct cactgtctga aaaagaatag ccaagtgtgg     180
ctgggcagac acaacctgtt cgagcccgag acacaggcc aaagagtccc cgtcagccat      240
agctttcccc atcccctcta caatatgtcc ctgctcaagc atcagtccct gaggcccgat     300
gaggatagct cccacgatct gatgctgctc agactcagcg aacccgctaa gattaccgat     360
gtggtcaagg tcctgggact gcctacccaa gagcctgccc tcggcacaac ctgttacgcc     420
agcggatggg gaagcattga gcctgaggag tttctcagac ctagatccct gcaatgcgtc     480
agcctccacc tcctgtccaa cgatatgtgt gccagggcct atagcgaaaa ggtcaccgag     540
ttcatgctgt gtgccggact gtggaccgga ggcaaagaca catgcggagg cgatagcgga     600
ggccctctgg tctgcaatgg cgtcctgcaa ggcattacct cctggggacc cgaaccctgt     660
gccctccccg aaaagcctgc cgtctacaca aaggtcgtgc attacaggaa gtggatcaaa     720
gacacaagcg atgtgacagg caatgccaca tacacaatca ca                       762
```

<210> SEQ ID NO 15
<211> LENGTH: 112
<212> TYPE: PRT
<213> ORGANISM: Artificial
<220> FEATURE:
<223> OTHER INFORMATION: synthetic

<400> SEQUENCE: 15

```
Leu Gln Ile Asp Asp Gln Glu Ser Cys Lys Gly Arg Cys Thr Glu Gly
1               5                   10                  15
Phe Asn Val Asp Lys Lys Cys Gln Cys Asp Glu Leu Cys Ser Tyr Tyr
                20                  25                  30
Gln Ser Cys Cys Thr Asp Tyr Thr Ala Glu Cys Lys Pro Gln Val Thr
            35                  40                  45
Ser Gly Thr Val Ala Ser Ser Ser Thr Ala Val Ile Val Ser Ala Ser
        50                  55                  60
Gly Thr Val Ala Ser Ser Ser Thr Ala Val Ile Val Ser Ala Ser Gly
65                  70                  75                  80
Thr Val Ala Ser Ser Ser Thr Ala Val Ile Val Ser Ala Ser Gly Thr
                85                  90                  95
Val Ala Ser Ser Ser Thr Ala Val Ile Val Ser Ala Leu Gln Ile Asp
            100                 105                 110
```

<210> SEQ ID NO 16
<211> LENGTH: 336
<212> TYPE: DNA
<213> ORGANISM: Artificial
<220> FEATURE:
<223> OTHER INFORMATION: synthetic

<400> SEQUENCE: 16

```
ctgcaaatcg acgaccaaga gtcctgcaaa ggcagatgca cagagggatt caatgtggat     60
aagaaatgcc aatgcgatga gctgtgctcc tactatcagt cctgctgtac cgattacaca    120
gccgaatgca aacccaagt gacaagcgga accgtcgcct ccagctccac cgctgtgatt     180
gtgtccgcct ccggcacagt ggcctcctcc agcacagccg tcatcgtcag cgccagcggc    240
```

```
accgtggcca gcagcagcac cgccgtgatc gtgagcgcca gcggcacagt cgcttcctcc    300
tccacagctg tcattgtctc cgctctccag attgac                              336
```

<210> SEQ ID NO 17
<211> LENGTH: 112
<212> TYPE: PRT
<213> ORGANISM: Artificial
<220> FEATURE:
<223> OTHER INFORMATION: synthetic

<400> SEQUENCE: 17

```
Leu Gln Ile Asp Asp Gln Glu Ser Cys Lys Gly Arg Cys Thr Glu Gly
1               5                   10                  15

Leu Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Ser Gly Thr Val Ala Ser Ser Ser Thr Ala Val Ile Val Ser Ala Ser
    50                  55                  60

Gly Thr Val Ala Ser Ser Ser Thr Ala Val Ile Val Ser Ala Ser Gly
65                  70                  75                  80

Thr Val Ala Ser Ser Ser Thr Ala Val Ile Val Ser Ala Ser Gly Thr
                85                  90                  95

Val Ala Ser Ser Ser Thr Ala Val Ile Val Ser Ala Leu Gln Ile Asp
            100                 105                 110
```

<210> SEQ ID NO 18
<211> LENGTH: 336
<212> TYPE: DNA
<213> ORGANISM: Artificial
<220> FEATURE:
<223> OTHER INFORMATION: synthetic

<400> SEQUENCE: 18

```
ctgcaaatcg acgaccaaga gtcctgcaaa ggcagatgca cagagggact gaatgtggat    60
aagaaatgcc aatgcgatga gctgtgctcc tactatcagt cctgctgtac cgattacaca   120
gccgaatgca aaccccaagt gacaagcgga accgtcgcct ccagctccac cgctgtgatt   180
gtgtccgcct ccggcacagt ggcctcctcc agcacagccg tcatcgtcag cgccagcggc   240
accgtggcca gcagcagcac cgccgtgatc gtgagcgcca gcggcacagt cgcttcctcc   300
tccacagctg tcattgtctc cgctctccag attgac                              336
```

<210> SEQ ID NO 19
<211> LENGTH: 112
<212> TYPE: PRT
<213> ORGANISM: Artificial
<220> FEATURE:
<223> OTHER INFORMATION: synthetic

<400> SEQUENCE: 19

```
Leu Gln Ile Asp Asp Gln Glu Ser Cys Lys Gly Arg Cys Ala Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Ser Gly Thr Val Ala Ser Ser Ser Thr Ala Val Ile Val Ser Ala Ser
    50                  55                  60
```

Gly Thr Val Ala Ser Ser Thr Ala Val Ile Val Ser Ala Ser Gly
65                  70                  75                  80

Thr Val Ala Ser Ser Thr Ala Val Ile Val Ser Ala Ser Gly Thr
                85                  90                  95

Val Ala Ser Ser Thr Ala Val Ile Val Ser Ala Leu Gln Ile Asp
            100                 105                 110

<210> SEQ ID NO 20
<211> LENGTH: 336
<212> TYPE: DNA
<213> ORGANISM: Artificial
<220> FEATURE:
<223> OTHER INFORMATION: synthetic

<400> SEQUENCE: 20
ctgcaaatcg acgaccaaga gtcctgcaaa ggcagatgcg ccgagggctt caatgtggat      60
aagaaatgcc aatgcgatga gctgtgctcc tactatcagt cctgctgtac cgattacaca     120
gccgaatgca aacccaagt gacaagcgga accgtcgcct ccagctccac cgctgtgatt     180
gtgtccgcct ccggcacagt ggcctcctcc agcacagccg tcatcgtcag cgccagcggc     240
accgtggcca gcagcagcac cgccgtgatc gtgagcgcca gcggcacagt cgcttcctcc     300
tccacagctg tcattgtctc cgctctccag attgac                              336

<210> SEQ ID NO 21
<211> LENGTH: 112
<212> TYPE: PRT
<213> ORGANISM: Artificial
<220> FEATURE:
<223> OTHER INFORMATION: synthetic

<400> SEQUENCE: 21

Leu Gln Ile Asp Asp Gln Glu Ser Cys Lys Gly Arg Cys Thr Glu Gly
1               5                   10                  15

Phe Asn Val Asp Lys Lys Cys Gln Cys Asp Ala Leu Cys Ser Tyr Tyr
                20                  25                  30

Gln Ser Cys Cys Thr Asp Tyr Thr Ala Glu Cys Lys Pro Gln Val Thr
            35                  40                  45

Ser Gly Thr Val Ala Ser Ser Ser Thr Ala Val Ile Val Ser Ala Ser
        50                  55                  60

Gly Thr Val Ala Ser Ser Ser Thr Ala Val Ile Val Ser Ala Ser Gly
65                  70                  75                  80

Thr Val Ala Ser Ser Ser Thr Ala Val Ile Val Ser Ala Ser Gly Thr
                85                  90                  95

Val Ala Ser Ser Ser Thr Ala Val Ile Val Ser Ala Leu Gln Ile Asp
            100                 105                 110

<210> SEQ ID NO 22
<211> LENGTH: 336
<212> TYPE: DNA
<213> ORGANISM: Artificial
<220> FEATURE:
<223> OTHER INFORMATION: synthetic

<400> SEQUENCE: 22
ctgcaaatcg acgaccaaga gtcctgcaaa ggcagatgca cagagggatt caatgtggat      60
aagaaatgcc aatgcgatgc cctctgctcc tactatcagt cctgctgtac cgattacaca     120
gccgaatgca aacccaagt gacaagcgga accgtcgcct ccagctccac cgctgtgatt     180
gtgtccgcct ccggcacagt ggcctcctcc agcacagccg tcatcgtcag cgccagcggc     240

```
accgtggcca gcagcagcac cgccgtgatc gtgagcgcca gcggcacagt cgcttcctcc      300
tccacagctg tcattgtctc cgctctccag attgac                                336
```

<210> SEQ ID NO 23
<211> LENGTH: 112
<212> TYPE: PRT
<213> ORGANISM: Artificial
<220> FEATURE:
<223> OTHER INFORMATION: synthetic
<400> SEQUENCE: 23

```
Leu Gln Ile Asp Asp Gln Glu Ser Cys Lys Gly Arg Cys Thr Glu Gly
1               5                   10                  15

Phe Asn Val Asp Lys Lys Cys Gln Cys Asp Glu Ala Cys Ser Tyr Tyr
            20                  25                  30

Gln Ser Cys Cys Thr Asp Tyr Thr Ala Glu Cys Lys Pro Gln Val Thr
        35                  40                  45

Ser Gly Thr Val Ala Ser Ser Thr Ala Val Ile Val Ser Ala Ser
    50                  55                  60

Gly Thr Val Ala Ser Ser Thr Ala Val Ile Val Ser Ala Ser Gly
65                  70                  75                  80

Thr Val Ala Ser Ser Thr Ala Val Ile Val Ser Ala Ser Gly Thr
                85                  90                  95

Val Ala Ser Ser Thr Ala Val Ile Val Ser Ala Leu Gln Ile Asp
            100                 105                 110
```

<210> SEQ ID NO 24
<211> LENGTH: 336
<212> TYPE: DNA
<213> ORGANISM: Artificial
<220> FEATURE:
<223> OTHER INFORMATION: synthetic
<400> SEQUENCE: 24

```
ctgcaaatcg acgaccaaga gtcctgcaaa ggcagatgca cagagggatt caatgtggat      60
aagaaatgcc aatgcgatga ggcttgctcc tactatcagt cctgctgtac cgattacaca     120
gccgaatgca aaccccaagt gacaagcgga accgtcgcct ccagctccac cgctgtgatt     180
gtgtccgcct ccggcacagt ggcctcctcc agcacagccg tcatcgtcag cgccagcggc     240
accgtggcca gcagcagcac cgccgtgatc gtgagcgcca gcggcacagt cgcttcctcc     300
tccacagctg tcattgtctc cgctctccag attgac                                336
```

<210> SEQ ID NO 25
<211> LENGTH: 306
<212> TYPE: PRT
<213> ORGANISM: Artificial
<220> FEATURE:
<223> OTHER INFORMATION: synthetic
<400> SEQUENCE: 25

```
Leu Gln Ile Asp Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Thr Ser Thr Thr Ser Thr Ser Ser Ser Thr Ser Arg Ala Thr
    50                  55                  60

Ser Ile Ile Gly Gly Glu Phe Thr Thr Ile Glu Asn Gln Pro Trp Phe
```

```
            65                  70                  75                  80
Ala Ala Ile Tyr Arg Arg His Arg Gly Gly Ser Val Thr Tyr Val Cys
                        85                  90                  95
Gly Gly Ser Leu Ile Ser Pro Cys Trp Val Ile Ser Ala Thr Ala Cys
                100                 105                 110
Phe Ile Asp Tyr Pro Lys Lys Glu Asp Tyr Ile Val Tyr Leu Gly Arg
            115                 120                 125
Ser Arg Leu Asn Ser Asn Thr Gln Gly Glu Met Lys Phe Glu Val Glu
        130                 135                 140
Asn Leu Ile Leu His Lys Asp Tyr Ser Ala Asp Thr Leu Ala His His
145                 150                 155                 160
Asn Ala Ile Ala Leu Leu Lys Ile Arg Ser Lys Glu Gly Arg Cys Ala
                165                 170                 175
Gln Pro Ser Arg Thr Ile Gln Thr Ile Cys Leu Pro Ser Met Tyr Asn
            180                 185                 190
Asp Pro Gln Phe Gly Thr Ser Cys Glu Ile Thr Gly Phe Gly Lys Glu
        195                 200                 205
Asn Ser Thr Asp Tyr Leu Tyr Pro Glu Gln Leu Lys Met Thr Val Val
    210                 215                 220
Lys Leu Ile Ser His Arg Glu Cys Gln Gln Pro His Tyr Tyr Gly Ser
225                 230                 235                 240
Glu Val Thr Thr Lys Met Leu Cys Ala Ala Asp Pro Gln Trp Lys Thr
                245                 250                 255
Asp Ser Cys Gln Gly Asp Ala Gly Gly Pro Leu Val Cys Ser Leu Gln
            260                 265                 270
Gly Arg Met Thr Leu Thr Gly Ile Val Ser Trp Gly Arg Gly Cys Ala
        275                 280                 285
Leu Lys Asp Lys Pro Gly Val Tyr Thr Arg Val Ser His Phe Leu Gln
    290                 295                 300
Ile Asp
305

<210> SEQ ID NO 26
<211> LENGTH: 918
<212> TYPE: DNA
<213> ORGANISM: Artificial
<220> FEATURE:
<223> OTHER INFORMATION: synthetic

<400> SEQUENCE: 26
ctgcaaattg acgaccaaga gtcctgcaaa ggcagatgca cagagggatt caatgtggat      60
aagaaatgcc aatgcgatga gctgtgctcc tactatcagt cctgctgtac cgattacaca     120
gccgaatgca accccaagt gacaacctcc accacaagca agctccag ctccaccaca       180 agcagggcca caagcatcat ggcggagag tttaccacaa tcgaaaacca accctggttc       240
gctgccattt acaggagaca tagaggaggc tccgtgacat acgtctgcgg aggctccctg       300
attagccctt gctgggtgat tagcgctacc gcttgcttta tcgactaccc taagaaagag       360
gattacattg tgtatctggg aagatccaga ctcaactcca acacacaggg agagatgaag      420
tttgaggtcg agaatctgat tctgcataag gattactccg ccgataccct cgcccatcac       480
aatgccattg ccctcctgaa aatcaggagc aagagggaa gatgtgccca acctccaga        540 acaatccaaa ccatttgcct ccctccatg tataacgatc cccaattcgg aacctcctgc       600
gaaatcacag gctttggcaa agagaatagc acagactatc tgtatcccga acagctcaag       660
atgaccgtcg tgaaactgat tagccataga gaatgccaac agcctcacta ttacggaagc       720
```

```
gaagtgacaa ccaaaatgct ctgcgctgcc gatccccaat ggaaaaccga tagctgtcag    780
ggcgacgccg gaggacccct cgtgtgtagc ctccagggaa gaatgaccct caccggaatc    840
gtcagctggg cagggcctg tgccctcaag gataagcctg cgtctacac aagagtcagc     900 catttcctcc agattgac                                                  918
```

<210> SEQ ID NO 27
<211> LENGTH: 301
<212> TYPE: PRT
<213> ORGANISM: Artificial
<220> FEATURE:
<223> OTHER INFORMATION: synthetic

<400> SEQUENCE: 27

```
Leu Gln Ile Asp Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Thr Ser Thr Thr Ser Thr Ser Ser Ser Thr Thr Ser Arg Ala Thr
    50                  55                  60

Ser Ile Val Gly Gly Trp Glu Cys Glu Lys His Ser Gln Pro Trp Gln
65                  70                  75                  80

Val Ala Val Tyr Ser His Gly Trp Ala His Cys Gly Gly Val Leu Val
                85                  90                  95

His Pro Gln Trp Val Leu Thr Ala Ala His Cys Leu Lys Lys Asn Ser
            100                 105                 110

Gln Val Trp Leu Gly Arg His Asn Leu Phe Glu Pro Glu Asp Thr Gly
        115                 120                 125

Gln Arg Val Pro Val Ser His Ser Phe Pro His Pro Leu Tyr Asn Met
    130                 135                 140

Ser Leu Leu Lys His Gln Ser Leu Arg Pro Asp Glu Asp Ser Ser His
145                 150                 155                 160

Asp Leu Met Leu Leu Arg Leu Ser Glu Pro Ala Lys Ile Thr Asp Val
                165                 170                 175

Val Lys Val Leu Gly Leu Pro Thr Gln Glu Pro Ala Leu Gly Thr Thr
            180                 185                 190

Cys Tyr Ala Ser Gly Trp Gly Ser Ile Glu Pro Glu Glu Phe Leu Arg
        195                 200                 205

Pro Arg Ser Leu Gln Cys Val Ser Leu His Leu Leu Ser Asn Asp Met
    210                 215                 220

Cys Ala Arg Ala Tyr Ser Glu Lys Val Thr Glu Phe Met Leu Cys Ala
225                 230                 235                 240

Gly Leu Trp Thr Gly Gly Lys Asp Thr Cys Gly Gly Asp Ser Gly Gly
                245                 250                 255

Pro Leu Val Cys Asn Gly Val Leu Gln Gly Ile Thr Ser Trp Gly Pro
            260                 265                 270

Glu Pro Cys Ala Leu Pro Glu Lys Pro Ala Val Tyr Thr Lys Val Val
        275                 280                 285

His Tyr Arg Lys Trp Ile Lys Asp Thr Leu Gln Ile Asp
    290                 295                 300
```

<210> SEQ ID NO 28
<211> LENGTH: 903
<212> TYPE: DNA

```
<213> ORGANISM: Artificial
<220> FEATURE:
<223> OTHER INFORMATION: synthetic

<400> SEQUENCE: 28
ctgcaaatcg acgaccaaga gtcctgcaaa ggcagatgca cagagggatt caatgtggat      60
aagaaatgcc aatgcgatga gctgtgctcc tactatcagt cctgctgtac cgattacaca     120
gccgaatgca aacccaagt gacaacctcc accacaagca caagctccag ctccaccaca     180
agcagggcca caagcatcgt cggcggatgg gaatgcgaaa agcatagcca accctggcaa     240
gtggccgtct actcccacgg atgggctcac tgtggcggag tgctcgtgca tccccaatgg     300
gtcctgacag ccgctcactg tctgaaaaag aatagccaag tgtggctggg cagacacaac     360
ctgttcgagc ccgaggacac aggccaaaga gtccccgtca gccatagctt tccccatccc     420
ctctacaata tgtccctgct caagcatcag tccctgaggc ccgatgagga tagctcccac     480
gatctgatgc tgctcagact cagcgaaccc gctaagatta ccgatgtggt caaggtcctg     540
ggactgccta cccaagagcc tgccctcggc acaacctgtt acgccagcgg atggggaagc     600
attgagcctg aggagtttct cagacctaga tccctgcaat gcgtcagcct ccacctcctg     660
tccaacgata tgtgtgccag ggcctatagc gaaaaggtca ccgagttcat gctgtgtgcc     720
ggactgtgga ccggaggcaa agacacatgc ggaggcgata cggaggccc tctggtctgc     780
aatggcgtcc tgcaaggcat tacctcctgg gacccgaac cctgtgccct cccgaaaag     840
cctgccgtct acacaaaggt cgtgcattac aggaagtgga tcaaagacac actccagatt     900
gac                                                                   903

<210> SEQ ID NO 29
<211> LENGTH: 112
<212> TYPE: PRT
<213> ORGANISM: Artificial
<220> FEATURE:
<223> OTHER INFORMATION: synthetic

<400> SEQUENCE: 29

Leu Gln Ile Asp Asp Gln Glu Phe Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Glu Leu Tyr Thr Tyr Tyr Cys Lys Pro Gln Val Thr
        35                  40                  45

Ser Gly Thr Val Ala Ser Ser Thr Ala Val Ile Val Ser Ala Ser
    50                  55                  60

Gly Thr Val Ala Ser Ser Thr Ala Val Ile Val Ser Ala Ser Gly
65                  70                  75                  80

Thr Val Ala Ser Ser Thr Ala Val Ile Val Ser Ala Ser Gly Thr
                85                  90                  95

Val Ala Ser Ser Thr Ala Val Ile Val Ser Ala Leu Gln Ile Asp
                100                 105                 110

<210> SEQ ID NO 30
<211> LENGTH: 336
<212> TYPE: DNA
<213> ORGANISM: Artificial
<220> FEATURE:
<223> OTHER INFORMATION: synthetic

<400> SEQUENCE: 30
ctgcaaatcg acgaccaaga gttttgcaaa ggcagatgca cagagggatt caatgtggat      60
```

-continued

```
aagaaatgcc aatgcgatga gctttgctcc tactatcagt cctgctgtga gctgtacaca    120
tactattgca aaccccaagt gacaagcgga accgtcgcct ccagctccac cgctgtgatt    180
gtgtccgcct ccggcacagt ggcctcctcc agcacagccg tcatcgtcag cgccagcggc    240
accgtggcca gcagcagcac cgccgtgatc gtgagcgcca gcggcacagt cgcttcctcc    300
tccacagctg tcattgtctc cgctctccag attgac                              336
```

<210> SEQ ID NO 31
<211> LENGTH: 402
<212> TYPE: PRT
<213> ORGANISM: Homo sapiens

<400> SEQUENCE: 31

| | | | | | | | | | | | | | | |
|---|---|---|---|---|---|---|---|---|---|---|---|---|---|---|
|Met|Gln|Met|Ser|Pro|Ala|Leu|Thr|Cys|Leu|Val|Leu|Gly|Leu|Ala|Leu|
|1| | | |5| | | | |10| | | | |15| |
|Val|Phe|Gly|Glu|Gly|Ser|Ala|Val|His|His|Pro|Ser|Tyr|Val|Ala| |
| | | |20| | | | |25| | | | |30| | |
|His|Leu|Ala|Ser|Asp|Phe|Gly|Val|Arg|Val|Phe|Gln|Gln|Val|Ala|Gln|
| | | |35| | | | |40| | | | |45| | |
|Ala|Ser|Lys|Asp|Arg|Asn|Leu|Val|Phe|Ser|Pro|Tyr|Gly|Val|Ala|Ser|
| |50| | | | |55| | | | |60| | | | |
|Val|Leu|Ala|Met|Leu|Gln|Leu|Thr|Thr|Gly|Gly|Glu|Thr|Gln|Gln|Gln|
|65| | | | |70| | | | |75| | | | |80|
|Ile|Gln|Ala|Ala|Met|Gly|Phe|Lys|Ile|Asp|Asp|Lys|Gly|Met|Ala|Pro|
| | | | |85| | | | |90| | | | |95| |
|Ala|Leu|Arg|His|Leu|Tyr|Lys|Glu|Leu|Met|Gly|Pro|Trp|Asn|Lys|Asp|
| | | |100| | | | |105| | | | |110| | |
|Glu|Ile|Ser|Thr|Thr|Asp|Ala|Ile|Phe|Val|Gln|Arg|Asp|Leu|Lys|Leu|
| | | |115| | | | |120| | | | |125| | |
|Val|Gln|Gly|Phe|Met|Pro|His|Phe|Phe|Arg|Leu|Phe|Arg|Ser|Thr|Val|
| | |130| | | | |135| | | | |140| | | |
|Lys|Gln|Val|Asp|Phe|Ser|Glu|Val|Glu|Arg|Ala|Arg|Phe|Ile|Ile|Asn|
|145| | | | |150| | | | |155| | | | |160|
|Asp|Trp|Val|Lys|Thr|His|Thr|Lys|Gly|Met|Ile|Ser|Asn|Leu|Leu|Gly|
| | | | |165| | | | |170| | | | |175| |
|Lys|Gly|Ala|Val|Asp|Gln|Leu|Thr|Arg|Leu|Val|Leu|Val|Asn|Ala|Leu|
| | | |180| | | | |185| | | | |190| | |
|Tyr|Phe|Asn|Gly|Gln|Trp|Lys|Thr|Pro|Phe|Pro|Asp|Ser|Ser|Thr|His|
| | | |195| | | | |200| | | | |205| | |
|Arg|Arg|Leu|Phe|His|Lys|Ser|Asp|Gly|Ser|Thr|Val|Ser|Val|Pro|Met|
| |210| | | | |215| | | | |220| | | | |
|Met|Ala|Gln|Thr|Asn|Lys|Phe|Asn|Tyr|Thr|Glu|Phe|Thr|Thr|Pro|Asp|
|225| | | | |230| | | | |235| | | | |240|
|Gly|His|Tyr|Tyr|Asp|Ile|Leu|Glu|Leu|Pro|Tyr|His|Gly|Asp|Thr|Leu|
| | | | |245| | | | |250| | | | |255| |
|Ser|Met|Phe|Ile|Ala|Ala|Pro|Tyr|Glu|Lys|Glu|Val|Pro|Leu|Ser|Ala|
| | | |260| | | | |265| | | | |270| | |
|Leu|Thr|Asn|Ile|Leu|Ser|Ala|Gln|Leu|Ile|Ser|His|Trp|Lys|Gly|Asn|
| | | |275| | | | |280| | | | |285| | |
|Met|Thr|Arg|Leu|Pro|Arg|Leu|Leu|Val|Leu|Pro|Lys|Phe|Ser|Leu|Glu|
| | |290| | | | |295| | | | |300| | | |
|Thr|Glu|Val|Asp|Leu|Arg|Lys|Pro|Leu|Glu|Asn|Leu|Gly|Met|Thr|Asp|
|305| | | | |310| | | | |315| | | | |320|
|Met|Phe|Arg|Gln|Phe|Gln|Ala|Asp|Phe|Thr|Ser|Leu|Ser|Asp|Gln|Glu|

```
                    325                 330                 335
Pro Leu His Val Ala Gln Ala Leu Gln Lys Val Lys Ile Glu Val Asn
                340                 345                 350
Glu Ser Gly Thr Val Ala Ser Ser Thr Ala Val Ile Val Ser Ala
            355                 360                 365
Arg Met Ala Pro Glu Glu Ile Ile Met Asp Arg Pro Phe Leu Phe Val
        370                 375                 380
Val Arg His Asn Pro Thr Gly Thr Val Leu Phe Met Gly Gln Val Met
385                 390                 395                 400
Glu Pro

<210> SEQ ID NO 32
<211> LENGTH: 478
<212> TYPE: PRT
<213> ORGANISM: Homo sapiens

<400> SEQUENCE: 32

Met Ala Pro Leu Arg Pro Leu Leu Ile Leu Ala Leu Leu Ala Trp Val
1               5                   10                  15
Ala Leu Ala Asp Gln Glu Ser Cys Lys Gly Arg Cys Thr Glu Gly Phe
            20                  25                  30
Asn Val Asp Lys Lys Cys Gln Cys Asp Glu Leu Cys Ser Tyr Tyr Gln
        35                  40                  45
Ser Cys Cys Thr Asp Tyr Thr Ala Glu Cys Lys Pro Gln Val Thr Arg
    50                  55                  60
Gly Asp Val Phe Thr Met Pro Glu Asp Glu Tyr Thr Val Tyr Asp Asp
65                  70                  75                  80
Gly Glu Glu Lys Asn Asn Ala Thr Val His Glu Gln Val Gly Gly Pro
                85                  90                  95
Ser Leu Thr Ser Asp Leu Gln Ala Gln Ser Lys Gly Asn Pro Glu Gln
            100                 105                 110
Thr Pro Val Leu Lys Pro Glu Glu Ala Pro Ala Pro Glu Val Gly
        115                 120                 125
Ala Ser Lys Pro Glu Gly Ile Asp Ser Arg Pro Glu Thr Leu His Pro
    130                 135                 140
Gly Arg Pro Gln Pro Pro Ala Glu Glu Glu Leu Cys Ser Gly Lys Pro
145                 150                 155                 160
Phe Asp Ala Phe Thr Asp Leu Lys Asn Gly Ser Leu Phe Ala Phe Arg
                165                 170                 175
Gly Gln Tyr Cys Tyr Glu Leu Asp Glu Lys Ala Val Arg Pro Gly Tyr
            180                 185                 190
Pro Lys Leu Ile Arg Asp Val Trp Gly Ile Glu Gly Pro Ile Asp Ala
        195                 200                 205
Ala Phe Thr Arg Ile Asn Cys Gln Gly Lys Thr Tyr Leu Phe Lys Gly
    210                 215                 220
Ser Gln Tyr Trp Arg Phe Glu Asp Gly Val Leu Asp Pro Asp Tyr Pro
225                 230                 235                 240
Arg Asn Ile Ser Asp Gly Phe Asp Gly Ile Pro Asp Asn Val Asp Ala
                245                 250                 255
Ala Leu Ala Leu Pro Ala His Ser Tyr Ser Gly Arg Glu Arg Val Tyr
            260                 265                 270
Phe Phe Lys Gly Lys Gln Tyr Trp Glu Tyr Gln Phe Gln His Gln Pro
        275                 280                 285
Ser Gln Glu Glu Cys Glu Gly Ser Ser Leu Ser Ala Val Phe Glu His
    290                 295                 300
```

```
Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
                340                 345                 350

Arg Ile Tyr Ile Ser Gly Met Ala Pro Arg Pro Ser Leu Ala Lys Lys
                355                 360                 365

Gln Arg Phe Arg His Arg Asn Arg Lys Gly Tyr Arg Ser Gln Arg Gly
370                 375                 380

His Ser Arg Gly Arg Asn Gln Asn Ser Arg Arg Pro Ser Arg Ala Met
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
                420                 425                 430

Ile Gln Ser Val Phe Phe Ser Gly Asp Lys Tyr Tyr Arg Val Asn
                435                 440                 445

Leu Arg Thr Arg Arg Val Asp Thr Val Asp Pro Pro Tyr Pro Arg Ser
450                 455                 460

Ile Ala Gln Tyr Trp Leu Gly Cys Pro Ala Pro Gly His Leu
465                 470                 475

<210> SEQ ID NO 33
<211> LENGTH: 261
<212> TYPE: PRT
<213> ORGANISM: Homo sapiens

<400> SEQUENCE: 33

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
                20                  25                  30

Lys His Ser Gln Pro Trp Gln Val Ala Val Tyr Ser His Gly Trp Ala
            35                  40                  45

His Cys Gly Gly Val Leu Val His Pro Gln Trp Val Leu Thr Ala Ala
        50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
                100                 105                 110

Pro Asp Glu Asp Ser Ser His Asp Leu Met Leu Leu Arg Leu Ser Glu
            115                 120                 125

Pro Ala Lys Ile Thr Asp Val Val Lys Val Leu Gly Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205
```

```
Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 34
<211> LENGTH: 532
<212> TYPE: PRT
<213> ORGANISM: Homo sapiens

<400> SEQUENCE: 34

Arg Arg Gly Ala Arg Ser Tyr Gln Val Ile Cys Arg Asp Glu Lys Thr
1               5                   10                  15

Gln Met Ile Tyr Gln Gln His Gln Ser Trp Leu Arg Pro Val Leu Arg
            20                  25                  30

Ser Asn Arg Val Glu Tyr Cys Trp Cys Asn Ser Gly Arg Ala Gln Cys
        35                  40                  45

His Ser Val Pro Val Lys Ser Cys Ser Glu Pro Arg Cys Phe Asn Gly
    50                  55                  60

Gly Thr Cys Gln Gln Ala Leu Tyr Phe Ser Asp Phe Val Cys Gln Cys
65                  70                  75                  80

Pro Glu Gly Phe Ala Gly Lys Cys Cys Glu Ile Asp Thr Arg Ala Thr
                85                  90                  95

Cys Tyr Glu Asp Gln Gly Ile Ser Tyr Arg Gly Thr Trp Ser Thr Ala
            100                 105                 110

Glu Ser Gly Ala Glu Cys Thr Asn Trp Asn Ser Ser Ala Leu Ala Gln
        115                 120                 125

Lys Pro Tyr Ser Gly Arg Arg Pro Asp Ala Ile Arg Leu Gly Leu Gly
    130                 135                 140

Asn His Asn Tyr Cys Arg Asn Pro Asp Arg Asp Ser Lys Pro Trp Cys
145                 150                 155                 160

Tyr Val Phe Lys Ala Gly Lys Tyr Ser Ser Glu Phe Cys Ser Thr Pro
                165                 170                 175

Ala Cys Ser Glu Gly Asn Ser Asp Cys Tyr Phe Gly Asn Gly Ser Ala
            180                 185                 190

Tyr Arg Gly Thr His Ser Leu Thr Glu Ser Gly Ala Ser Cys Leu Pro
        195                 200                 205

Trp Asn Ser Met Ile Leu Ile Gly Lys Val Tyr Thr Ala Gln Asn Pro
    210                 215                 220

Ser Ala Gln Ala Leu Gly Leu Gly Lys His Asn Tyr Cys Arg Asn Pro
225                 230                 235                 240

Asp Gly Asp Ala Lys Pro Trp Cys His Val Leu Lys Asn Arg Arg Leu
                245                 250                 255

Thr Trp Glu Tyr Cys Asp Val Pro Ser Cys Ser Thr Cys Gly Leu Arg
            260                 265                 270

Gln Tyr Ser Gln Pro Gln Phe Arg Ile Lys Gly Gly Leu Phe Ala Asp
        275                 280                 285

Ile Ala Ser His Pro Trp Gln Ala Ala Ile Phe Ala Lys His Arg Arg
    290                 295                 300

Ser Pro Gly Glu Arg Phe Leu Cys Gly Gly Ile Leu Ile Ser Ser Cys
305                 310                 315                 320
```

```
Trp Ile Leu Ser Ala His Cys Phe Gln Glu Arg Phe Pro Pro His
                325                 330                 335

His Leu Thr Val Ile Leu Gly Arg Thr Tyr Arg Val Pro Gly Glu
            340                 345                 350

Glu Glu Gln Lys Phe Glu Val Lys Tyr Ile Val His Lys Glu Phe
        355                 360                 365

Asp Asp Asp Thr Tyr Asp Asn Asp Ile Ala Leu Leu Gln Leu Lys Ser
    370                 375                 380

Asp Ser Ser Arg Cys Ala Gln Glu Ser Val Val Arg Thr Val Cys
385                 390                 395                 400

Leu Pro Pro Ala Asp Leu Gln Leu Pro Asp Trp Thr Glu Cys Glu Leu
                405                 410                 415

Ser Gly Tyr Gly Lys His Glu Ala Leu Ser Pro Phe Tyr Ser Glu Arg
                420                 425                 430

Leu Lys Glu Ala His Val Arg Leu Tyr Pro Ser Ser Arg Cys Thr Ser
            435                 440                 445

Gln His Leu Leu Asn Arg Thr Val Thr Asp Asn Met Leu Cys Ala Gly
        450                 455                 460

Asp Thr Arg Ser Gly Gly Pro Gln Ala Asn Leu His Asp Ala Cys Gln
465                 470                 475                 480

Gly Asp Ser Gly Gly Pro Leu Val Cys Leu Asn Asp Gly Arg Met Thr
                485                 490                 495

Leu Val Gly Ile Ile Ser Trp Gly Leu Gly Cys Gly Gln Lys Asp Val
                500                 505                 510

Pro Gly Val Tyr Thr Lys Val Thr Asn Tyr Leu Asp Trp Ile Arg Asp
            515                 520                 525

Asn Met Arg Pro
    530

<210> SEQ ID NO 35
<211> LENGTH: 904
<212> TYPE: PRT
<213> ORGANISM: Homo sapiens

<400> SEQUENCE: 35

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160
```

```
Ser Thr Lys Leu Gly Thr Gln Val Gln Leu Glu Asn Leu Gln Glu Leu
            165                 170                 175
Leu Leu Ser Asn Asn Lys Ile Gln Ala Leu Lys Ser Glu Glu Leu Asp
            180                 185                 190
Ile Phe Ala Asn Ser Ser Leu Lys Lys Leu Glu Leu Ser Ser Asn Gln
            195                 200                 205
Ile Lys Glu Phe Ser Pro Gly Cys Phe His Ala Ile Gly Arg Leu Phe
            210                 215                 220
Gly Leu Phe Leu Asn Asn Val Gln Leu Gly Pro Ser Leu Thr Glu Lys
225                 230                 235                 240
Leu Cys Leu Glu Leu Ala Asn Thr Ser Ile Arg Asn Leu Ser Leu Ser
                245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser Tyr Asn Asn Leu Asn Val
        275                 280                 285
Val Gly Asn Asp Ser Phe Ala Trp Leu Pro Gln Leu Glu Tyr Phe Phe
290                 295                 300
Leu Glu Tyr Asn Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Lys Cys Leu Glu His Leu Asn Met Glu Asp Asn Asp Ile Pro
        355                 360                 365
Gly Ile Lys Ser Asn Met Phe Thr Gly Leu Ile Asn Leu Lys Tyr Leu
        370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
            420                 425                 430
Leu Glu Val Leu Asp Leu Gly Leu Asn Glu Ile Gly Gln Glu Leu Thr
            435                 440                 445
Gly Gln Glu Trp Arg Gly Leu Glu Asn Ile Phe Glu Ile Tyr Leu Ser
450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
            515                 520                 525
Leu Glu Lys Leu Glu Ile Leu Asp Leu Gln His Asn Asn Leu Ala Arg
            530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
```

```
                580             585             590
Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
        610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
                675                 680                 685

Arg Leu Phe Asp Thr Ser Ser Cys Lys Asp Ser Ala Pro Phe Glu Leu
                690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
                740                 745                 750

Gln Phe Glu Tyr Ala Ala Tyr Ile Ile His Ala Tyr Lys Asp Lys Asp
                755                 760                 765

Trp Val Trp Glu His Phe Ser Ser Met Glu Lys Glu Asp Gln Ser Leu
                770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
                835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900

<210> SEQ ID NO 36
<211> LENGTH: 431
<212> TYPE: PRT
<213> ORGANISM: Homo sapiens

<400> SEQUENCE: 36

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
                20                  25                  30

Cys Leu Asn Gly Gly Thr Cys Val Ser Asn Lys Tyr Phe Ser Asn Ile
            35                  40                  45

His Trp Cys Asn Cys Pro Lys Lys Phe Gly Gly Gln His Cys Glu Ile
```

50                  55                  60
Asp Lys Ser Lys Thr Cys Tyr Glu Gly Asn Gly His Phe Tyr Arg Gly
 65                  70                  75                  80

Lys Ala Ser Thr Asp Thr Met Gly Arg Pro Cys Leu Pro Trp Asn Ser
                 85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Ile Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
            420                 425                 430

<210> SEQ ID NO 37
<211> LENGTH: 15
<212> TYPE: PRT
<213> ORGANISM: Artificial
<220> FEATURE:
<223> OTHER INFORMATION: synthetic

<400> SEQUENCE: 37

```
Ser Gly Thr Val Ala Ser Ser Ser Thr Ala Val Ile Val Ser Ala
1               5                   10                  15

<210> SEQ ID NO 38
<211> LENGTH: 10
<212> TYPE: PRT
<213> ORGANISM: Artificial
<220> FEATURE:
<223> OTHER INFORMATION: synthetic

<400> SEQUENCE: 38

Lys Phe Ser Leu Glu Thr Glu Val Asp Leu
1               5                   10

<210> SEQ ID NO 39
<211> LENGTH: 11
<212> TYPE: PRT
<213> ORGANISM: Artificial
<220> FEATURE:
<223> OTHER INFORMATION: synthetic

<400> SEQUENCE: 39

Ala Leu Gln Lys Val Lys Ile Glu Val Asn Glu
1               5                   10

<210> SEQ ID NO 40
<211> LENGTH: 44
<212> TYPE: PRT
<213> ORGANISM: Artificial
<220> FEATURE:
<223> OTHER INFORMATION: synthetic

<400> SEQUENCE: 40

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr
            35                  40

<210> SEQ ID NO 41
<211> LENGTH: 44
<212> TYPE: PRT
<213> ORGANISM: Artificial
<220> FEATURE:
<223> OTHER INFORMATION: synthetic

<400> SEQUENCE: 41

Asp Gln Glu Ser Cys Lys Gly Arg Cys Thr Glu Gly Leu Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr
            35                  40

<210> SEQ ID NO 42
<211> LENGTH: 44
<212> TYPE: PRT
<213> ORGANISM: Artificial
<220> FEATURE:
<223> OTHER INFORMATION: synthetic

<400> SEQUENCE: 42

Asp Gln Glu Ser Cys Lys Gly Arg Cys Ala Glu Gly Phe Asn Val Asp
1               5                   10                  15
```

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr
            35                  40

<210> SEQ ID NO 43
<211> LENGTH: 44
<212> TYPE: PRT
<213> ORGANISM: Artificial
<220> FEATURE:
<223> OTHER INFORMATION: synthetic

<400> SEQUENCE: 43

Asp Gln Glu Ser Cys Lys Gly Arg Cys Thr Glu Gly Phe Asn Val Asp
1               5                   10                  15

Lys Lys Cys Gln Cys Asp Ala Leu Cys Ser Tyr Tyr Gln Ser Cys Cys
            20                  25                  30

Thr Asp Tyr Thr Ala Glu Cys Lys Pro Gln Val Thr
            35                  40

<210> SEQ ID NO 44
<211> LENGTH: 44
<212> TYPE: PRT
<213> ORGANISM: Artificial
<220> FEATURE:
<223> OTHER INFORMATION: synthetic

<400> SEQUENCE: 44

Asp Gln Glu Ser Cys Lys Gly Arg Cys Thr Glu Gly Phe Asn Val Asp
1               5                   10                  15

Lys Lys Cys Gln Cys Asp Glu Ala Cys Ser Tyr Tyr Gln Ser Cys Cys
            20                  25                  30

Thr Asp Tyr Thr Ala Glu Cys Lys Pro Gln Val Thr
            35                  40

<210> SEQ ID NO 45
<211> LENGTH: 44
<212> TYPE: PRT
<213> ORGANISM: Artificial
<220> FEATURE:
<223> OTHER INFORMATION: synthetic

<400> SEQUENCE: 45

Asp Gln Glu Phe Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Glu Leu Tyr Thr Tyr Tyr Cys Lys Pro Gln Val Thr
            35                  40

<210> SEQ ID NO 46
<211> LENGTH: 232
<212> TYPE: PRT
<213> ORGANISM: Artificial
<220> FEATURE:
<223> OTHER INFORMATION: synthetic

<400> SEQUENCE: 46

Ile Val Gly Gly Trp Glu Cys Glu Lys His Ser Gln Pro Trp Gln Val
1               5                   10                  15

Ala Val Tyr Ser His Gly Trp Ala His Cys Gly Gly Val Leu Val His
            20                  25                  30

Pro Gln Trp Val Leu Thr Ala Ala His Cys Leu Lys Lys Asn Ser Gln
         35                  40                  45

Val Trp Leu Gly Arg His Asn Leu Phe Glu Pro Glu Asp Thr Gly Gln
 50                  55                  60

Arg Val Pro Val Ser His Ser Phe Pro His Pro Leu Tyr Asn Met Ser
 65                  70                  75                  80

Leu Leu Lys His Gln Ser Leu Arg Pro Asp Glu Asp Ser Ser His Asp
                 85                  90                  95

Leu Met Leu Leu Arg Leu Ser Glu Pro Ala Lys Ile Thr Asp Val Val
             100                 105                 110

Lys Val Leu Gly Leu Pro Thr Gln Glu Pro Ala Leu Gly Thr Thr Cys
         115                 120                 125

Tyr Ala Ser Gly Trp Gly Ser Ile Glu Pro Glu Glu Phe Leu Arg Pro
 130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                 165                 170                 175

Leu Trp Thr Gly Gly Lys Asp Thr Cys Gly Gly Asp Ser Gly Gly Pro
             180                 185                 190

Leu Val Cys Asn Gly Val Leu Gln Gly Ile Thr Ser Trp Gly Pro Glu
         195                 200                 205

Pro Cys Ala Leu Pro Glu Lys Pro Ala Val Tyr Thr Lys Val Val His
 210                 215                 220

Tyr Arg Lys Trp Ile Lys Asp Thr
225                 230

<210> SEQ ID NO 47
<211> LENGTH: 20
<212> TYPE: PRT
<213> ORGANISM: Artificial
<220> FEATURE:
<223> OTHER INFORMATION: synthetic

<400> SEQUENCE: 47

Ile Val Gly Gly Trp Glu Cys Glu Lys His Ser Gln Pro Trp Gln Val
1               5                   10                  15

Ala Val Tyr Ser
            20

<210> SEQ ID NO 48
<211> LENGTH: 210
<212> TYPE: PRT
<213> ORGANISM: Artificial
<220> FEATURE:
<223> OTHER INFORMATION: synthetic

<400> SEQUENCE: 48

Trp Ala His Cys Gly Gly Val Leu Val His Pro Gln Trp Val Leu Thr
1               5                   10                  15

Ala Ala His Cys Leu Lys Lys Asn Ser Gln Val Trp Leu Gly Arg His
            20                  25                  30

Asn Leu Phe Glu Pro Glu Asp Thr Gly Gln Arg Val Pro Val Ser His
        35                  40                  45

Ser Phe Pro His Pro Leu Tyr Asn Met Ser Leu Leu Lys His Gln Ser
    50                  55                  60

Leu Arg Pro Asp Glu Asp Ser Ser His Asp Leu Met Leu Leu Arg Leu
65                  70                  75                  80

```
Ser Glu Pro Ala Lys Ile Thr Asp Val Val Lys Val Leu Gly Leu Pro
                85                  90                  95

Thr Gln Glu Pro Ala Leu Gly Thr Thr Cys Tyr Ala Ser Gly Trp Gly
            100                 105                 110

Ser Ile Glu Pro Glu Glu Phe Leu Arg Pro Arg Ser Leu Gln Cys Val
        115                 120                 125

Ser Leu His Leu Leu Ser Asn Asp Met Cys Ala Arg Ala Tyr Ser Glu
    130                 135                 140

Lys Val Thr Glu Phe Met Leu Cys Ala Gly Leu Trp Thr Gly Gly Lys
145                 150                 155                 160

Asp Thr Cys Gly Gly Asp Ser Gly Gly Pro Leu Val Cys Asn Gly Val
                165                 170                 175

Leu Gln Gly Ile Thr Ser Trp Gly Pro Glu Pro Cys Ala Leu Pro Glu
            180                 185                 190

Lys Pro Ala Val Tyr Thr Lys Val Val His Tyr Arg Lys Trp Ile Lys
        195                 200                 205

Asp Thr
    210

<210> SEQ ID NO 49
<211> LENGTH: 8
<212> TYPE: PRT
<213> ORGANISM: Artificial
<220> FEATURE:
<223> OTHER INFORMATION: synthetic

<400> SEQUENCE: 49

Lys His Arg Arg Ser Pro Gly Glu
1               5

<210> SEQ ID NO 50
<211> LENGTH: 93
<212> TYPE: PRT
<213> ORGANISM: Artificial
<220> FEATURE:
<223> OTHER INFORMATION: synthetic

<400> SEQUENCE: 50

Thr Val Ser His Glu Val Ala Asp Cys Ser His Leu Lys Leu Thr Gln
1               5                   10                  15

Val Pro Asp Asp Leu Pro Thr Asn Ile Thr Ala Leu Tyr Leu Asn His
            20                  25                  30

Asn Gln Leu Arg Arg Leu Pro Ala Ala Asn Phe Thr Arg Tyr Ser Gln
        35                  40                  45

Leu Thr Lys Leu Lys Val Glu Phe Asn Thr Ile Ser Lys Leu Glu Pro
    50                  55                  60

Glu Leu Cys Gln Lys Leu Pro Met Leu Lys Val Leu Asn Leu Gln His
65                  70                  75                  80

Asn Glu Leu Ser Gln Leu Ser Asp Lys Thr Phe Ala Phe
                85                  90

<210> SEQ ID NO 51
<211> LENGTH: 237
<212> TYPE: PRT
<213> ORGANISM: Artificial
<220> FEATURE:
<223> OTHER INFORMATION: synthetic

<400> SEQUENCE: 51

Ile Ile Gly Gly Glu Phe Thr Thr Ile Glu Asn Gln Pro Trp Phe Ala
1               5                   10                  15
```

```
Ala Ile Tyr Arg Arg His Arg Gly Gly Ser Val Thr Tyr Val Cys Gly
             20                  25                  30

Gly Ser Leu Ile Ser Pro Cys Trp Val Ile Ser Ala Thr Ala Cys Phe
             35                  40                  45

Ile Asp Tyr Pro Lys Lys Glu Asp Tyr Ile Val Tyr Leu Gly Arg Ser
 50                  55                  60

Arg Leu Asn Ser Asn Thr Gln Gly Glu Met Lys Phe Glu Val Glu Asn
 65                  70                  75                  80

Leu Ile Leu His Lys Asp Tyr Ser Ala Asp Thr Leu Ala His His Asn
                 85                  90                  95

Ala Ile Ala Leu Leu Lys Ile Arg Ser Lys Glu Gly Arg Cys Ala Gln
                100                 105                 110

Pro Ser Arg Thr Ile Gln Thr Ile Cys Leu Pro Ser Met Tyr Asn Asp
                115                 120                 125

Pro Gln Phe Gly Thr Ser Cys Glu Ile Thr Gly Phe Gly Lys Glu Asn
130                 135                 140

Ser Thr Asp Tyr Leu Tyr Pro Glu Gln Leu Lys Met Thr Val Val Lys
145                 150                 155                 160

Leu Ile Ser His Arg Glu Cys Gln Gln Pro His Tyr Tyr Gly Ser Glu
                165                 170                 175

Val Thr Thr Lys Met Leu Cys Ala Ala Asp Pro Gln Trp Lys Thr Asp
                180                 185                 190

Ser Cys Gln Gly Asp Ala Gly Gly Pro Leu Val Cys Ser Leu Gln Gly
                195                 200                 205

Arg Met Thr Leu Thr Gly Ile Val Ser Trp Gly Arg Gly Cys Ala Leu
210                 215                 220

Lys Asp Lys Pro Gly Val Tyr Thr Arg Val Ser His Phe
225                 230                 235

<210> SEQ ID NO 52
<211> LENGTH: 476
<212> TYPE: PRT
<213> ORGANISM: Humicola insolens

<400> SEQUENCE: 52

Met Ala Lys Phe Phe Leu Thr Ala Ala Phe Ala Ala Ala Ala Leu Ala
 1               5                  10                  15

Ala Pro Val Val Glu Glu Arg Gln Asn Cys Ala Pro Thr Trp Gly Gln
             20                  25                  30

Cys Gly Gly Ile Gly Phe Asn Gly Pro Thr Cys Cys Gln Ser Gly Ser
             35                  40                  45

Thr Cys Val Lys Gln Asn Asp Trp Tyr Ser Gln Cys Leu Pro Gly Ser
 50                  55                  60

Gln Val Thr Thr Thr Ser Thr Thr Ser Thr Ser Ser Ser Ser Thr Thr
 65                  70                  75                  80

Ser Arg Ala Thr Ser Thr Thr Arg Thr Gly Gly Val Thr Ser Ile Thr
                 85                  90                  95

Thr Ala Pro Thr Arg Thr Val Thr Ile Pro Gly Gly Ala Thr Thr Thr
                100                 105                 110

Ala Ser Tyr Asn Gly Asn Pro Phe Glu Gly Val Gln Leu Trp Ala Asn
                115                 120                 125

Asn Tyr Tyr Arg Ser Glu Val His Thr Leu Ala Ile Pro Gln Ile Thr
130                 135                 140

Asp Pro Ala Leu Arg Ala Ala Ala Ser Ala Val Ala Glu Val Pro Ser
145                 150                 155                 160
```

Phe Gln Trp Leu Asp Arg Asn Val Thr Val Asp Thr Leu Leu Val Glu
                165                 170                 175

Thr Leu Ser Glu Ile Arg Ala Ala Asn Gln Ala Gly Ala Asn Pro Pro
            180                 185                 190

Tyr Ala Ala Gln Ile Val Val Tyr Asp Leu Pro Asp Arg Asp Cys Ala
        195                 200                 205

Ala Ala Ala Ser Asn Gly Glu Trp Ala Ile Ala Asn Asn Gly Ala Asn
    210                 215                 220

Asn Tyr Lys Gly Tyr Ile Asn Arg Ile Arg Glu Ile Leu Ile Ser Phe
225                 230                 235                 240

Ser Asp Val Arg Thr Ile Leu Val Ile Glu Pro Asp Ser Leu Ala Asn
                245                 250                 255

Met Val Thr Asn Met Asn Val Ala Lys Cys Ser Gly Ala Ala Ser Thr
            260                 265                 270

Tyr Arg Glu Leu Thr Ile Tyr Ala Leu Lys Gln Leu Asp Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Lys Ile Tyr Glu Asp
305                 310                 315                 320

Ala Gly Lys Pro Arg Ala Val Arg Gly Leu Ala Thr Asn Val Ala Asn
                325                 330                 335

Tyr Asn Ala Trp Ser Ile Ser Ser Pro Pro Tyr Thr Ser Pro Asn
            340                 345                 350

Pro Asn Tyr Asp Glu Lys His Tyr Ile Glu Ala Phe Arg Pro Leu Leu
        355                 360                 365

Glu Ala Arg Gly Phe Pro Ala Gln Phe Ile Val Asp Gln Gly Arg Ser
    370                 375                 380

Gly Lys Gln Pro Thr Gly Gln Lys Glu Trp Gly His Trp Cys Asn Ala
385                 390                 395                 400

Ile Gly Thr Gly Phe Gly Met Arg Pro Thr Ala Asn Thr Gly His Gln
                405                 410                 415

Tyr Val Asp Ala Phe Val Trp Val Lys Pro Gly Gly Glu Cys Asp Gly
        420                 425                 430

Thr Ser Asp Thr Thr Ala Ala Arg Tyr Asp Tyr His Cys Gly Leu Glu
    435                 440                 445

Asp Ala Leu Lys Pro Ala Pro Glu Ala Gly Gln Trp Phe Gln Ala Tyr
450                 455                 460

Phe Glu Gln Leu Leu Arg Asn Ala Asn Pro Pro Phe
465                 470                 475

<210> SEQ ID NO 53
<211> LENGTH: 17
<212> TYPE: PRT
<213> ORGANISM: Artificial
<220> FEATURE:
<223> OTHER INFORMATION: synthetic

<400> SEQUENCE: 53

Thr Ser Thr Thr Ser Thr Ser Ser Ser Thr Thr Ser Arg Ala Thr
1               5                   10                  15

Ser

<210> SEQ ID NO 54
<211> LENGTH: 4
<212> TYPE: PRT

-continued

```
<213> ORGANISM: Artificial
<220> FEATURE:
<223> OTHER INFORMATION: synthetic

<400> SEQUENCE: 54

Leu Gln Ile Asp
1

<210> SEQ ID NO 55
<211> LENGTH: 4
<212> TYPE: PRT
<213> ORGANISM: Artificial
<220> FEATURE:
<223> OTHER INFORMATION: synthetic

<400> SEQUENCE: 55

Asn Pro Ala Gly
1

<210> SEQ ID NO 56
<211> LENGTH: 12
<212> TYPE: PRT
<213> ORGANISM: Artificial
<220> FEATURE:
<223> OTHER INFORMATION: synthetic

<400> SEQUENCE: 56

Ser Asp Val Thr Gly Asn Ala Thr Tyr Thr Ile Thr
1               5                   10

<210> SEQ ID NO 57
<211> LENGTH: 127
<212> TYPE: PRT
<213> ORGANISM: Artificial
<220> FEATURE:
<223> OTHER INFORMATION: synthetic

<400> SEQUENCE: 57

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Val
            20                  25                  30

Trp Gly Arg Ser Tyr Pro Tyr Asp Val Pro Asp Tyr Ala Tyr Pro Tyr
        35                  40                  45

Asp Val Pro Asp Tyr Ala Ala Ser Gly Ala Ala Ile Asp Val Phe
    50                  55                  60

Asp Val Leu Ile Ser Gly Asp Pro Asn Phe Thr Val Ala Ala Gln Ala
65                  70                  75                  80

Ala Leu Glu Asp Ala Arg Ala Phe Leu Pro Asp Leu Glu Lys Leu His
                85                  90                  95

Leu Phe Pro Ser Asp Ala Gly Val Pro Leu Ser Ser Ala Thr Leu Leu
            100                 105                 110

Ala Pro Leu Leu Ser Gly Leu Phe Val Leu Trp Leu Cys Ile Gln
        115                 120                 125

<210> SEQ ID NO 58
<211> LENGTH: 135
<212> TYPE: PRT
<213> ORGANISM: Artificial
<220> FEATURE:
<223> OTHER INFORMATION: synthetic

<400> SEQUENCE: 58

Met Thr Val Ala Arg Pro Ser Val Pro Ala Ala Leu Pro Leu Leu Gly
```

```
                 1               5              10              15
Glu Leu Pro Arg Leu Leu Leu Val Leu Leu Cys Leu Pro Ala Val
                20              25              30

Trp Gly Arg Ser Tyr Pro Tyr Asp Val Pro Asp Tyr Ala Tyr Pro Tyr
                35              40              45

Asp Val Pro Asp Tyr Ala Ala Ser Gly Ala Ala Ile Asp Gly Ser
         50              55              60

Pro Lys Pro Pro Glu Ala Val Phe Asp Val Leu Ile Ser Gly Asp Pro
65              70              75              80

Asn Phe Thr Val Ala Ala Gln Ala Ala Leu Glu Asp Ala Arg Ala Phe
                85              90              95

Leu Pro Asp Leu Glu Lys Leu His Leu Phe Pro Ser Asp Ala Gly Val
            100             105             110

Pro Leu Ser Ser Ala Thr Leu Leu Ala Pro Leu Leu Ser Gly Leu Phe
            115             120             125

Val Leu Trp Leu Cys Ile Gln
            130             135
```

<210> SEQ ID NO 59
<211> LENGTH: 176
<212> TYPE: PRT
<213> ORGANISM: Artificial
<220> FEATURE:
<223> OTHER INFORMATION: synthetic

<400> SEQUENCE: 59

```
Met Thr Val Ala Arg Pro Ser Val Pro Ala Ala Leu Pro Leu Leu Gly
1               5              10              15

Glu Leu Pro Arg Leu Leu Leu Leu Val Leu Leu Cys Leu Pro Ala Val
                20              25              30

Trp Gly Arg Ser Tyr Pro Tyr Asp Val Pro Asp Tyr Ala Tyr Pro Tyr
                35              40              45

Asp Val Pro Asp Tyr Ala Ala Ser Gly Ala Ala Ile Asp Asp Leu
         50              55              60

Gln Leu Cys Val Gly Val Cys Pro Pro Ser Gln Arg Leu Ser Arg Ser
65              70              75              80

Glu Arg Asn Arg Arg Gly Ala Ile Thr Ile Asp Thr Ala Arg Arg Leu
                85              90              95

Cys Lys Glu Gly Leu Pro Val Glu Asp Ala Tyr Phe His Ser Cys Val
            100             105             110

Phe Asp Val Leu Ile Ser Gly Asp Pro Asn Phe Thr Val Ala Ala Gln
            115             120             125

Ala Ala Leu Glu Asp Ala Arg Ala Phe Leu Pro Asp Leu Glu Lys Leu
        130             135             140

His Leu Phe Pro Ser Asp Ala Gly Val Pro Leu Ser Ser Ala Thr Leu
145             150             155             160

Leu Ala Pro Leu Leu Ser Gly Leu Phe Val Leu Trp Leu Cys Ile Gln
                165             170             175
```

<210> SEQ ID NO 60
<211> LENGTH: 189
<212> TYPE: PRT
<213> ORGANISM: Artificial
<220> FEATURE:
<223> OTHER INFORMATION: synthetic

<400> SEQUENCE: 60

Met Thr Val Ala Arg Pro Ser Val Pro Ala Ala Leu Pro Leu Leu Gly

```
             1               5                  10                 15
Glu Leu Pro Arg Leu Leu Leu Val Leu Leu Cys Leu Pro Ala Val
            20                 25                 30

Trp Gly Arg Ser Tyr Pro Tyr Asp Val Pro Asp Tyr Ala Tyr Pro Tyr
            35                 40                 45

Asp Val Pro Asp Tyr Ala Ala Ser Gly Ala Ala Ile Asp Gly Ser
 50                55                 60

Pro Lys Pro Glu Ala Glu Cys Arg Asp Glu Lys Phe Ala Cys Thr
 65                70                 75                 80

Arg Leu Tyr Ser Val His Arg Pro Cys Lys Gln Cys Leu His Gln Ile
                85                 90                 95

Cys Phe Thr Ser Ser Arg Arg Met Tyr Val Ile Asn Asn Glu Ile Cys
               100                105                110

Ser Arg Leu Val Cys Lys Glu His Glu Ala Met Lys Val Phe Asp Val
               115                120                125

Leu Ile Ser Gly Asp Pro Asn Phe Thr Val Ala Ala Gln Ala Ala Leu
           130                135                140

Glu Asp Ala Arg Ala Phe Leu Pro Asp Leu Glu Lys Leu His Leu Phe
145                150                155                160

Pro Ser Asp Ala Gly Val Pro Leu Ser Ser Ala Thr Leu Leu Ala Pro
                 165                170                175

Leu Leu Ser Gly Leu Phe Val Leu Trp Leu Cys Ile Gln
           180                185
```

<210> SEQ ID NO 61
<211> LENGTH: 97
<212> TYPE: PRT
<213> ORGANISM: Artificial
<220> FEATURE:
<223> OTHER INFORMATION: synthetic

<400> SEQUENCE: 61

```
Met Asn Leu Ala Ile Ser Ile Ala Leu Leu Leu Thr Val Leu Gln Val
 1               5                  10                 15

Ser Arg Gly Arg Ser Tyr Pro Tyr Asp Val Pro Asp Tyr Ala Tyr Pro
                20                 25                 30

Tyr Asp Val Pro Asp Tyr Ala Ala Ser Gly Ala Ala Ala Ile Asp Ser
             35                 40                 45

Pro Pro Ile Ser Ser Gln Asn Val Thr Val Leu Arg Asp Lys Leu Val
 50                 55                 60

Lys Cys Glu Gly Ile Ser Leu Leu Ala Gln Asn Thr Ser Trp Leu Leu
65                  70                 75                 80

Leu Leu Leu Leu Ser Leu Ser Leu Leu Gln Ala Thr Asp Phe Met Ser
                85                 90                 95

Leu
```

<210> SEQ ID NO 62
<211> LENGTH: 107
<212> TYPE: PRT
<213> ORGANISM: Artificial
<220> FEATURE:
<223> OTHER INFORMATION: synthetic

<400> SEQUENCE: 62

```
Met Asn Leu Ala Ile Ser Ile Ala Leu Leu Leu Thr Val Leu Gln Val
 1               5                  10                 15

Ser Arg Gly Arg Ser Tyr Pro Tyr Asp Val Pro Asp Tyr Ala Tyr Pro
                20                 25                 30
```

```
Tyr Asp Val Pro Asp Tyr Ala Ala Ser Gly Ala Ala Ile Asp Gln
            35                  40                  45

Lys Gly Ser Val Gly Phe Ala Asp Pro Ser Pro Ile Ser Ser Gln
 50                  55                  60

Asn Val Thr Val Leu Arg Asp Lys Leu Val Lys Cys Glu Gly Ile Ser
 65                  70                  75                  80

Leu Leu Ala Gln Asn Thr Ser Trp Leu Leu Leu Leu Leu Ser Leu
                85                  90                  95

Ser Leu Leu Gln Ala Thr Asp Phe Met Ser Leu
            100                 105

<210> SEQ ID NO 63
<211> LENGTH: 207
<212> TYPE: PRT
<213> ORGANISM: Artificial
<220> FEATURE:
<223> OTHER INFORMATION: synthetic

<400> SEQUENCE: 63

Met Asn Leu Ala Ile Ser Ile Ala Leu Leu Leu Thr Val Leu Gln Val
 1               5                  10                  15

Ser Arg Gly Arg Ser Tyr Pro Tyr Asp Val Pro Asp Tyr Ala Tyr Pro
                20                  25                  30

Tyr Asp Val Pro Asp Tyr Ala Ala Ser Gly Ala Ala Ile Asp Gly
            35                  40                  45

Ser Pro Lys Pro Pro Glu Ala Pro Pro Gln Pro Gly Gly His Thr
 50                  55                  60

Val Gly Ala Gly Val Gly Ser Pro Ser Ser Gln Leu Tyr Glu His Thr
 65                  70                  75                  80

Val Glu Gly Gly Glu Lys Gln Val Val Phe Thr His Arg Ile Asn Leu
                85                  90                  95

Pro Pro Ser Thr Gly Cys Gly Cys Pro Pro Gly Thr Glu Pro Pro Val
            100                 105                 110

Leu Ala Ser Glu Val Gln Ala Leu Arg Val Arg Leu Glu Ile Leu Glu
            115                 120                 125

Glu Leu Val Lys Gly Leu Lys Glu Gln Cys Thr Gly Gly Cys Cys Pro
            130                 135                 140

Ala Ser Ala Gln Ala Gly Thr Gly Gln Thr Asp Val Arg Ser Pro Pro
145                 150                 155                 160

Ile Ser Ser Gln Asn Val Thr Val Leu Arg Asp Lys Leu Val Lys Cys
                165                 170                 175

Glu Gly Ile Ser Leu Leu Ala Gln Asn Thr Ser Trp Leu Leu Leu Leu
            180                 185                 190

Leu Leu Ser Leu Ser Leu Leu Gln Ala Thr Asp Phe Met Ser Leu
            195                 200                 205

<210> SEQ ID NO 64
<211> LENGTH: 167
<212> TYPE: PRT
<213> ORGANISM: Artificial
<220> FEATURE:
<223> OTHER INFORMATION: synthetic

<400> SEQUENCE: 64

Met Asn Leu Ala Ile Ser Ile Ala Leu Leu Leu Thr Val Leu Gln Val
 1               5                  10                  15

Ser Arg Gly Arg Ser Tyr Pro Tyr Asp Val Pro Asp Tyr Ala Tyr Pro
                20                  25                  30
```

```
Tyr Asp Val Pro Asp Tyr Ala Ala Ser Gly Ala Ala Ala Ile Asp Asn
            35                  40                  45

Gln Ser Asp Ile Val Ala His Leu Leu Ser Ser Ser Ser Ser Val Ile
 50                  55                  60

Asp Ala Leu Gln Tyr Lys Leu Glu Gly Thr Thr Arg Leu Thr Arg Lys
 65                  70                  75                  80

Arg Gly Leu Lys Leu Ala Thr Ala Leu Ser Leu Ser Asn Lys Phe Val
                 85                  90                  95

Glu Gly Ser His Asn Ser Thr Val Ser Leu Thr Thr Lys Asn Met Glu
                100                 105                 110

Val Ser Val Ala Thr Ser Pro Pro Ile Ser Ser Gln Asn Val Thr Val
            115                 120                 125

Leu Arg Asp Lys Leu Val Lys Cys Glu Gly Ile Ser Leu Leu Ala Gln
130                 135                 140

Asn Thr Ser Trp Leu Leu Leu Leu Leu Ser Leu Ser Leu Leu Gln
145                 150                 155                 160

Ala Thr Asp Phe Met Ser Leu
                165
```

<210> SEQ ID NO 65
<211> LENGTH: 106
<212> TYPE: PRT
<213> ORGANISM: Artificial
<220> FEATURE:
<223> OTHER INFORMATION: synthetic

<400> SEQUENCE: 65

```
Met Glu Leu Arg Ala Arg Gly Trp Trp Leu Leu Tyr Ala Ala Ala Val
 1               5                  10                  15

Leu Val Ala Cys Ala Arg Gly Arg Ser Tyr Pro Tyr Asp Val Pro Asp
                20                  25                  30

Tyr Ala Tyr Pro Tyr Asp Val Pro Asp Tyr Ala Ala Ser Gly Ala Ala
            35                  40                  45

Ala Ile Asp Arg Lys Ser Ala Ser Ser Arg Thr Pro Leu Thr His Ala
 50                  55                  60

Leu Pro Gly Leu Ser Glu Arg Glu Gly Gln Gln Thr Ser Ala Ala Ala
 65                  70                  75                  80

Pro Thr Pro Pro Gln Ala Ser Pro Leu Leu Leu Gly Leu Ala Leu
                 85                  90                  95

Ala Leu Pro Ala Ala Pro Arg Gly Arg
                100                 105
```

<210> SEQ ID NO 66
<211> LENGTH: 116
<212> TYPE: PRT
<213> ORGANISM: Artificial
<220> FEATURE:
<223> OTHER INFORMATION: synthetic

<400> SEQUENCE: 66

```
Met Glu Leu Arg Ala Arg Gly Trp Trp Leu Leu Tyr Ala Ala Ala Val
 1               5                  10                  15

Leu Val Ala Cys Ala Arg Gly Arg Ser Tyr Pro Tyr Asp Val Pro Asp
                20                  25                  30

Tyr Ala Tyr Pro Tyr Asp Val Pro Asp Tyr Ala Ala Ser Gly Ala Ala
            35                  40                  45

Ala Ile Asp Gln Lys Gly Ser Val Gly Phe Ala Asp Pro Arg Lys Ser
 50                  55                  60
```

```
Ala Ser Ser Arg Thr Pro Leu Thr His Ala Leu Pro Gly Leu Ser Glu
 65                  70                  75                  80

Arg Glu Gly Gln Gln Thr Ser Ala Ala Ala Pro Thr Pro Pro Gln Ala
                 85                  90                  95

Ser Pro Leu Leu Leu Leu Gly Leu Ala Leu Ala Leu Pro Ala Ala Ala
            100                 105                 110

Pro Arg Gly Arg
        115

<210> SEQ ID NO 67
<211> LENGTH: 218
<212> TYPE: PRT
<213> ORGANISM: Artificial
<220> FEATURE:
<223> OTHER INFORMATION: synthetic

<400> SEQUENCE: 67

Met Glu Leu Arg Ala Arg Gly Trp Trp Leu Leu Tyr Ala Ala Ala Val
  1               5                  10                  15

Leu Val Ala Cys Ala Arg Gly Arg Ser Tyr Pro Tyr Asp Val Pro Asp
                 20                  25                  30

Tyr Ala Tyr Pro Tyr Asp Val Pro Asp Tyr Ala Ala Ser Gly Ala Ala
             35                  40                  45

Ala Ile Asp Gln Lys Gly Ser Val Gly Phe Ala Asp Pro Pro Pro Pro
 50                  55                  60

Gln Pro Gly Gly His Thr Val Gly Ala Gly Val Gly Ser Pro Ser Ser
 65                  70                  75                  80

Gln Leu Tyr Glu His Thr Val Glu Gly Gly Glu Lys Gln Val Val Phe
                 85                  90                  95

Thr His Arg Ile Asn Leu Pro Pro Ser Thr Gly Cys Gly Cys Pro Pro
            100                 105                 110

Gly Thr Glu Pro Pro Val Leu Ala Ser Glu Val Gln Ala Leu Arg Val
            115                 120                 125

Arg Leu Glu Ile Leu Glu Glu Leu Val Lys Gly Leu Lys Glu Gln Cys
130                 135                 140

Thr Gly Gly Cys Cys Pro Ala Ser Ala Gln Ala Gly Thr Gly Gln Thr
145                 150                 155                 160

Asp Val Arg Arg Lys Ser Ala Ser Ser Arg Thr Pro Leu Thr His Ala
                165                 170                 175

Leu Pro Gly Leu Ser Glu Arg Glu Gly Gln Gln Thr Ser Ala Ala Ala
            180                 185                 190

Pro Thr Pro Pro Gln Ala Ser Pro Leu Leu Leu Leu Gly Leu Ala Leu
            195                 200                 205

Ala Leu Pro Ala Ala Ala Pro Arg Gly Arg
210                 215

<210> SEQ ID NO 68
<211> LENGTH: 103
<212> TYPE: PRT
<213> ORGANISM: Artificial
<220> FEATURE:
<223> OTHER INFORMATION: synthetic

<400> SEQUENCE: 68

Met Arg Leu Arg Leu Arg Leu Leu Ala Leu Leu Leu Leu Leu Leu Ala
  1               5                  10                  15

Pro Pro Ala Arg Ala Pro Lys Arg Ser Tyr Pro Tyr Asp Val Pro Asp
                 20                  25                  30
```

```
Tyr Ala Tyr Pro Tyr Asp Val Pro Asp Tyr Ala Ala Ser Gly Ala Ala
            35                  40                  45

Ala Ile Asp Pro Ser Ser Gly Pro Arg Ala Pro Arg Pro Lys Ala
 50                  55                  60

Thr Pro Val Ser Glu Thr Cys Asp Cys Gln Cys Glu Leu Asn Gln Ala
 65                  70                  75                  80

Ala Gly Arg Trp Pro Ala Pro Ile Pro Leu Leu Leu Pro Leu Leu
            85                  90                  95

Val Gly Gly Val Ala Ser Arg
            100
```

```
<210> SEQ ID NO 69
<211> LENGTH: 116
<212> TYPE: PRT
<213> ORGANISM: Artificial
<220> FEATURE:
<223> OTHER INFORMATION: synthetic

<400> SEQUENCE: 69

Met Arg Leu Arg Leu Arg Leu Leu Ala Leu Leu Leu Leu Leu Leu Ala
 1               5                  10                  15

Pro Pro Ala Arg Ala Pro Lys Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
            35                  40                  45

Ala Ile Asp Gly Thr Ser Leu Pro Val Asp Asn Ala Phe Pro Ala Pro
 50                  55                  60

Pro Ser Ser Gly Pro Arg Ala Pro Arg Pro Lys Ala Thr Pro Val
 65                  70                  75                  80

Ser Glu Thr Cys Asp Cys Gln Cys Glu Leu Asn Gln Ala Ala Gly Arg
                 85                  90                  95

Trp Pro Ala Pro Ile Pro Leu Leu Leu Pro Leu Leu Val Gly Gly
            100                 105                 110

Val Ala Ser Arg
        115
```

```
<210> SEQ ID NO 70
<211> LENGTH: 173
<212> TYPE: PRT
<213> ORGANISM: Artificial
<220> FEATURE:
<223> OTHER INFORMATION: synthetic

<400> SEQUENCE: 70

Met Arg Leu Arg Leu Arg Leu Leu Ala Leu Leu Leu Leu Leu Leu Ala
 1               5                  10                  15

Pro Pro Ala Arg Ala Pro Lys Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
            35                  40                  45

Ala Ile Asp Asn Gln Ser Asp Ile Val Ala His Leu Leu Ser Ser Ser
 50                  55                  60

Ser Ser Val Ile Asp Ala Leu Gln Tyr Lys Leu Glu Gly Thr Thr Arg
 65                  70                  75                  80

Leu Thr Arg Lys Arg Gly Leu Lys Leu Ala Thr Ala Leu Ser Leu Ser
            85                  90                  95

Asn Lys Phe Val Glu Gly Ser His Asn Ser Thr Val Ser Leu Thr Thr
            100                 105                 110
```

```
Lys Asn Met Glu Val Ser Val Ala Thr Pro Ser Ser Gly Pro Arg Ala
        115                 120                 125

Pro Arg Pro Pro Lys Ala Thr Pro Val Ser Glu Thr Cys Asp Cys Gln
    130                 135                 140

Cys Glu Leu Asn Gln Ala Ala Gly Arg Trp Pro Ala Pro Ile Pro Leu
145                 150                 155                 160

Leu Leu Leu Pro Leu Leu Val Gly Gly Val Ala Ser Arg
                165                 170
```

<210> SEQ ID NO 71
<211> LENGTH: 283
<212> TYPE: PRT
<213> ORGANISM: Artificial
<220> FEATURE:
<223> OTHER INFORMATION: synthetic

<400> SEQUENCE: 71

```
Met Arg Leu Arg Leu Arg Leu Leu Ala Leu Leu Leu Leu Leu Leu Ala
1               5                   10                  15

Pro Pro Ala Arg Ala Pro Lys Arg Ser Tyr Pro Tyr Asp Val Pro Asp
                20                  25                  30

Tyr Ala Tyr Pro Tyr Asp Val Pro Asp Tyr Ala Ala Ser Gly Ala Ala
            35                  40                  45

Ala Ile Asp Asn Gln Ser Asp Ile Val Ala His Leu Leu Ser Ser Ser
    50                  55                  60

Ser Ser Val Ile Asp Ala Leu Gln Tyr Lys Leu Glu Gly Thr Thr Arg
65                  70                  75                  80

Leu Thr Arg Lys Arg Gly Leu Lys Leu Ala Thr Ala Leu Ser Leu Ser
                85                  90                  95

Asn Lys Phe Val Glu Gly Ser His Asn Ser Thr Val Ser Leu Thr Thr
                100                 105                 110

Lys Asn Met Glu Val Ser Val Ala Thr Thr Thr Lys Ala Gln Ile Pro
            115                 120                 125

Ile Leu Arg Met Asn Phe Lys Gln Glu Leu Asn Gly Asn Thr Lys Ser
    130                 135                 140

Lys Pro Thr Val Ser Ser Ser Met Glu Phe Lys Tyr Asp Phe Asn Ser
145                 150                 155                 160

Ser Met Leu Tyr Ser Thr Ala Lys Gly Ala Val Asp His Lys Leu Ser
                165                 170                 175

Leu Glu Ser Leu Thr Ser Tyr Phe Ser Ile Glu Ser Thr Lys Gly
                180                 185                 190

Asp Val Lys Gly Ser Val Leu Ser Arg Glu Tyr Ser Gly Thr Ile Ala
            195                 200                 205

Ser Glu Ala Asn Thr Tyr Leu Asn Ser Lys Ser Thr Gln Ser Ser Val
    210                 215                 220

Lys Leu Gln Gly Thr Ser Lys Pro Ser Ser Gly Pro Arg Ala Pro Arg
225                 230                 235                 240

Pro Pro Lys Ala Thr Pro Val Ser Glu Thr Cys Asp Cys Gln Cys Glu
                245                 250                 255

Leu Asn Gln Ala Ala Gly Arg Trp Pro Ala Pro Ile Pro Leu Leu Leu
                260                 265                 270

Leu Pro Leu Leu Val Gly Gly Val Ala Ser Arg
                275                 280
```

<210> SEQ ID NO 72
<211> LENGTH: 170

```
<212> TYPE: PRT
<213> ORGANISM: Artificial
<220> FEATURE:
<223> OTHER INFORMATION: synthetic

<400> SEQUENCE: 72

Met Arg Leu Arg Leu Arg Leu Leu Ala Leu Leu Leu Leu Leu Leu Ala
1               5                   10                  15

Pro Pro Ala Arg Ala Pro Lys Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
            35                  40                  45

Ala Ile Asp Gly Thr Ser Leu Pro Val Asp Asn Ala Phe Pro Ala Pro
    50                  55                  60

Asp Cys Arg Glu Glu Gln Tyr Pro Cys Thr Arg Leu Tyr Ser Ile His
65                  70                  75                  80

Arg Pro Cys Lys Gln Cys Leu Asn Gly Val Cys Phe Tyr Ser Leu Arg
                85                  90                  95

Arg Val Tyr Val Ile Asn Lys Glu Ile Cys Val Arg Thr Val Cys Ala
                100                 105                 110

His Glu Glu Leu Leu Arg Pro Ser Ser Gly Pro Arg Ala Pro Arg Pro
            115                 120                 125

Pro Lys Ala Thr Pro Val Ser Glu Thr Cys Asp Cys Gln Cys Glu Leu
    130                 135                 140

Asn Gln Ala Ala Gly Arg Trp Pro Ala Pro Ile Pro Leu Leu Leu Leu
145                 150                 155                 160

Pro Leu Leu Val Gly Gly Val Ala Ser Arg
                165                 170

<210> SEQ ID NO 73
<211> LENGTH: 125
<212> TYPE: PRT
<213> ORGANISM: Artificial
<220> FEATURE:
<223> OTHER INFORMATION: synthetic

<400> SEQUENCE: 73

Met Arg Leu Arg Leu Arg Leu Leu Ala Leu Leu Leu Leu Leu Leu Ala
1               5                   10                  15

Pro Pro Ala Arg Ala Pro Lys Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
            35                  40                  45

Ala Ile Asp Gly Pro Thr Asp Arg Val Lys Glu Gly His Ser Pro Pro
    50                  55                  60

Asp Asp Val Asp Ile Val Ile Lys Leu Asp Asn Thr Ala Ser Thr Val
65                  70                  75                  80

Lys Ala Ile Ala Ile Val Ile Pro Cys Ile Leu Ala Leu Cys Leu Leu
                85                  90                  95

Val Leu Val Tyr Thr Val Phe Gln Phe Lys Arg Lys Gly Thr Pro Arg
                100                 105                 110

His Ala Leu Ala Cys Lys Arg Ser Met Gln Glu Trp Val
            115                 120                 125

<210> SEQ ID NO 74
<211> LENGTH: 132
<212> TYPE: PRT
<213> ORGANISM: Artificial
<220> FEATURE:
```

<223> OTHER INFORMATION: synthetic

<400> SEQUENCE: 74

Met Arg Leu Arg Leu Arg Leu Ala Leu Leu Leu Leu Leu Ala
1               5                   10                  15

Pro Pro Ala Arg Ala Pro Lys Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
        35                  40                  45

Ala Ile Asp Thr Cys Glu Gly Arg Asn Ser Cys Val Ser Cys Phe Asn
50                  55                  60

Val Ser Val Val Asn Thr Thr Cys Phe Trp Ile Glu Cys Lys Asp Glu
65                  70                  75                  80

Ser Asn Thr Ala Ser Thr Val Lys Ala Ile Ala Val Ile Pro Cys
            85                  90                  95

Ile Leu Ala Leu Cys Leu Leu Val Leu Val Tyr Thr Val Phe Gln Phe
            100                 105                 110

Lys Arg Lys Gly Thr Pro Arg His Ala Leu Ala Cys Lys Arg Ser Met
        115                 120                 125

Gln Glu Trp Val
    130

<210> SEQ ID NO 75
<211> LENGTH: 115
<212> TYPE: PRT
<213> ORGANISM: Artificial
<220> FEATURE:
<223> OTHER INFORMATION: synthetic

<400> SEQUENCE: 75

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
            85                  90                  95

Thr Asn Glu Asn Phe Val Asp Ala Tyr Glu Asn Ser Asn Ser Thr Glu
            100                 105                 110

Phe Val Ser
    115

<210> SEQ ID NO 76
<211> LENGTH: 142
<212> TYPE: PRT
<213> ORGANISM: Artificial
<220> FEATURE:
<223> OTHER INFORMATION: synthetic

<400> SEQUENCE: 76

Met Leu Leu Leu Phe His Ser Lys Arg Met Pro Val Ala Glu Ala Pro
1               5                   10                  15

Gln Val Ala Gly Gly Gln Gly Asp Gly Gly Asp Gly Glu Glu Ala Glu
            20                  25                  30

```
Pro Glu Gly Met Phe Lys Ala Cys Glu Asp Ser Lys Arg Lys Ala Arg
            35                  40                  45

Gly Tyr Leu Arg Leu Val Pro Leu Phe Val Leu Leu Ala Leu Leu Val
    50                  55                  60

Leu Ala Ser Ala Gly Val Leu Leu Trp Tyr Phe Leu Gly Tyr Lys Ala
65                  70                  75                  80

Glu Val Met Val Ser Gln Val Tyr Ser Gly Ser Leu Arg Val Leu Asn
                85                  90                  95

Arg His Phe Ser Gln Asp Leu Thr Arg Arg Glu Ser Ser Ala Phe Arg
            100                 105                 110

Ser Glu Thr Ala Lys Ala Gln Lys Met Leu Lys Glu Leu Ile Thr Ser
            115                 120                 125

Thr Arg Leu Gly Thr Tyr Tyr Asn Ser Ser Ser Val Tyr Ser
            130                 135                 140
```

```
<210> SEQ ID NO 77
<211> LENGTH: 34
<212> TYPE: PRT
<213> ORGANISM: Artificial
<220> FEATURE:
<223> OTHER INFORMATION: synthetic

<400> SEQUENCE: 77

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Val
            20                  25                  30

Trp Gly
```

```
<210> SEQ ID NO 78
<211> LENGTH: 65
<212> TYPE: PRT
<213> ORGANISM: Artificial
<220> FEATURE:
<223> OTHER INFORMATION: synthetic

<400> SEQUENCE: 78

Val Phe Asp Val Leu Ile Ser Gly Asp Pro Asn Phe Thr Val Ala Ala
1               5                   10                  15

Gln Ala Ala Leu Glu Asp Ala Arg Ala Phe Leu Pro Asp Leu Glu Lys
            20                  25                  30

Leu His Leu Phe Pro Ser Asp Ala Gly Val Pro Leu Ser Ser Ala Thr
            35                  40                  45

Leu Leu Ala Pro Leu Leu Ser Gly Leu Phe Val Leu Trp Leu Cys Ile
            50                  55                  60

Gln
65
```

```
<210> SEQ ID NO 79
<211> LENGTH: 114
<212> TYPE: PRT
<213> ORGANISM: Artificial
<220> FEATURE:
<223> OTHER INFORMATION: synthetic

<400> SEQUENCE: 79

Asp Leu Gln Leu Cys Val Gly Val Cys Pro Pro Ser Gln Arg Leu Ser
1               5                   10                  15

Arg Ser Glu Arg Asn Arg Arg Gly Ala Ile Thr Ile Asp Thr Ala Arg
            20                  25                  30
```

Arg Leu Cys Lys Glu Gly Leu Pro Val Glu Asp Ala Tyr Phe His Ser
            35                  40                  45

Cys Val Phe Asp Val Leu Ile Ser Gly Asp Pro Asn Phe Thr Val Ala
 50                  55                  60

Ala Gln Ala Ala Leu Glu Asp Ala Arg Ala Phe Leu Pro Asp Leu Glu
 65                  70                  75                  80

Lys Leu His Leu Phe Pro Ser Asp Ala Gly Val Pro Leu Ser Ser Ala
                85                  90                  95

Thr Leu Leu Ala Pro Leu Leu Ser Gly Leu Phe Val Leu Trp Leu Cys
            100                 105                 110

Ile Gln

<210> SEQ ID NO 80
<211> LENGTH: 54
<212> TYPE: PRT
<213> ORGANISM: Artificial
<220> FEATURE:
<223> OTHER INFORMATION: synthetic

<400> SEQUENCE: 80

Glu Cys Arg Asp Glu Lys Phe Ala Cys Thr Arg Leu Tyr Ser Val His
 1               5                  10                  15

Arg Pro Cys Lys Gln Cys Leu His Gln Ile Cys Phe Thr Ser Ser Arg
                20                  25                  30

Arg Met Tyr Val Ile Asn Asn Glu Ile Cys Ser Arg Leu Val Cys Lys
            35                  40                  45

Glu His Glu Ala Met Lys
         50

<210> SEQ ID NO 81
<211> LENGTH: 19
<212> TYPE: PRT
<213> ORGANISM: Artificial
<220> FEATURE:
<223> OTHER INFORMATION: synthetic

<400> SEQUENCE: 81

Met Asn Leu Ala Ile Ser Ile Ala Leu Leu Leu Thr Val Leu Gln Val
 1               5                  10                  15

Ser Arg Gly

<210> SEQ ID NO 82
<211> LENGTH: 50
<212> TYPE: PRT
<213> ORGANISM: Artificial
<220> FEATURE:
<223> OTHER INFORMATION: synthetic

<400> SEQUENCE: 82

Ser Pro Pro Ile Ser Ser Gln Asn Val Thr Val Leu Arg Asp Lys Leu
 1               5                  10                  15

Val Lys Cys Glu Gly Ile Ser Leu Leu Ala Gln Asn Thr Ser Trp Leu
                20                  25                  30

Leu Leu Leu Leu Leu Ser Leu Ser Leu Gln Ala Thr Asp Phe Met
            35                  40                  45

Ser Leu
     50

<210> SEQ ID NO 83
<211> LENGTH: 102

```
<212> TYPE: PRT
<213> ORGANISM: Artificial
<220> FEATURE:
<223> OTHER INFORMATION: synthetic

<400> SEQUENCE: 83

Pro Pro Pro Gln Pro Gly Gly His Thr Val Gly Ala Gly Val Gly Ser
1               5                   10                  15

Pro Ser Ser Gln Leu Tyr Glu His Thr Val Glu Gly Gly Glu Lys Gln
            20                  25                  30

Val Val Phe Thr His Arg Ile Asn Leu Pro Pro Ser Thr Gly Cys Gly
        35                  40                  45

Cys Pro Pro Gly Thr Glu Pro Pro Val Leu Ala Ser Glu Val Gln Ala
    50                  55                  60

Leu Arg Val Arg Leu Glu Ile Leu Glu Glu Leu Val Lys Gly Leu Lys
65                  70                  75                  80

Glu Gln Cys Thr Gly Gly Cys Cys Pro Ala Ser Ala Gln Ala Gly Thr
                85                  90                  95

Gly Gln Thr Asp Val Arg
            100

<210> SEQ ID NO 84
<211> LENGTH: 70
<212> TYPE: PRT
<213> ORGANISM: Artificial
<220> FEATURE:
<223> OTHER INFORMATION: synthetic

<400> SEQUENCE: 84

Asn Gln Ser Asp Ile Val Ala His Leu Leu Ser Ser Ser Ser Ser Val
1               5                   10                  15

Ile Asp Ala Leu Gln Tyr Lys Leu Glu Gly Thr Thr Arg Leu Thr Arg
            20                  25                  30

Lys Arg Gly Leu Lys Leu Ala Thr Ala Leu Ser Leu Ser Asn Lys Phe
        35                  40                  45

Val Glu Gly Ser His Asn Ser Thr Val Ser Leu Thr Thr Lys Asn Met
    50                  55                  60

Glu Val Ser Val Ala Thr
65                  70

<210> SEQ ID NO 85
<211> LENGTH: 23
<212> TYPE: PRT
<213> ORGANISM: Artificial
<220> FEATURE:
<223> OTHER INFORMATION: synthetic

<400> SEQUENCE: 85

Met Glu Leu Arg Ala Arg Gly Trp Trp Leu Leu Tyr Ala Ala Ala Val
1               5                   10                  15

Leu Val Ala Cys Ala Arg Gly
            20

<210> SEQ ID NO 86
<211> LENGTH: 55
<212> TYPE: PRT
<213> ORGANISM: Artificial
<220> FEATURE:
<223> OTHER INFORMATION: synthetic

<400> SEQUENCE: 86

Arg Lys Ser Ala Ser Ser Arg Thr Pro Leu Thr His Ala Leu Pro Gly
```

```
                1               5                   10                  15
Leu Ser Glu Arg Glu Gly Gln Gln Thr Ser Ala Ala Ala Pro Thr Pro
                20                  25                  30

Pro Gln Ala Ser Pro Leu Leu Leu Gly Leu Ala Leu Ala Leu Pro
        35                  40                  45

Ala Ala Ala Pro Arg Gly Arg
        50                  55

<210> SEQ ID NO 87
<211> LENGTH: 23
<212> TYPE: PRT
<213> ORGANISM: Artificial
<220> FEATURE:
<223> OTHER INFORMATION: synthetic

<400> SEQUENCE: 87

Met Arg Leu Arg Leu Arg Leu Ala Leu Leu Leu Leu Leu Ala
1               5                   10                  15

Pro Pro Ala Arg Ala Pro Lys
            20

<210> SEQ ID NO 88
<211> LENGTH: 52
<212> TYPE: PRT
<213> ORGANISM: Artificial
<220> FEATURE:
<223> OTHER INFORMATION: synthetic

<400> SEQUENCE: 88

Pro Ser Ser Gly Pro Arg Ala Pro Arg Pro Lys Ala Thr Pro Val
1               5                   10                  15

Ser Glu Thr Cys Asp Cys Gln Cys Glu Leu Asn Gln Ala Ala Gly Arg
                20                  25                  30

Trp Pro Ala Pro Ile Pro Leu Leu Leu Pro Leu Leu Val Gly Gly
        35                  40                  45

Val Ala Ser Arg
        50

<210> SEQ ID NO 89
<211> LENGTH: 180
<212> TYPE: PRT
<213> ORGANISM: Artificial
<220> FEATURE:
<223> OTHER INFORMATION: synthetic

<400> SEQUENCE: 89

Asn Gln Ser Asp Ile Val Ala His Leu Leu Ser Ser Ser Ser Val
1               5                   10                  15

Ile Asp Ala Leu Gln Tyr Lys Leu Glu Gly Thr Thr Arg Leu Thr Arg
                20                  25                  30

Lys Arg Gly Leu Lys Leu Ala Thr Ala Leu Ser Leu Ser Asn Lys Phe
        35                  40                  45

Val Glu Gly Ser His Asn Ser Thr Val Ser Leu Thr Thr Lys Asn Met
    50                  55                  60

Glu Val Ser Val Ala Thr Thr Thr Lys Ala Gln Ile Pro Ile Leu Arg
65                  70                  75                  80

Met Asn Phe Lys Gln Glu Leu Asn Gly Asn Thr Lys Ser Lys Pro Thr
                85                  90                  95

Val Ser Ser Ser Met Glu Phe Lys Tyr Asp Phe Asn Ser Ser Met Leu
            100                 105                 110
```

```
Tyr Ser Thr Ala Lys Gly Ala Val Asp His Lys Leu Ser Leu Glu Ser
        115                 120                 125
Leu Thr Ser Tyr Phe Ser Ile Glu Ser Ser Thr Lys Gly Asp Val Lys
    130                 135                 140
Gly Ser Val Leu Ser Arg Glu Tyr Ser Gly Thr Ile Ala Ser Glu Ala
145                 150                 155                 160
Asn Thr Tyr Leu Asn Ser Lys Ser Thr Gln Ser Ser Val Lys Leu Gln
                165                 170                 175
Gly Thr Ser Lys
            180

<210> SEQ ID NO 90
<211> LENGTH: 54
<212> TYPE: PRT
<213> ORGANISM: Artificial
<220> FEATURE:
<223> OTHER INFORMATION: synthetic

<400> SEQUENCE: 90

Asp Cys Arg Glu Glu Gln Tyr Pro Cys Thr Arg Leu Tyr Ser Ile His
1               5                   10                  15
Arg Pro Cys Lys Gln Cys Leu Asn Glu Val Cys Phe Tyr Ser Leu Arg
            20                  25                  30
Arg Val Tyr Val Ile Asn Lys Glu Ile Cys Val Arg Thr Val Cys Ala
        35                  40                  45
His Glu Glu Leu Leu Arg
    50

<210> SEQ ID NO 91
<211> LENGTH: 74
<212> TYPE: PRT
<213> ORGANISM: Artificial
<220> FEATURE:
<223> OTHER INFORMATION: synthetic

<400> SEQUENCE: 91

Gly Pro Thr Asp Arg Val Lys Glu Gly His Ser Pro Pro Asp Val
1               5                   10                  15
Asp Ile Val Ile Lys Leu Asp Asn Thr Ala Ser Thr Val Lys Ala Ile
            20                  25                  30
Ala Ile Val Ile Pro Cys Ile Leu Ala Leu Cys Leu Leu Val Leu Val
        35                  40                  45
Tyr Thr Val Phe Gln Lys Arg Lys Gly Thr Pro Arg His Ala Leu
    50                  55                  60
Ala Cys Lys Arg Ser Met Gln Glu Trp Val
65                  70

<210> SEQ ID NO 92
<211> LENGTH: 30
<212> TYPE: PRT
<213> ORGANISM: Artificial
<220> FEATURE:
<223> OTHER INFORMATION: synthetic

<400> SEQUENCE: 92

Thr Cys Glu Gly Arg Asn Ser Cys Val Ser Cys Phe Asn Val Ser Val
1               5                   10                  15
Val Asn Thr Thr Cys Phe Trp Ile Glu Cys Lys Asp Glu Ser
            20                  25                  30

<210> SEQ ID NO 93
```

```
<211> LENGTH: 51
<212> TYPE: PRT
<213> ORGANISM: Artificial
<220> FEATURE:
<223> OTHER INFORMATION: synthetic

<400> SEQUENCE: 93

Asn Thr Ala Ser Thr Val Lys Ala Ile Ala Ile Val Pro Cys Ile
1               5                   10                  15

Leu Ala Leu Cys Leu Leu Val Leu Val Tyr Thr Val Phe Gln Phe Lys
            20                  25                  30

Arg Lys Gly Thr Pro Arg His Ala Leu Ala Cys Lys Arg Ser Met Gln
        35                  40                  45

Glu Trp Val
    50

<210> SEQ ID NO 94
<211> LENGTH: 115
<212> TYPE: PRT
<213> ORGANISM: Artificial
<220> FEATURE:
<223> OTHER INFORMATION: synthetic

<400> SEQUENCE: 94

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser
        115

<210> SEQ ID NO 95
<211> LENGTH: 142
<212> TYPE: PRT
<213> ORGANISM: Artificial
<220> FEATURE:
<223> OTHER INFORMATION: synthetic

<400> SEQUENCE: 95

Met Leu Leu Leu Phe His Ser Lys Arg Met Pro Val Ala Glu Ala Pro
1               5                   10                  15

Gln Val Ala Gly Gly Gln Gly Asp Gly Gly Asp Gly Glu Gly Ala Glu
            20                  25                  30

Pro Glu Gly Met Phe Lys Ala Cys Glu Asp Ser Lys Arg Lys Ala Arg
        35                  40                  45

Gly Tyr Leu Arg Leu Val Pro Leu Phe Val Leu Leu Ala Leu Leu Val
    50                  55                  60

Leu Ala Ser Ala Gly Val Leu Leu Trp Tyr Phe Leu Gly Tyr Lys Ala
65                  70                  75                  80

Glu Val Met Val Ser Gln Val Tyr Ser Gly Ser Leu Arg Val Leu Asn
```

```
                85                  90                  95
Arg His Phe Ser Gln Asp Leu Thr Arg Arg Glu Ser Ser Ala Phe Arg
            100                 105                 110

Ser Glu Thr Ala Lys Ala Gln Lys Met Leu Lys Glu Leu Ile Thr Ser
        115                 120                 125

Thr Arg Leu Gly Thr Tyr Tyr Asn Ser Ser Val Tyr Ser
    130                 135                 140

<210> SEQ ID NO 96
<211> LENGTH: 28
<212> TYPE: PRT
<213> ORGANISM: Artificial
<220> FEATURE:
<223> OTHER INFORMATION: synthetic

<400> SEQUENCE: 96

Arg Ser Tyr Pro Tyr Asp Val Pro Asp Tyr Ala Tyr Pro Tyr Asp Val
1               5                   10                  15

Pro Asp Tyr Ala Ala Ser Gly Ala Ala Ile Asp
            20                  25

<210> SEQ ID NO 97
<211> LENGTH: 8
<212> TYPE: PRT
<213> ORGANISM: Artificial
<220> FEATURE:
<223> OTHER INFORMATION: synthetic

<400> SEQUENCE: 97

Gly Ser Pro Lys Pro Pro Glu Ala
1               5

<210> SEQ ID NO 98
<211> LENGTH: 10
<212> TYPE: PRT
<213> ORGANISM: Artificial
<220> FEATURE:
<223> OTHER INFORMATION: synthetic

<400> SEQUENCE: 98

Gln Lys Gly Ser Val Gly Phe Ala Asp Pro
1               5                   10

<210> SEQ ID NO 99
<211> LENGTH: 13
<212> TYPE: PRT
<213> ORGANISM: Artificial
<220> FEATURE:
<223> OTHER INFORMATION: synthetic

<400> SEQUENCE: 99

Gly Thr Ser Leu Pro Val Asp Asn Ala Phe Pro Ala Pro
1               5                   10

<210> SEQ ID NO 100
<211> LENGTH: 156
<212> TYPE: PRT
<213> ORGANISM: Artificial
<220> FEATURE:
<223> OTHER INFORMATION: synthetic

<400> SEQUENCE: 100

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
```

-continued

```
                    20                  25                  30
Asp Pro Pro Val Ala Ala Val Val Ser His Phe Asn Asp Arg Ser
            35                  40                  45

Tyr Pro Tyr Asp Val Pro Asp Tyr Ala Tyr Pro Tyr Asp Val Pro Asp
        50                  55                  60

Tyr Ala Ala Ser Gly Ala Ala Ile Asp Gly Ala Arg Cys Glu His
65                  70                  75                  80

Ala Asp Leu Leu Ala Val Val Ala Ser Gln Lys Lys Gln Ala Ile
                85                  90                  95

Thr Ala Leu Val Val Ser Ile Val Ala Leu Ala Val Leu Ile Ile
            100                 105                 110

Thr Cys Val Leu Ile His Cys Cys Gln Val Arg Lys His Cys Glu Trp
        115                 120                 125

Cys Arg Ala Leu Ile Cys Arg His Glu Lys Pro Ser Ala Leu Leu Lys
130                 135                 140

Gly Arg Thr Ala Cys Cys His Ser Glu Thr Val Val
145                 150                 155

<210> SEQ ID NO 101
<211> LENGTH: 155
<212> TYPE: PRT
<213> ORGANISM: Artificial
<220> FEATURE:
<223> OTHER INFORMATION: synthetic

<400> SEQUENCE: 101

Gly Gly Gly Pro Val Ala Gln Ala Val Val Ser Ser Gly Pro Gly Ser
1               5                   10                  15

Phe Ser Leu Asn Phe Thr Leu Pro Ala Asn Thr Thr Ser Ser Pro Val
            20                  25                  30

Thr Gly Gly Lys Glu Thr Asp Cys Gly Pro Ser Leu Gly Leu Ala Ala
        35                  40                  45

Gly Ile Pro Leu Leu Val Ala Thr Ala Leu Leu Val Ala Leu Leu Phe
    50                  55                  60

Thr Leu Ile His Arg Arg Ser Ser Ile Glu Ala Met Glu Glu Ser
65                  70                  75                  80

Asp Arg Pro Cys Glu Ile Ser Glu Ile Asp Asp Asn Pro Lys Ile Ser
                85                  90                  95

Glu Asn Pro Arg Arg Ser Pro Thr His Glu Lys Asn Thr Met Gly Ala
            100                 105                 110

Gln Glu Ala His Ile Tyr Val Lys Thr Val Ala Gly Ser Glu Glu Pro
        115                 120                 125

Val His Asp Arg Tyr Arg Pro Thr Ile Glu Met Glu Arg Arg Gly
    130                 135                 140

Leu Trp Trp Leu Val Pro Arg Leu Ser Leu Glu
145                 150                 155

<210> SEQ ID NO 102
<211> LENGTH: 213
<212> TYPE: PRT
<213> ORGANISM: Artificial
<220> FEATURE:
<223> OTHER INFORMATION: synthetic

<400> SEQUENCE: 102

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Arg Ser
```

```
                20                  25                  30

Tyr Pro Tyr Asp Val Pro Asp Tyr Ala Tyr Pro Tyr Asp Val Pro Asp
            35                  40                  45

Tyr Ala Ala Ser Gly Ala Ala Ala Ile Asp Gly Gly Gly Pro Val Ala
        50                  55                  60

Gln Ala Val Val Ser Ser Gly Pro Gly Ser Phe Ser Leu Asn Phe Thr
65                  70                  75                  80

Leu Pro Ala Asn Thr Thr Ser Ser Pro Val Thr Gly Gly Lys Glu Thr
                85                  90                  95

Asp Cys Gly Pro Ser Leu Gly Leu Ala Ala Gly Ile Pro Leu Leu Val
            100                 105                 110

Ala Thr Ala Leu Leu Val Ala Leu Leu Phe Thr Leu Ile His Arg Arg
        115                 120                 125

Arg Ser Ser Ile Glu Ala Met Glu Glu Ser Asp Arg Pro Cys Glu Ile
    130                 135                 140

Ser Glu Ile Asp Asp Asn Pro Lys Ile Ser Glu Asn Pro Arg Arg Ser
145                 150                 155                 160

Pro Thr His Glu Lys Asn Thr Met Gly Ala Gln Glu Ala His Ile Tyr
                165                 170                 175

Val Lys Thr Val Ala Gly Ser Glu Glu Pro Val His Asp Arg Tyr Arg
            180                 185                 190

Pro Thr Ile Glu Met Glu Arg Arg Arg Gly Leu Trp Trp Leu Val Pro
        195                 200                 205

Arg Leu Ser Leu Glu
    210

<210> SEQ ID NO 103
<211> LENGTH: 228
<212> TYPE: PRT
<213> ORGANISM: Artificial
<220> FEATURE:
<223> OTHER INFORMATION: synthetic

<400> SEQUENCE: 103

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Arg Ser
            20                  25                  30

Tyr Pro Tyr Asp Val Pro Asp Tyr Ala Tyr Pro Tyr Asp Val Pro Asp
            35                  40                  45

Tyr Ala Ala Ser Gly Ala Ala Ala Ile Asp Gly Gly Gly Pro Val Ala
        50                  55                  60

Gln Ala Val Val Ser Ser Gly Pro Gly Ser Phe Ser Leu Asn Phe Thr
65                  70                  75                  80

Leu Pro Ala Asn Thr Thr Ser Ser Pro Val Thr Gly Gly Lys Glu Thr
                85                  90                  95

Asp Cys Gly Pro Ser Leu Gly Leu Ala Ala Gly Ile Pro Leu Leu Val
            100                 105                 110

Ala Thr Ala Leu Leu Val Ala Leu Leu Phe Thr Leu Ile His Arg Arg
        115                 120                 125

Arg Ser Ser Ile Glu Ala Met Glu Glu Ser Asp Arg Pro Cys Glu Ile
    130                 135                 140

Ser Glu Ile Asp Asp Asn Pro Lys Ile Ser Glu Asn Pro Arg Arg Ser
145                 150                 155                 160

Pro Thr His Glu Lys Asn Thr Met Gly Ala Gln Glu Ala His Ile Tyr
                165                 170                 175
```

Val Lys Thr Val Ala Gly Ser Glu Glu Pro Val His Asp Arg Tyr Arg
            180                 185                 190

Pro Thr Ile Glu Met Glu Arg Arg Arg Gly Leu Trp Trp Leu Val Pro
        195                 200                 205

Arg Leu Ser Leu Glu Pro Gly Gly Gly Arg Thr Ala Cys Cys His Ser
    210                 215                 220

Glu Thr Val Val
225

<210> SEQ ID NO 104
<211> LENGTH: 214
<212> TYPE: PRT
<213> ORGANISM: Artificial
<220> FEATURE:
<223> OTHER INFORMATION: synthetic

<400> SEQUENCE: 104

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Arg Ser
            20                  25                  30

Tyr Pro Tyr Asp Val Pro Asp Tyr Ala Tyr Pro Tyr Asp Val Pro Asp
        35                  40                  45

Tyr Ala Ser Gly Ala Ala Ile Asp Pro Lys Lys Cys Pro Gly
    50                  55                  60

Arg Val Val Gly Gly Cys Val Ala His Pro Ser Phe Ser Leu Asn Phe
65                  70                  75                  80

Thr Leu Pro Ala Asn Thr Thr Ser Ser Pro Val Thr Gly Gly Lys Glu
                85                  90                  95

Thr Asp Cys Gly Pro Ser Leu Gly Leu Ala Ala Gly Ile Pro Leu Leu
            100                 105                 110

Val Ala Thr Ala Leu Leu Val Ala Leu Leu Phe Thr Leu Ile His Arg
        115                 120                 125

Arg Arg Ser Ser Ile Glu Ala Met Glu Glu Ser Asp Arg Pro Cys Glu
    130                 135                 140

Ile Ser Glu Ile Asp Asp Asn Pro Lys Ile Ser Glu Asn Pro Arg Arg
145                 150                 155                 160

Ser Pro Thr His Glu Lys Asn Thr Met Gly Ala Gln Glu Ala His Ile
                165                 170                 175

Tyr Val Lys Thr Val Ala Gly Ser Glu Glu Pro Val His Asp Arg Tyr
            180                 185                 190

Arg Pro Thr Ile Glu Met Glu Arg Arg Arg Gly Leu Trp Trp Leu Val
        195                 200                 205

Pro Arg Leu Ser Leu Glu
    210

<210> SEQ ID NO 105
<211> LENGTH: 208
<212> TYPE: PRT
<213> ORGANISM: Artificial
<220> FEATURE:
<223> OTHER INFORMATION: synthetic

<400> SEQUENCE: 105

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Arg Ser
            20                  25                  30

```
Tyr Pro Tyr Asp Val Pro Asp Tyr Ala Tyr Pro Tyr Asp Val Pro Asp
            35                  40                  45

Tyr Ala Ala Ser Gly Ala Ala Ala Ile Asp Gly Ala Ser Gln Gly Leu
 50                  55                  60

Leu Asp Arg Lys Ser Phe Ser Leu Asn Phe Thr Leu Pro Ala Asn Thr
 65                  70                  75                  80

Thr Ser Ser Pro Val Thr Gly Lys Glu Thr Asp Cys Gly Pro Ser
                 85                  90                  95

Leu Gly Leu Ala Ala Gly Ile Pro Leu Leu Val Ala Thr Ala Leu Leu
            100                 105                 110

Val Ala Leu Leu Phe Thr Leu Ile His Arg Arg Ser Ser Ile Glu
            115                 120                 125

Ala Met Glu Glu Ser Asp Arg Pro Cys Glu Ile Ser Glu Ile Asp Asp
            130                 135                 140

Asn Pro Lys Ile Ser Glu Asn Pro Arg Arg Ser Pro Thr His Glu Lys
145                 150                 155                 160

Asn Thr Met Gly Ala Gln Glu Ala His Ile Tyr Val Lys Thr Val Ala
                165                 170                 175

Gly Ser Glu Glu Pro Val His Asp Arg Tyr Arg Pro Thr Ile Glu Met
                180                 185                 190

Glu Arg Arg Arg Gly Leu Trp Trp Leu Val Pro Arg Leu Ser Leu Glu
            195                 200                 205

<210> SEQ ID NO 106
<211> LENGTH: 226
<212> TYPE: PRT
<213> ORGANISM: Artificial
<220> FEATURE:
<223> OTHER INFORMATION: synthetic

<400> SEQUENCE: 106

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Arg Ser
            20                  25                  30

Tyr Pro Tyr Asp Val Pro Asp Tyr Ala Tyr Pro Tyr Asp Val Pro Asp
            35                  40                  45

Tyr Ala Ala Ser Gly Ala Ala Ala Ile Asp Gly Pro Glu Gly Leu Arg
 50                  55                  60

Val Gly Phe Tyr Glu Ser Asp Val Met Gly Arg Gly His Ala Arg Leu
 65                  70                  75                  80

Val His Val Glu Glu Pro Ser Phe Ser Leu Asn Phe Thr Leu Pro Ala
                85                  90                  95

Asn Thr Thr Ser Ser Pro Val Thr Gly Gly Lys Glu Thr Asp Cys Gly
            100                 105                 110

Pro Ser Leu Gly Leu Ala Ala Gly Ile Pro Leu Leu Val Ala Thr Ala
            115                 120                 125

Leu Leu Val Ala Leu Leu Phe Thr Leu Ile His Arg Arg Arg Ser Ser
130                 135                 140

Ile Glu Ala Met Glu Glu Ser Asp Arg Pro Cys Glu Ile Ser Glu Ile
145                 150                 155                 160

Asp Asp Asn Pro Lys Ile Ser Glu Asn Pro Arg Arg Ser Pro Thr His
                165                 170                 175

Glu Lys Asn Thr Met Gly Ala Gln Glu Ala His Ile Tyr Val Lys Thr
            180                 185                 190
```

Val Ala Gly Ser Glu Glu Pro Val His Asp Arg Tyr Arg Pro Thr Ile
        195                 200                 205

Glu Met Glu Arg Arg Gly Leu Trp Trp Leu Val Pro Arg Leu Ser
    210                 215                 220

Leu Glu
225

<210> SEQ ID NO 107
<211> LENGTH: 131
<212> TYPE: PRT
<213> ORGANISM: Artificial
<220> FEATURE:
<223> OTHER INFORMATION: synthetic

<400> SEQUENCE: 107

Met Glu Leu Arg Ala Arg Gly Trp Trp Leu Leu Tyr Ala Ala Ala Val
1               5                   10                  15

Leu Val Ala Cys Ala Arg Gly Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
        35                  40                  45

Ala Ile Asp Gly Pro Glu Gly Leu Arg Val Gly Phe Tyr Glu Ser Asp
    50                  55                  60

Val Met Gly Arg Gly His Ala Arg Leu Val His Val Glu Glu Pro Pro
65                  70                  75                  80

Ser Ser Gly Pro Arg Ala Pro Arg Pro Lys Ala Thr Pro Val Ser
                85                  90                  95

Glu Thr Cys Asp Cys Gln Cys Glu Leu Asn Gln Ala Ala Gly Arg Trp
            100                 105                 110

Pro Ala Pro Ile Pro Leu Leu Leu Pro Leu Leu Val Gly Gly Val
        115                 120                 125

Ala Ser Arg
    130

<210> SEQ ID NO 108
<211> LENGTH: 116
<212> TYPE: PRT
<213> ORGANISM: Artificial
<220> FEATURE:
<223> OTHER INFORMATION: synthetic

<400> SEQUENCE: 108

Met Glu Leu Arg Ala Arg Gly Trp Trp Leu Leu Tyr Ala Ala Ala Val
1               5                   10                  15

Leu Val Ala Cys Ala Arg Gly Arg Ser Tyr Pro Tyr Asp Val Pro Asp
            20                  25                  30

Tyr Ala Tyr Pro Tyr Asp Val Pro Asp Tyr Ala Ala Ser Gly Ala Ala
        35                  40                  45

Ala Ile Asp Pro Pro Val Ala Ala Val Val Ser His Phe Asn Asp
    50                  55                  60

Pro Ser Ser Gly Pro Arg Ala Pro Arg Pro Lys Ala Thr Pro Val
65                  70                  75                  80

Ser Glu Thr Cys Asp Cys Gln Cys Glu Leu Asn Gln Ala Ala Gly Arg
                85                  90                  95

Trp Pro Ala Pro Ile Pro Leu Leu Leu Pro Leu Leu Val Gly Gly
            100                 105                 110

Val Ala Ser Arg
    115

```
<210> SEQ ID NO 109
<211> LENGTH: 119
<212> TYPE: PRT
<213> ORGANISM: Artificial
<220> FEATURE:
<223> OTHER INFORMATION: synthetic

<400> SEQUENCE: 109

Met Glu Leu Arg Ala Arg Gly Trp Trp Leu Leu Tyr Ala Ala Ala Val
1               5                   10                  15

Leu Val Ala Cys Ala Arg Gly Arg Ser Tyr Pro Tyr Asp Val Pro Asp
                20                  25                  30

Tyr Ala Tyr Pro Tyr Asp Val Pro Asp Tyr Ala Ala Ser Gly Ala Ala
            35                  40                  45

Ala Ile Asp Pro Lys Lys Cys Pro Gly Arg Val Gly Gly Cys Val
50                  55                  60

Ala His Pro Pro Ser Ser Gly Pro Arg Ala Pro Arg Pro Lys Ala
65                  70                  75                  80

Thr Pro Val Ser Glu Thr Cys Asp Cys Gln Cys Glu Leu Asn Gln Ala
                85                  90                  95

Ala Gly Arg Trp Pro Ala Pro Ile Pro Leu Leu Leu Pro Leu Leu
            100                 105                 110

Val Gly Gly Val Ala Ser Arg
        115

<210> SEQ ID NO 110
<211> LENGTH: 113
<212> TYPE: PRT
<213> ORGANISM: Artificial
<220> FEATURE:
<223> OTHER INFORMATION: synthetic

<400> SEQUENCE: 110

Met Glu Leu Arg Ala Arg Gly Trp Trp Leu Leu Tyr Ala Ala Ala Val
1               5                   10                  15

Leu Val Ala Cys Ala Arg Gly Arg Ser Tyr Pro Tyr Asp Val Pro Asp
                20                  25                  30

Tyr Ala Tyr Pro Tyr Asp Val Pro Asp Tyr Ala Ala Ser Gly Ala Ala
            35                  40                  45

Ala Ile Asp Gly Ala Ser Gln Gly Leu Leu Asp Arg Lys Pro Ser Ser
50                  55                  60

Gly Pro Arg Ala Pro Arg Pro Pro Lys Ala Thr Pro Val Ser Glu Thr
65                  70                  75                  80

Cys Asp Cys Gln Cys Glu Leu Asn Gln Ala Ala Gly Arg Trp Pro Ala
                85                  90                  95

Pro Ile Pro Leu Leu Leu Leu Pro Leu Leu Val Gly Gly Val Ala Ser
            100                 105                 110

Arg

<210> SEQ ID NO 111
<211> LENGTH: 143
<212> TYPE: PRT
<213> ORGANISM: Artificial
<220> FEATURE:
<223> OTHER INFORMATION: synthetic

<400> SEQUENCE: 111

Pro Gly Gly Ser Phe Ser Leu Asn Phe Thr Leu Pro Ala Asn Thr Thr
1               5                   10                  15
```

```
Ser Ser Pro Val Thr Gly Gly Lys Glu Thr Asp Cys Gly Pro Ser Leu
         20                  25                  30

Gly Leu Ala Ala Gly Ile Pro Leu Val Ala Thr Ala Leu Leu Val
             35                  40                  45

Ala Leu Leu Phe Thr Leu Ile His Arg Arg Ser Ser Ile Glu Ala
 50                  55                  60

Met Glu Glu Ser Asp Arg Pro Cys Glu Ile Ser Ile Asp Asp Asn
 65                  70                  75                  80

Pro Lys Ile Ser Glu Asn Pro Arg Arg Ser Pro Thr His Glu Lys Asn
                 85                  90                  95

Thr Met Gly Ala Gln Glu Ala His Ile Tyr Val Lys Thr Val Ala Gly
                100                 105                 110

Ser Glu Glu Pro Val His Asp Arg Tyr Arg Pro Thr Ile Glu Met Glu
                115                 120                 125

Arg Arg Arg Gly Leu Trp Trp Leu Val Pro Arg Leu Ser Leu Glu
    130                 135                 140

<210> SEQ ID NO 112
<211> LENGTH: 22
<212> TYPE: PRT
<213> ORGANISM: Artificial
<220> FEATURE:
<223> OTHER INFORMATION: synthetic

<400> SEQUENCE: 112

Val Pro Ser Ala Gly Gln Leu Ala Leu Phe Ala Leu Gly Ile Val Leu
 1               5                  10                  15

Ala Ala Cys Gln Ala Leu
             20

<210> SEQ ID NO 113
<211> LENGTH: 10
<212> TYPE: PRT
<213> ORGANISM: Artificial
<220> FEATURE:
<223> OTHER INFORMATION: synthetic

<400> SEQUENCE: 113

Glu Asn Ser Thr Ser Pro Leu Ser Ala Asp
 1               5                  10

<210> SEQ ID NO 114
<211> LENGTH: 13
<212> TYPE: PRT
<213> ORGANISM: Artificial
<220> FEATURE:
<223> OTHER INFORMATION: synthetic

<400> SEQUENCE: 114

Pro Pro Val Ala Ala Ala Val Val Ser His Phe Asn Asp
 1               5                  10

<210> SEQ ID NO 115
<211> LENGTH: 16
<212> TYPE: PRT
<213> ORGANISM: Artificial
<220> FEATURE:
<223> OTHER INFORMATION: synthetic

<400> SEQUENCE: 115

Gly Ala Arg Cys Glu His Ala Asp Leu Leu Ala Val Val Ala Ala Ser
 1               5                  10                  15
```

```
<210> SEQ ID NO 116
<211> LENGTH: 4
<212> TYPE: PRT
<213> ORGANISM: Artificial
<220> FEATURE:
<223> OTHER INFORMATION: synthetic

<400> SEQUENCE: 116

Gln Lys Lys Gln
1

<210> SEQ ID NO 117
<211> LENGTH: 26
<212> TYPE: PRT
<213> ORGANISM: Artificial
<220> FEATURE:
<223> OTHER INFORMATION: synthetic

<400> SEQUENCE: 117

Ala Ile Thr Ala Leu Val Val Val Ser Ile Val Ala Leu Ala Val Leu
1               5                   10                  15

Ile Ile Thr Cys Val Leu Ile His Cys Cys
            20                  25

<210> SEQ ID NO 118
<211> LENGTH: 24
<212> TYPE: PRT
<213> ORGANISM: Artificial
<220> FEATURE:
<223> OTHER INFORMATION: synthetic

<400> SEQUENCE: 118

Gln Val Arg Lys His Cys Glu Trp Cys Arg Ala Leu Ile Cys Arg His
1               5                   10                  15

Glu Lys Pro Ser Ala Leu Leu Lys
            20

<210> SEQ ID NO 119
<211> LENGTH: 12
<212> TYPE: PRT
<213> ORGANISM: Artificial
<220> FEATURE:
<223> OTHER INFORMATION: synthetic

<400> SEQUENCE: 119

Gly Arg Thr Ala Cys Cys His Ser Glu Thr Val Val
1               5                   10

<210> SEQ ID NO 120
<211> LENGTH: 28
<212> TYPE: PRT
<213> ORGANISM: Artificial
<220> FEATURE:
<223> OTHER INFORMATION: synthetic

<400> SEQUENCE: 120

Ser Phe Ser Leu Asn Phe Thr Leu Pro Ala Asn Thr Thr Ser Ser Pro
1               5                   10                  15

Val Thr Gly Gly Lys Glu Thr Asp Cys Gly Pro Ser
            20                  25

<210> SEQ ID NO 121
<211> LENGTH: 24
<212> TYPE: PRT
<213> ORGANISM: Artificial
<220> FEATURE:
<223> OTHER INFORMATION: synthetic
```

```
<400> SEQUENCE: 121

Leu Gly Leu Ala Ala Gly Ile Pro Leu Leu Val Ala Thr Ala Leu Leu
1               5                   10                  15

Val Ala Leu Leu Phe Thr Leu Ile
            20

<210> SEQ ID NO 122
<211> LENGTH: 36
<212> TYPE: PRT
<213> ORGANISM: Artificial
<220> FEATURE:
<223> OTHER INFORMATION: synthetic

<400> SEQUENCE: 122

His Arg Arg Arg Ser Ser Ile Glu Ala Met Glu Glu Ser Asp Arg Pro
1               5                   10                  15

Cys Glu Ile Ser Glu Ile Asp Asp Asn Pro Lys Ile Ser Glu Asn Pro
            20                  25                  30

Arg Arg Ser Pro
        35

<210> SEQ ID NO 123
<211> LENGTH: 52
<212> TYPE: PRT
<213> ORGANISM: Artificial
<220> FEATURE:
<223> OTHER INFORMATION: synthetic

<400> SEQUENCE: 123

Thr His Glu Lys Asn Thr Met Gly Ala Gln Glu Ala His Ile Tyr Val
1               5                   10                  15

Lys Thr Val Ala Gly Ser Glu Glu Pro Val His Asp Arg Tyr Arg Pro
            20                  25                  30

Thr Ile Glu Met Glu Arg Arg Arg Gly Leu Trp Trp Leu Val Pro Arg
        35                  40                  45

Leu Ser Leu Glu
    50

<210> SEQ ID NO 124
<211> LENGTH: 30
<212> TYPE: PRT
<213> ORGANISM: Artificial
<220> FEATURE:
<223> OTHER INFORMATION: synthetic

<400> SEQUENCE: 124

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val
            20                  25                  30

<210> SEQ ID NO 125
<211> LENGTH: 16
<212> TYPE: PRT
<213> ORGANISM: Artificial
<220> FEATURE:
<223> OTHER INFORMATION: synthetic

<400> SEQUENCE: 125

Pro Lys Lys Cys Pro Gly Arg Val Val Gly Gly Cys Val Ala His Pro
1               5                   10                  15
```

```
<210> SEQ ID NO 126
<211> LENGTH: 10
<212> TYPE: PRT
<213> ORGANISM: Artificial
<220> FEATURE:
<223> OTHER INFORMATION: synthetic

<400> SEQUENCE: 126

Gly Ala Ser Gln Gly Leu Leu Asp Arg Lys
1               5                   10

<210> SEQ ID NO 127
<211> LENGTH: 28
<212> TYPE: PRT
<213> ORGANISM: Artificial
<220> FEATURE:
<223> OTHER INFORMATION: synthetic

<400> SEQUENCE: 127

Gly Pro Glu Gly Leu Arg Val Gly Phe Tyr Glu Ser Asp Val Met Gly
1               5                   10                  15

Arg Gly His Ala Arg Leu Val His Val Glu Glu Pro
            20                  25

<210> SEQ ID NO 128
<211> LENGTH: 23
<212> TYPE: PRT
<213> ORGANISM: Artificial
<220> FEATURE:
<223> OTHER INFORMATION: synthetic

<400> SEQUENCE: 128

Met Glu Leu Arg Ala Arg Gly Trp Trp Leu Leu Tyr Ala Ala Ala Val
1               5                   10                  15

Leu Val Ala Cys Ala Arg Gly
            20

<210> SEQ ID NO 129
<211> LENGTH: 52
<212> TYPE: PRT
<213> ORGANISM: Artificial
<220> FEATURE:
<223> OTHER INFORMATION: synthetic

<400> SEQUENCE: 129

Pro Ser Ser Gly Pro Arg Ala Pro Arg Pro Pro Lys Ala Thr Pro Val
1               5                   10                  15

Ser Glu Thr Cys Asp Cys Gln Cys Glu Leu Asn Gln Ala Ala Gly Arg
            20                  25                  30

Trp Pro Ala Pro Ile Pro Leu Leu Leu Pro Leu Leu Val Gly Gly
        35                  40                  45

Val Ala Ser Arg
    50

<210> SEQ ID NO 130
<211> LENGTH: 28
<212> TYPE: PRT
<213> ORGANISM: Artificial
<220> FEATURE:
<223> OTHER INFORMATION: synthetic

<400> SEQUENCE: 130

Arg Ser Tyr Pro Tyr Asp Val Pro Asp Tyr Ala Tyr Pro Tyr Asp Val
1               5                   10                  15

Pro Asp Tyr Ala Ala Ser Gly Ala Ala Ala Ile Asp
```

<210> SEQ ID NO 131
<211> LENGTH: 15
<212> TYPE: PRT
<213> ORGANISM: Artificial
<220> FEATURE:
<223> OTHER INFORMATION: synthetic

<400> SEQUENCE: 131

Gly Gly Gly Pro Val Ala Gln Ala Val Val Ser Ser Gly Pro Gly
1               5                   10                  15

<210> SEQ ID NO 132
<211> LENGTH: 785
<212> TYPE: DNA
<213> ORGANISM: Artificial
<220> FEATURE:
<223> OTHER INFORMATION: synthetic

<400> SEQUENCE: 132

```
gaattccttt ttatgcaaat gagccattcc cagcacccta gccccaccaa tcctgtactc      60
agatagcccc aaccatccct agaggtttag aaaaccttta tagtccaacc cccaactaaa     120
tgtgctactt tctgaatcct gtctcctctc cttccactca cctcatcttg ctcacttgct     180
gcctgaggtc tccatcaccc caatctgtaa gtccagttcc agctgtagac cttcttctgg     240
acttcttgga catccatgtg catccatgga cttcttgtgc atccatttgg ggcacataca     300
tacatacagg caaaacaccc atatatgtaa ataattttt tttttaagat tagcacctta     360
gtttactttt tgacagtttt ttgcttgttt gcttggttag ttggttggtt tggcttttg     420
agataacgtt tctctgtgta gctctggctg tcctgaaatt cactatgtag accaggctag     480
cttttgaaccc acagagatct ggctgcctct gctgggatta aaggcatagg ccaccacgat     540
tggctttgag aagaaataaa ctaataaagc aaataaaggc caattttatg tcactctatt     600
ttataacgat aaaacatgac ttagttatga gggaactgag acaggacact ttctaagaca     660
cctgtgtttc tgacaacagc ttacctcaga gcagcatgta aaatatttta aaaagggaaa     720
aagccaggtg tggtaatgct cacctgtaat cctagccctc tggaagttaa ggcaggaaaa     780
tcatg                                                                 785
```

<210> SEQ ID NO 133
<211> LENGTH: 458
<212> TYPE: DNA
<213> ORGANISM: Artificial
<220> FEATURE:
<223> OTHER INFORMATION: synthetic

<400> SEQUENCE: 133

```
ggaaggtttt cgtggtcctg cccataaaag gttttcccg ccaccctcag caccgccccg       60
ccccaacccc gcagcatctc caaagcatgc agagaatgtc tcgggctgcc cccgacagac     120
tgctccaact tggtgtcttt ccccaaatat ggagcctgtg tggagtgagt ggggcagctg     180
gggcgggtgg ggtggtgtgg gaagccaact aaggagagcg gccttggggc ccatcaccat     240
ggaaaccgcg gagctccttc cacttcccca cccagctgat tccccaccc catcccctcc     300
tcccagcgca gccaaccggt tttgcgtccc tggagcgcac tataaaactt gcacgggtgg     360
cgctcgctgc tcagccagac ctgggtgaag gggcagtccc gtctccaact ggtaacagcc     420
ccagcaggca gaacatgagc gtcttcctgc gaaagcaa                             458
```

```
<210> SEQ ID NO 134
<211> LENGTH: 419
<212> TYPE: DNA
<213> ORGANISM: Artificial
<220> FEATURE:
<223> OTHER INFORMATION: synthetic

<400> SEQUENCE: 134
gtcctgtcca taaaaggctt ttcccgggcc ggctccccgc cggcagcgtg ccccgccccg      60
gcccgctcca tctccaaagc atgcagagaa tgtctcggca gccccggtag actgctccaa     120
cttggtgtct ttccccaaat atggagcctg tgtggagtca ctgggggagc cgggggtggg     180
gagcggagca gccagtcgcc acacacaggc acacgcaggc cccggcgccg cgccctaagg     240
agagcagcac ccacagccaa ttgccatggg ttcgttccac ttccccaccc agccgatctc     300
cccccctcct cctgcactgc agccaaccgg cttgtgcgcg tccaggagc gcgctataaa      360 acctgtgctg ggcgtgatcg gcaagcaccg gaccagggg aaggcgagca gtgccaatc      419

<210> SEQ ID NO 135
<211> LENGTH: 389
<212> TYPE: DNA
<213> ORGANISM: Artificial
<220> FEATURE:
<223> OTHER INFORMATION: synthetic

<400> SEQUENCE: 135
gtcctgtcca taaaaggctt ttcccgggcc ggctccccgc cggcagcgtg ccccgccccg      60
gcccgctcca tctccaaagc atgcagagaa tgtctcggca gccccggtag actgctccaa     120
cttggtgtct ttccccaaat atggagcctg tgtggagtca ctgggggagc cgggggtggg     180
gagcggagcc ggcgaggggg ccgcgaggga ccctccccaa ctccacccct tcggcctcct     240
cccctttccc agccgcgggc agctccgggt ctataaagag aggcgtccga ggacgcgcag     300
ggagatttgg acgctccggc ctgggaggtg cgtcagatcc gagctcgcca tccagtttcc     360
tctccactag tcccccagt tggagatct                                       389

<210> SEQ ID NO 136
<211> LENGTH: 1199
<212> TYPE: DNA
<213> ORGANISM: Artificial
<220> FEATURE:
<223> OTHER INFORMATION: synthetic

<400> SEQUENCE: 136
actcccctct ctcctcttta accttactta ataagaccct ggcacagttg atattttaag      60
agggctactc tgttttccca gagggaccta ggcacggtaa ccctcttagc atgcagacct     120
tgtttcctga ggggtaatgt ttcccttccc tgtgacttgt ttcttggggg ctgtgttctg     180
attttcctgc tgagccactt gttgccttgg gctggctgcc gcgcttggca gttttttagtg    240 agggctctga tagatgccag gaggtgaggg gaagggctct gggtggactc cgtcattgga     300
caagcagact tagtgatgga tgagccttcc cctgaggaag ttttggatca gaagtccaac     360
tgataagttt ttccagaatt gagtaaccca gaagcagtgc cgaaaggatc ttacctctct     420
tgtggctttt tgtattgatt ttaaaagaaa ttctcagagg cagttccaca ttgtactgga     480
agcacagcta tatccacaat aggcttagat atatgtaaca tgaattgctt tagaaataac     540
atttgaggag aggggtgaga ggaaggaaga gagggtctta aaaaatagcc ctatcaaaat     600
attttctttc ttctaagtat tgaaaagaca caatataacc ctttcttctt tcaaatgatc     660
tcatagctat ttgttgaggg gaaataccaa atgtttatta ttttttttga agaagcttct     720
```

```
tcggtcctga tgattcatgt tgatatcatt ttcctcctga ctacagaggc tctgagacaa    780
agctacacct caagtgatat gccagggtca gaacaattcc cgtcctgaag gagggtgtgc    840
aaccttcttt atccctcctt cacagacgtc cttgagccct tgagacggat gtgagtgagt    900
ttttcagtcc tcatgcaaaa caaccatcta aacataacag atgacatcag cttgggcttt    960
tcaattcctg gatggcagca gcgtgttaat ccagccttca tcctggattt cataaaccaa   1020
aacaagagag cctggcagga ggacagcgct gctgctgggt tgaggaaatt gatgacgtta   1080
aagcatgcgg gcaacccagt gtataaaact cataaacgtg taggcagagg ctcagctacc   1140
agtttggacg gctgcttccc accagcaaag accacgactg gagagccgag ccggaggca    1199

<210> SEQ ID NO 137
<211> LENGTH: 958
<212> TYPE: DNA
<213> ORGANISM: Artificial
<220> FEATURE:
<223> OTHER INFORMATION: synthetic

<400> SEQUENCE: 137
cccctgggac ctgagctggt tcgcagtctt cccaaaggtg ccaagcaagc gtcagttccc     60
ctcaggcgct ccaggttcag tgccttgtgc cgagggtctc cggtgccttc ctagacttct    120
cgggacagtc tgaaggggtc aggagcggcg ggacagcgcg ggaagagcag gcaaggggag    180
acagccggac tgcgcctcag tcctccgtgc caagaacacc gtcgcggagg cgcggccagc    240
ttcccttgga tcggactttc cgcccctagg gccaggcggc ggagcttcag ccttgtccct    300
tccccagttt cgggcggccc ccagagctga gtaagccggg tggagggagt ctgcaaggat    360
ttcctgagcg cgatgggcag gaggaggggc aagggcaaga gggcgcggag caaagaccct    420
gaacctgccg gggccgcgct cccgggcccg cgtcgccagc acctcccac gcgcgctcgg     480 ccccgggcca cccgccctcg tcggcccccg cccctctccg tagccgcagg gaagcgagcc    540
tgggaggaag aagagggtag gtggggaggc ggatgagggg tgggggaccc cttgacgtca    600
ccagaaggag gtgccggggt aggaagtggg ctggggaaag gttataaatc gccccgccc    660 tcggctgctc ttcatcgagg tccgcgggag gctcggagcg cgccaggcgg acactcctct    720
cggctcctcc ccggcagcgg cggcggctcg gagcgggctc cggggctcgg gtgcagcggc    780
cagcgggcgc ctggcggcga ggattacccg gggaagtggt tgtctcctgg ctggagccgc    840
gagacgggcg ctcagggcgc ggggccggcg cggcgaacg agaggacgga ctctggcggc    900
cgggtcgttg gccgcgggga gcgcgggcac cgggcgagca ggccgcgtcg cgctcacc    958

<210> SEQ ID NO 138
<211> LENGTH: 178
<212> TYPE: DNA
<213> ORGANISM: Artificial
<220> FEATURE:
<223> OTHER INFORMATION: synthetic

<400> SEQUENCE: 138
ctagaccgcc cctagggaaa gtcccctagg gcgggtctag atagaagact ggtgcacgtg     60
gcttcccaaa gatctctcag ataatgagag gaaatgcagt catcagtttg cagaaggcta    120
gggattctgg gccatagctc agacctgcgc ccaccatctc cctccaggca gcccttgg      178

<210> SEQ ID NO 139
<211> LENGTH: 298
<212> TYPE: DNA
<213> ORGANISM: Artificial
```

```
-continued

<220> FEATURE:
<223> OTHER INFORMATION: synthetic

<400> SEQUENCE: 139
ctagaagagg gcctgttgga gcccacgtat gcactgtggc tagggaaagt cccctagctc        60
cagaagcaaa gcaccccatt ggaatgaaaa gtatgaagta cctagccaca gtgcatacgt       120
gggctccaac aggtcctctt catgggtctc ggtctcctag atagaagact ggtgcacgtg       180
gcttcccaaa gatctctcag ataatgagag gaaatgcagt catcagtttg cagaaggcta       240
gggattctgg gccatagctc agacctgcgc ccaccatctc cctccaggca gcccttgg        298
```